(12) United States Patent
Diacovo

(10) Patent No.: US 11,969,428 B2
(45) Date of Patent: Apr. 30, 2024

(54) METHODS AND PHARMACEUTICAL COMPOSITIONS FOR TREATING LYMPHOID MALIGNANCY

(71) Applicant: Thomas Diacovo

(72) Inventor: Thomas Diacovo, New York, NY (US)

(73) Assignee: Thomas Diacovo, Larchmont, NY (US)

( * ) Notice: Subject to any disclaimer, the term of this patent is extended or adjusted under 35 U.S.C. 154(b) by 0 days.

(21) Appl. No.: 16/950,413

(22) Filed: Nov. 17, 2020

(65) Prior Publication Data

US 2021/0315901 A1 Oct. 14, 2021

Related U.S. Application Data

(63) Continuation of application No. 16/211,361, filed on Dec. 6, 2018, now abandoned, which is a continuation
(Continued)

(51) Int. Cl.
*G01N 33/573* (2006.01)
*A61K 31/52* (2006.01)
(Continued)

(52) U.S. Cl.
CPC ............ *A61K 31/52* (2013.01); *A61K 31/573* (2013.01); *A61K 31/713* (2013.01);
(Continued)

(58) Field of Classification Search
CPC . C12N 9/1205; C12N 15/1137; A61K 31/573
See application file for complete search history.

(56) References Cited

U.S. PATENT DOCUMENTS 6,667,300 B2 * 12/2003 Sadhu ................. C07D 473/40
514/266.3
8,785,470 B2 7/2014 Castro et al.
(Continued)

FOREIGN PATENT DOCUMENTS

CN 101550135 A 10/2009
JP 2015536948 A 12/2015
(Continued)

OTHER PUBLICATIONS

Lonetti et al. (Oncotarget, 2015 vol. 6:10399-10414).*
(Continued)

*Primary Examiner* — Terra C Gibbs
(74) *Attorney, Agent, or Firm* — Scully, Scott, Murphy & Presser, P.C.

(57) ABSTRACT

The present invention provides, inter alia, methods for treating, preventing, or ameliorating the effects of a lymphoid malignancy, such as those associated with a mutated phosphatase and tensin homolog (PTEN) gene, or T-cell acute lymphoblastic leukemia (T-ALL). These methods include administering to a subject an effective amount of a phosphoinositide 3-kinase-delta (PI3Kδ) inhibitor and a phosphoinositide 3-kinase-gamma (PI3Kγ) inhibitor. The present invention also provides pharmaceutical compositions for treating the effects of a lymphoid malignancy. This invention further provides a method for identifying a subject who may benefit from co-treatment with a PI3Kδ inhibitor and a PI3Kγ inhibitor. This method includes determining from a sample of the subject whether the subject has a mutated PTEN gene. Additionally, this invention provides methods for identifying a compound that has both PI3Kδ and PI3Kγ inhibitory activity.

15 Claims, 40 Drawing Sheets

Related U.S. Application Data of application No. 15/451,306, filed on Mar. 6, 2017, now abandoned, which is a continuation of application No. 14/003,873, filed as application No. PCT/US2012/027148 on Feb. 29, 2012, now abandoned.

(60) Provisional application No. 61/450,341, filed on Mar. 8, 2011.

(51) Int. Cl.
| | | |
|---|---|---|
| A61K 31/573 | (2006.01) | |
| A61K 31/713 | (2006.01) | |
| C12N 9/12 | (2006.01) | |
| C12N 15/113 | (2010.01) | |
| C12Q 1/6886 | (2018.01) | |
| G01N 33/50 | (2006.01) | |

(52) U.S. Cl.
CPC ........ *C12N 9/1205* (2013.01); *C12N 15/1137* (2013.01); *C12Q 1/6886* (2013.01); *C12Y 207/01137* (2013.01); *C12Y 207/01153* (2013.01); *G01N 33/5041* (2013.01); *G01N 33/573* (2013.01)

(56) References Cited

U.S. PATENT DOCUMENTS

| 2002/0016014 A1 | 2/2002 | Kimura |
| 2013/0071323 A1 | 3/2013 | Gallatin et al. |

FOREIGN PATENT DOCUMENTS

| RU | 2358969 C2 | 6/2009 |
| WO | 2001081346 A2 | 3/2002 |
| WO | 2005113556 A1 | 12/2005 |
| WO | 2010057048 A1 | 5/2010 |
| WO | 2011008302 A1 | 1/2011 |
| WO | 2013082540 A1 | 6/2013 |
| WO | 2014071109 A1 | 5/2014 |
| WO | 2014100767 A1 | 6/2014 |
| WO | 2014128612 A1 | 8/2014 |
| WO | 2015200352 A1 | 12/2015 |

OTHER PUBLICATIONS

Stengel et al. (British Journal of Haematology, 2013 vol. 162:278-291).*
Anderson et al., "Lymphostromal interactions in thymic development and function", Nat Rev Immunol; 1: 31-40 (2001).
Armstrong et al., "NOTCH is a key regulator of human T-cell acute leukemia initiating cell activity", Blood 113, 1730-1740 (2009).
Ashwell et al., "Glucocorticoids in T cell development and function", Annu Rev Immunol; 18: 309-345 (2000).
Ayala et al., "Contribution of bone microenvironment to leukemogenesis and leukemia progression", Leukemia 23, 2233-2241 (2009).
Balakrishnan et al., "The phosphoinositide-3-kinase (PI3K)-delta and gamma inhibitor, IPI-145 (Duvelisib), overcomes signals from the PI3K/AKT/S6 pathway and promotes apoptosis in CLL", Leukemia Sep. 2015: 29(9): pp. 1811-1822.
Beesley et al., "Glucocorticoid resistance in T-lineage acute lymphoblastic leukaemia is associated with a proliferative metabolism", British Journal of Cancer 100, 1926-1936 (2009).
Bernard et al., "Molecular mechanisms of a t(8;14)(q24;q11) translocation juxtaposing c-myc and TcR-alpha genes in a T-cell leukaemia: involvement of a V alpha internal heptamer", Oncogene 2, 195-200 (1988).
Borowski et al., "On the brink of becoming a T cell", Curr Opin Immunol.; 14: 200-206 (2002).
Burger et al., "The microenvironment in mature B-cell malignancies: a target for new treatment strategies", Blood 114, 3367-3375 (2009).

CAL-130 (Racemate) | C23H22N8O- PubChem (downloaded from https://pubchem.ncbi.nlm.nih.gov/compound/CAL-130-_Racemate on May 14, 2020).
Camps et al., "Blockade of PI3γ suppresses joint inflammation and damage in mouse models of rheumatoid arthritis," Nature Medicine, vol. 11, No. 9, pp. 936-943, Sep. 2005.
Cante-Barrett et al., "MEK and PI3K-AKT inhibitors synergistically block activated IL& receptor signaling in T-cell acute lymphoblastic leukemia", Leukemia, Advanced online publication, May 2016.
Cantley, "The phosphoinositide 3-kinase pathway", Science; 296: 1655-1657 (2002).
Carnero et al., "The PTEN/PI3K/AKT signalling pathway in cancer, therapeutic implications", Curr. Cancer Drug Targets 8, 187-198 (2008).
Cella et al., "Differential requirements for Vav proteins in DAP10- and ITAM-mediated NK cell cytotoxicity", J Exp Med. 200: 817-823 (2004).
Chemical Book. IC-87114. Chemical Product Property. Downloaded at http://www.chemicalbook.com/ChemicalProductProperty_EN_CB12485097.htm on May 17, 2016.
Clayton et al., "A crucial role for the p110delta subunit of phosphalidylinositol 3-kinase in B cell development and activation", J Exp Med. 196: 753-763 (2002).
Cohen et al., "The renaissance of GSK3", Nat. Rev. Mol. Cell. Biol. 2, 769-776 (2001).
Collazo et al., "SHIP limits immunoregulatory capacity in the T-cell compartment", Blood 113, 2934-2944 (2009).
Collins et al., "Views on Vav." Immunol Today, 18: 221-225 (1997).
Crouthamel et al., "Mechanism and management of AKT inhibitor-induced hyperglycemia", Clin. Cancer Res. 15. 217-225 (2009).
Diacovo, "Elucidating and Targeting Non-classical Oncogenes for Therapy in T-ALL", Global Technology Community—Protein Kinases and Drug Design, Nov. 2012.
Downward, "PI 3-kinase, Aki and cell survival", Semin Cell Dev Biol. 15: 177-182 (2004).
Dudley et al., "T cell receptor beta chain gene rearrangement and selection during thymocyte development in adult mice", Immunity 1: 83-93 (1994).
Duronio, "The life of a cell: apoptosis regulation by the PI3K/PKB pathway", Biochem. J_ 415, 333-344 (2008).
Erlacher et al., "BH3-only proteins Puma and Bim are rate-limiting for gamma-radiation- and glucocorticoid-induced apoptosis of lymphoid cells in vivo", Blood 106, 4131-4138 (2005).
Fabian et al., "A small molecule-kinase interaction map for clinical kinase inhibitors", Nat. Biotechnol. 23, 329-336 (2005).
Falk et al., "Immature thymocytes that fail to express TCR-bela and/or TCRgamma delta proteins die by apoptotic cell death in the CD44(-)CD25(-) (DN4) subset", Eur J Immunol. 31: 3308-3317 (2001).
Finger et al., "A common mechanism of chromosomal translocation in T- and B-cell neoplasia", Science 234, 982-985 (1986).
Finlay et al., "Phosphoinositide-dependent kinase 1 controls migration and malignant transformation but not cell growth and proliferation in PTEN-null lymphocytes", J_ Exp. Med. 206, 2441-2454 (2009).
Flinn et al., "Duvelisib, a novel oral dual inhibitor of PI3K-σ,γ, is clinically active in advanced hematologic malignancies", Blood, vol. 131/Issue 8, pp. 877-887, Feb. 2018.
Foukas et al., "Activity of any class IA PI3K isoform can sustain cell proliferation and survival", Proc. Natl. Acad. Sci. USA. 107, 11381-11386 (2010).
Franke et al., "PI3K/Akt and apoptosis: size matters", Oncogene. 22: 8983-8998 (2003).
Fruman et al., "Impaired B cell development and proliferation in absence of phosphoinositide 3-kinase p85alpha. Science", 283: 393-397 (1999).
Fruman et al., "The PI3K pathway in human disease", Cell, Aug. 2017; 170(4); pp. 605-635.
Gedman et al., "The impact of NOTCH1, FBW7 and PTEN mutations on prognosis and downstream signaling in pediatric T-cell acute lymphoblastic leukemia: a report from the Children's Oncology Group", Leukemia 23 (8):1417-1425 (2009).

(56) References Cited

OTHER PUBLICATIONS

GERMAIN "T-cell development and the CD4-CD8 lineage decision", Nat Rev Immunol. 2: 309-322 (2002).
Gratiot-Deans et al., "Bcl-2 proto-oncogene expression during human T cell development: evidence for biphasic regulation". J Immunol. 151: 83-91 (1993).
Guo et al., "Multi-genetic events collaboratively contribute to Pten-null leukaemia stem-cell formation", Nature 453, 529-533 (2008).
Guo et al., "Suppression of leukemia development caused by PTEN loss", Proc. Natl. Acad. Sci. USA. 108, 1409-1414 (2011).
Gutierrez et al., "High frequency of PTEN, PI3K, and AKT abnormalities in T-cell acute lymphoblastic leukemia", Blood 114, 647-650 (2009).
Hagenbeek et al., "T-cell lymphomas in T-cell-specific Pten-deficient mice originate in the thymus", Leukemia 22. 608-619 (2008).
Hagenbeek et al., "The loss of PTEN allows TCR alpha beta lineage thymocytes to bypass IL-7 and Pre TCR-mediated signaling", J_ Exp. Med. 200, 883-889 (2004).
Hennet et al., "T-cell-specific deletion of a polypeptide N-acetylgalactosaminyl-transferase gene by site-directed recombination", Proc. Natl. Acad. Sci. USA 92, 12070-12074 (1995).
Hickey et al., "BCR-ABL regulates phosphatidylinositol 3-kinase-p110gamma transcription and activation and is required for proliferation and drug resistance", J_ Biol. Chem. 281, 2441-2450 (2005).
Hinton et al., "The serine kinase phosphoinositide-dependent kinase 1 (PDK1) regulates T cell development", Nat. Immunol. 5, 539-545 (2004).
Hoellenriegel et al., "The phosphoinositide 3'-kinase delta inhibitor, CAL-101, inhibits B-cell receptor signaling and chemokine networks in chronic lymphocytic leukemia", Blood 118, 3603-3612 (2011).
Horwitz et al., "Activity of the PI3K-o,y inhibitor duvelisib in a phase 1 trial and preclinical models of T-celllymphoma", Blood, vol. 141/Issue 8, pp. 888-898, Feb. 2018.
Huang et al., "Induction of Akt activity by chemotherapy confers acquired resistance", J_ Formos. Med. Assoc. 108, 180-189 (2009).
International Preliminary Report on Patentability dated Feb. 13, 2020 issued in PCT/US2018/044659.
International Search Report and Written Opinion issued in application No. PCT/US2018/044659, dated Sep. 20, 2018.
Jackson et al., "PI 3-kinase p110beta: a new target for antithrombotic therapy", Nat. Med. 11, 507-514 (2005).
Ji et al., "Inactivation of PI3Kgamma and PI3Kdelta distorts T-cell development and causes multiple organ inflammation", Blood 110, 2940-2947 (2007).
Jia et al., "Essential roles of PI(3)K-p110beta in cell growth, metabolism and tumorigenesis", Nature 454, 776-779 (2008).
Jordan et al., "Adaptors as central mediators of signal transduction in immune cells", Nat Immunol. 4: 110-116 (2003).
Kang et al., "Oncogenic transformation induced by the p11 Obela, -gamma, and -delta isoforms of class I phosphoinosilide 3-kinase", Proc. Nall. Acad. Sci.US A. 103, 1289-1294 (2006).
Jotta et al., "Negative prognostic impact of PTEN mutation in pediatric T-cell acute lymphoblastic leukemia". Leukemia 24, 239-242 (2010).
Katso, "Cellular function of phosphoinosilide 3-kinases: implications for development, homeostasis, and cancer". Ann. Rev. Cell Dev. Biol. 17, 615-675 (2001).
Komada et al., "Expression of Three Major Protein Kinase C Isozymes in Various Types of Human Leukemic Cells", Cancer Research, Aug. 15, 1991 vol. 51 :4271-4278.
Kong et al., "Vav regulates peptide-specific apoptosis in thymocytes", J Exp Med., 188: 2099-2111 (1998).
Konopleva et al., "Therapeutic targeting of microenvironmental interactions in leukemia: mechanisms and approaches", Drug Resist. Updal. 12, 103-113 (2009).
Kroemer, "The proto-oncogene Bcl-2 and its role in regulating apoptosis", Nat Med. vol. 3: 614-620 (Jun. 1997).

Krutzfeldt et al., "Silencing of microRNAs in vivo with 'antagomirs',", Letters, Dec. 2005, vol. 438, pp. 685-689, Nature Publishing Group.
Ksiondra et al., "Comprehensive analysis of T cell leukemia signals reveals heterogeneity in the PI3 kinase-Akt pathway and limitations of PI3 kinase inhibitors as monotherapy", PLos One, vol. 13/ Issue 5, May 2018.
Lannutti et al., "CAL-101, a p1108 selective phosphatidylinositol-3-kinase inhibitor for the treatment of B-cell malignancies, inhibits PI3K signaling and cellular viability," Blood, vol. 117, No. 2, pp. 591-594, Jan. 2011.
Lewis et al., "Tec kinases: modulators of lymphocyte signaling and development". Curr Opin Immunol. 13: 317-325 (2001).
Linette et al., "Differentiation and cell death: lessons from the immune system", Curr Opin Cell Biol. 6: 809-815 (1994).
Liu et al., "Distinct roles for PTEN in prevention of T cell lymphoma and autoimmunity in mice", J_ Clin. Invest. 20, 2497-2507 (2010).
Lo et al., Inactivation of SHIP1 in T-cell acute lymphoblastic leukemia due to mutation and extensive alternative splicing: Leuk. Res. 33, 1562-1566 (2009).
Lonetti et al., "PI3K pan-inhibition impairs more efficiently proliferation and survival of T-cell acute lymphoblastic leukemia cell lines when compared to isoform-selective PI3K inhibitors". Oncotarget. vol.6/Issue 12, pp. 10399-10414, Apr. 2015.
Magallon et al., "Humanized mouse model of thrombosis is predictive of the clinical efficacy of antiplatelet agents", Circulation 123, 319-326 Jan. 25, 2011.
Marone et al., "Targeting phosphoinositide 3-kinase: moving towards therapy", Biochim Biophys Acta. Jan. 2008; 1748(10): pp. 159-185.
Maser et al., "Chromosomally unstable mouse tumours have genomic alterations similar to diverse human cancers", Nature 447, 966-971 (2007).
Mckean et al., "Maturation versus Death of developing double-positive thymocytes reflects competing effects on Bcl-2 expression and can be regulated by the intensity of CD28 costimulation", J Immunol. 166: 3468-3475 (2001).
Melendez et al., "Aggregation of the human high affinity immunoglobulin G receptor (FcgammaRI) activates both tyrosine kinase and G protein-coupled phosphoinositide 3-kinase isoforms", Proc Nall Acad Sci U S A. 95: 2169-2174 (1998).
Michie et al., "Regulation of thymocyte differentiation: pre-TCR signals and beta-selection", Semin Immunol. 14: 311-323 (2002).
NIH Grant # 5R01CA164346-04; Awardee Organization: University of Texas MD Anderson Cancer Center, "Characterization and targeted therapy of T-ALL deficient for PTEN and INK4A/AFf" PI: You.
NIH Grant #: 4R01CA169162-05 Awardee Organization: Columbia University Health Sciences Targeting non-classical oncogenes as therapy for T-ALL PI: Diacovo.
NIH Grant #: 5K08CA184418-02 Awardee Organization: Children's Hospital of Philadelphia "PI3K pathway inhibition for Philadelphia-like acute lymphoblastic leukemia" PI: Tasian.
Okkenhaug et al., "Impaired B and T cell antigen receptor signaling in p110delta PI 3-kinase mutant mice", Science. 297: 1031-1034 (2002).
Okkenhaug et al., "Phosphoinositide 3-kinase in T cell activation and survival", Biochem Soc Trans. 32: 332-335 (2004).
Okkenhaug et al., "PI3K in lymphocyte development, differentiation and activation", Nat Rev Immunol., 3: 317-330 (2003).
Palomero et al., "The role of the PTEN/AKT Pathway in NOTCH1-induced leukemia", Cell Cycle 7, 965-970 (2008).
Penit et al., "Cell expansion and growth arrest phases during the transition from precursor (CD4-8-) to immature (CD4) +8+) thymocytes in normal and genetically modified mice", J Immunol. 154: 5103-5113 (1995).
Pereira et al., "Molecular effects of the phosphatidylinositol-3-kinase inhibitor NVP-BKM120 on T and B-cell acute lymphoblastic leukaemia". European Journal of Cancer, vol. 41/Issue 14, pp. 2076-2085, Sep. 2015.
Pereira et al., "Molecular effects of the phosphatidylinositol-3-kinase inhibitor NVP-BKM120 on T and B-cell acute ymphoblastic leukemia," European Journal of Cancer, 2006, vol. 51, pp. 2076-2085, ScienceDirect, Elsevier.

(56) References Cited

OTHER PUBLICATIONS

Punt et al., "Lineage commitment in the thymus: only the most differentiated (TCRhibcl-2hi) subset of CD4 +COB+ thymocytes has selectively terminated CD4 or COB synthesis", J Exp Med. 184: 2091-2099 (1996).

Puri et al., "Mechanisms and implications of phosphoinositide 3-kinase o in promoting neutrophil trafficking into inflamed tissue", Blood 103, 3448-3456 (2004).

Puri et al., "The role of endothelial PI3Ky activity in neutrophil trafficking", Blood. 106: 150-157 (2005).

Reynolds et al., Vav1 transduces T cell receptor signals to the activation of phospholipase C-gamma1 via phosphoinositide 3-kinase-dependent and -independent pathways, J Exp Med. 195: 1103-1114 (2002).

Rodriguez-Borlado et al., "Phosphatidylinositol 3-kinase regulates the CD4/CD8 T cell differentiation ratio", J immunol. 170: 4475-4482 (2003).

Sadhu et al., "Essential role of Phosphoinositide 3-kinase o in neutrophil directional movement", J_ Immunol, 170, 2647-2654 (2003).

Safran et al., "Mouse reporter strain for noninvasive bioluminescent imaging of cells that have undergone ere-mediated recombination", Mol. Imaging 2, 297-302 (2003).

Sakai et al., "PTEN Gene Alterations in Lymphoid Neoplasms", Blood 92, p. 3410-3415 (1998).

Salmena et al., "Tenets of PTEN tumor suppression", Cell 133, 403-414 (2008).

Samuels et al., "High frequency of mutations of the PIK3CA gene in human cancers", Science 304, 554 (2004).

Sasaki et al., "Function of PI3Kgamma in thymocyte development, T cell activation, and neutrophil migration", Science. 287: 1040-1046 (2000).

Schmelzle et al., "Tor, a central controller of cell growth", Cell, 103, 253-262 (2000).

Selleckchem.com, "AS-605240 PI3K inhibitor," product sheet, downloaded Jun. 4, 2018 from http://www.selleckchem.com/products/AS605240.html.

\* cited by examiner

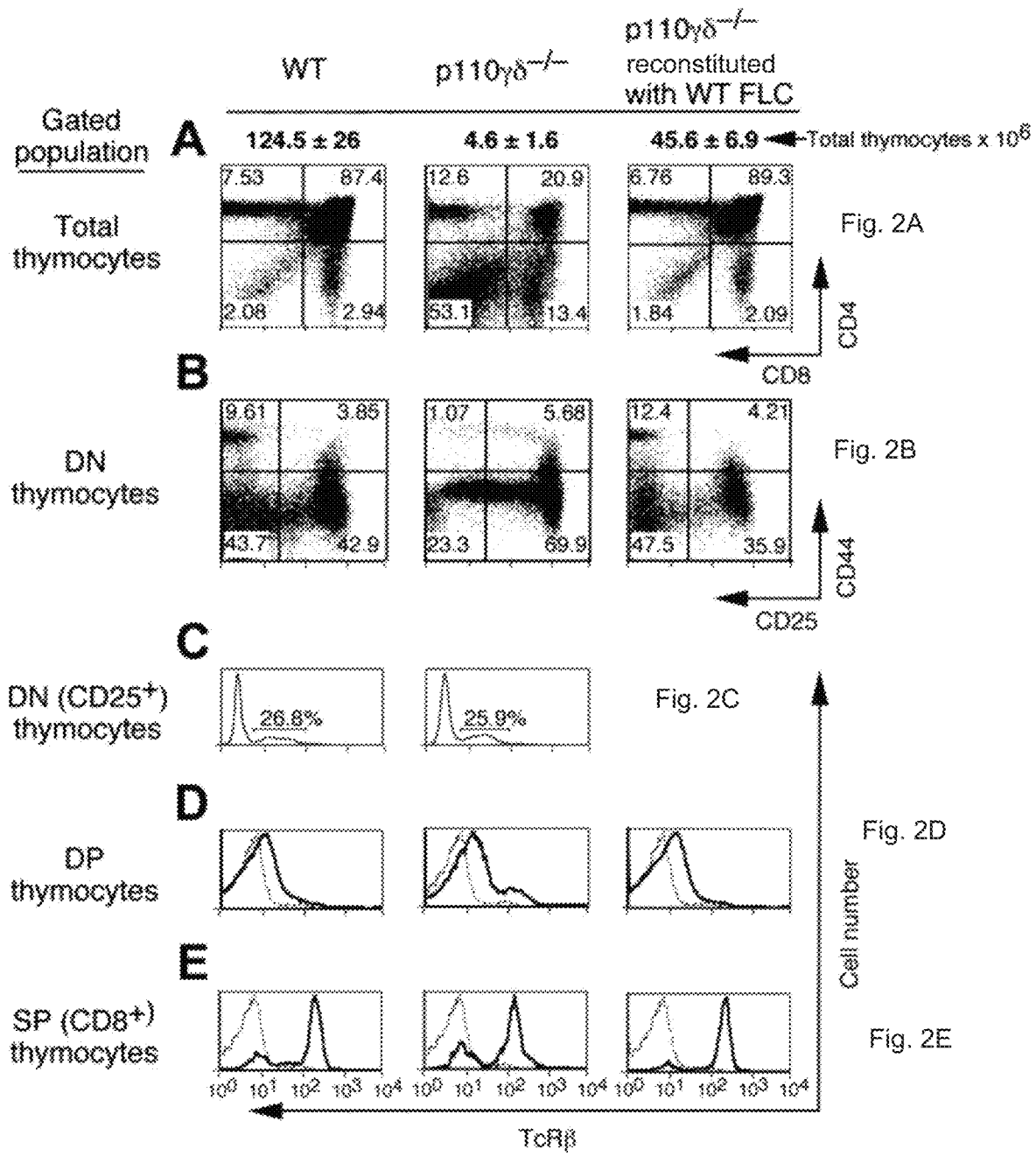

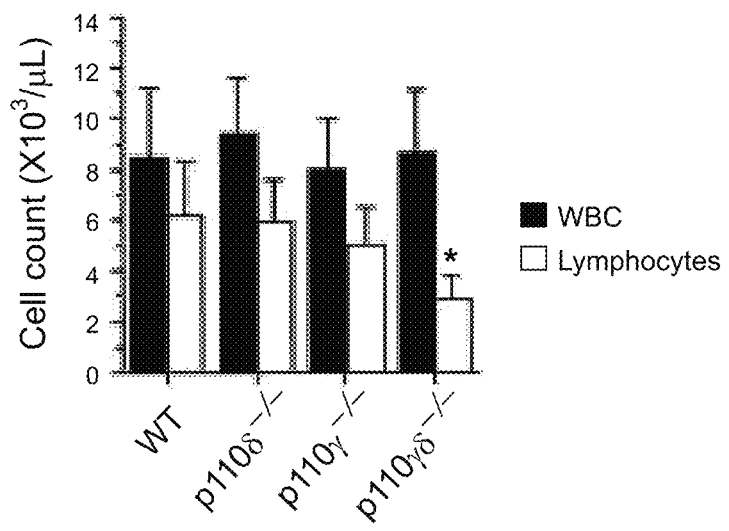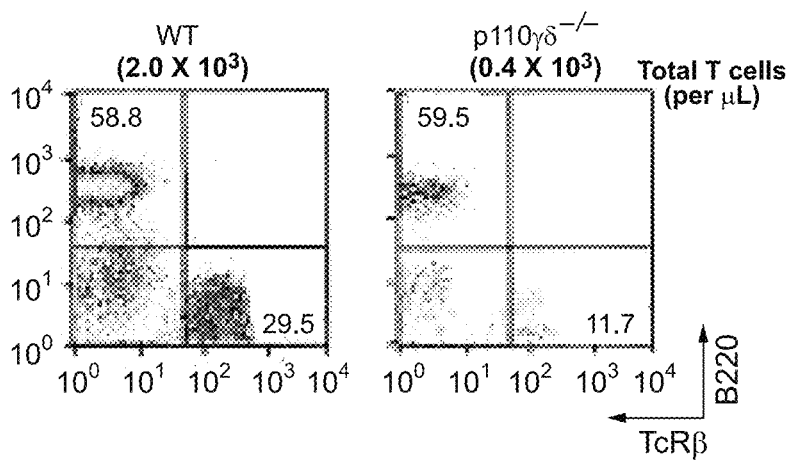
Fig. 6A

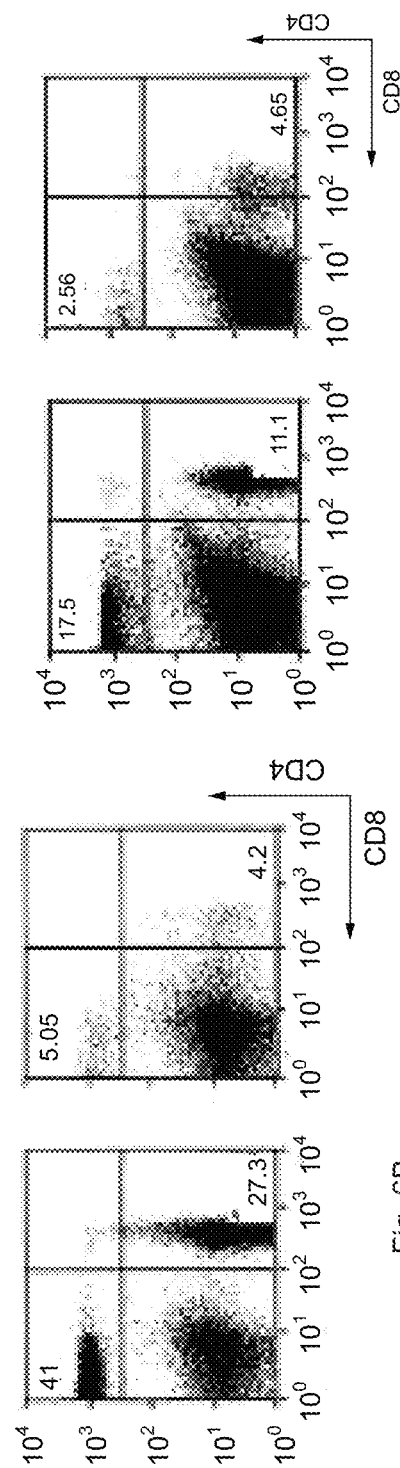
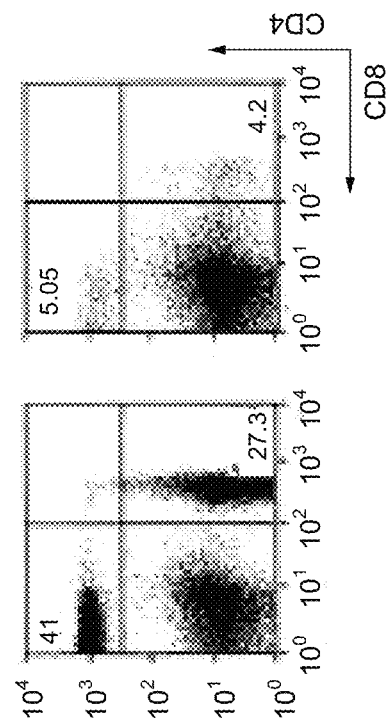
Fig. 6B
Fig. 6C

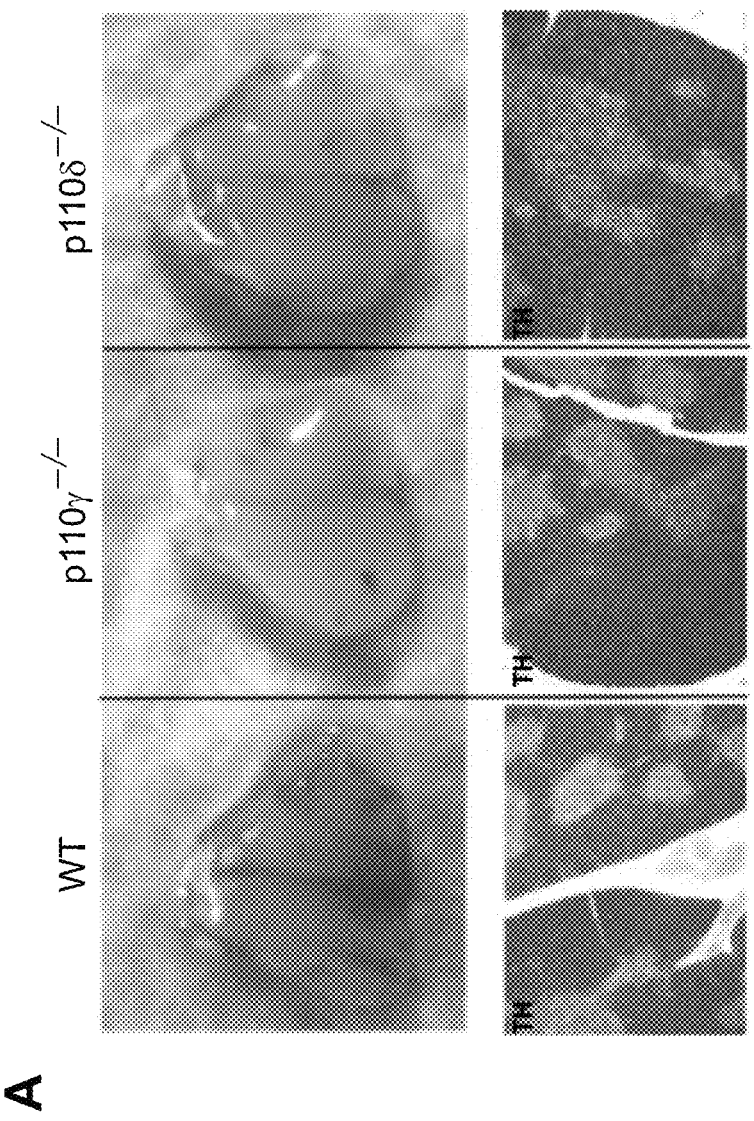

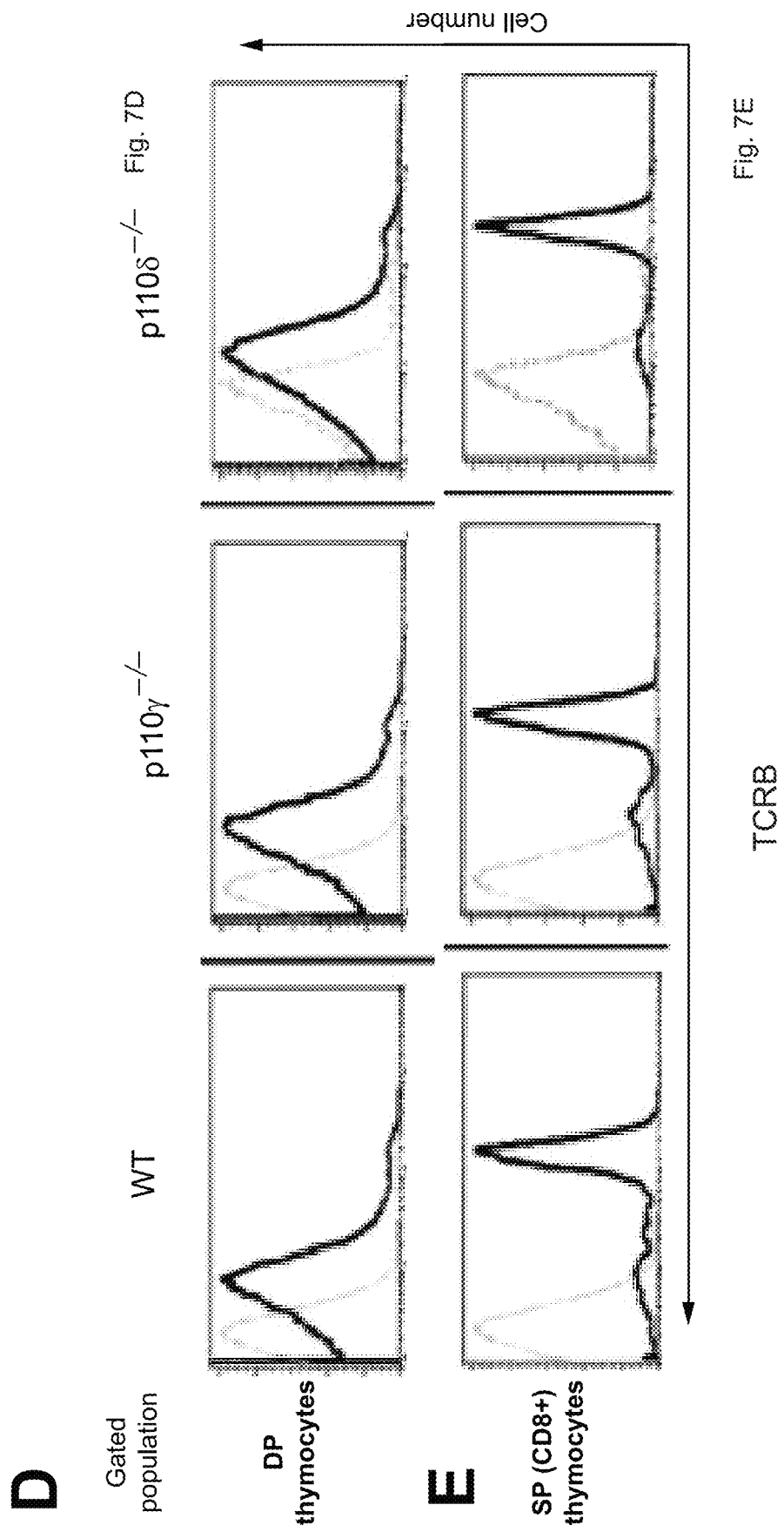

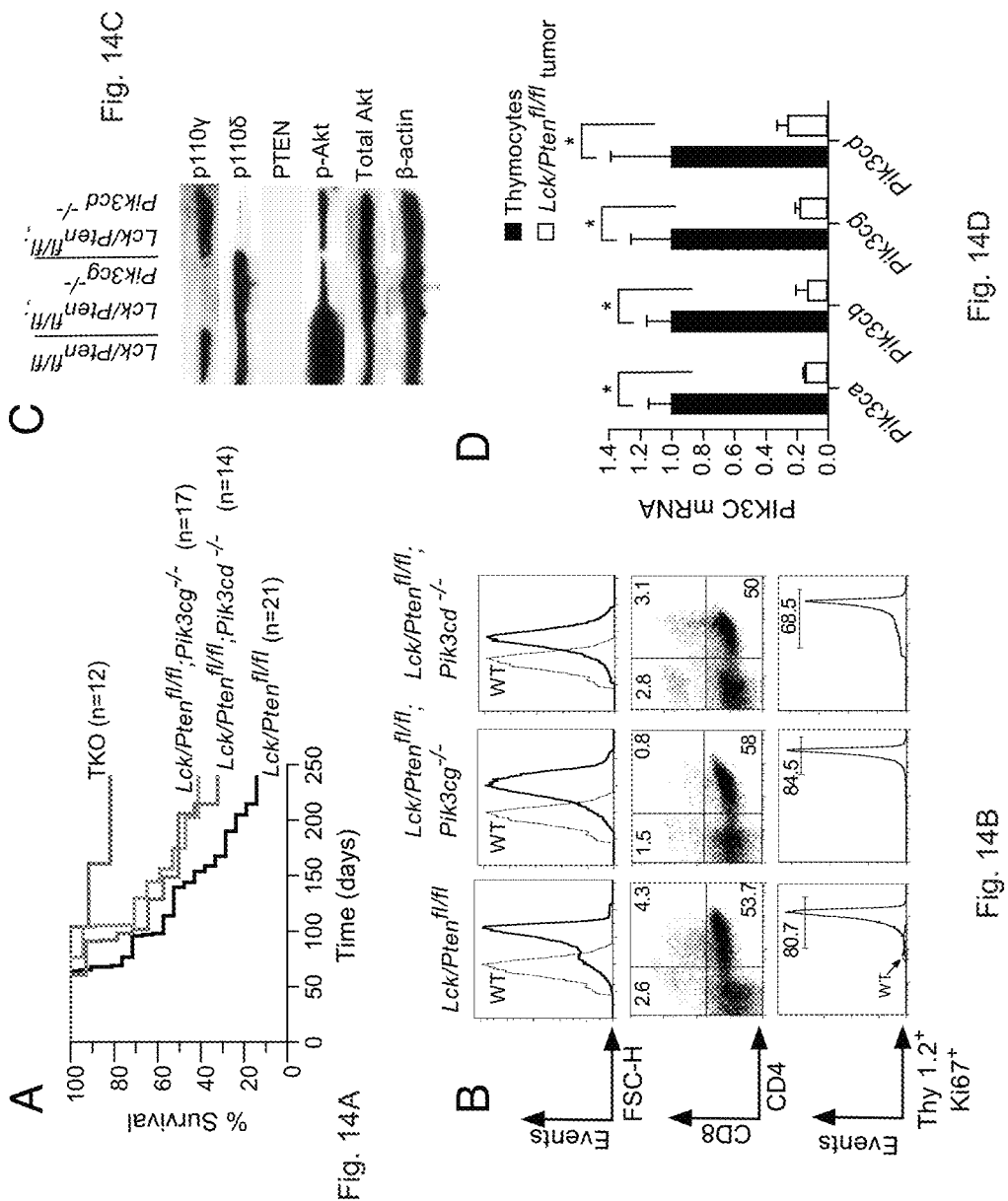

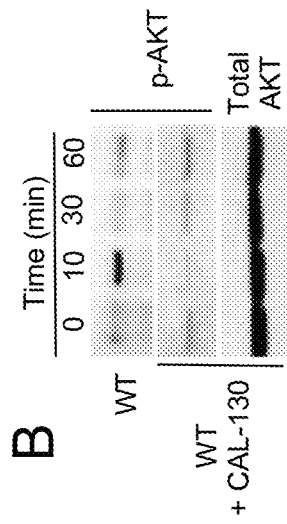
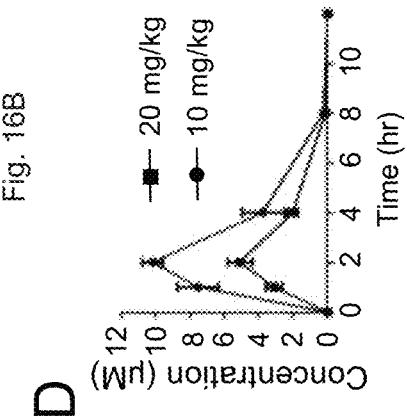
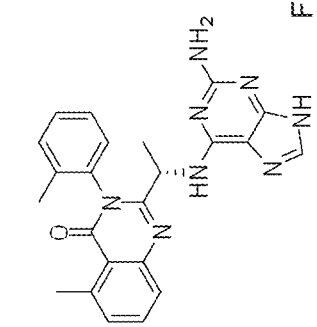
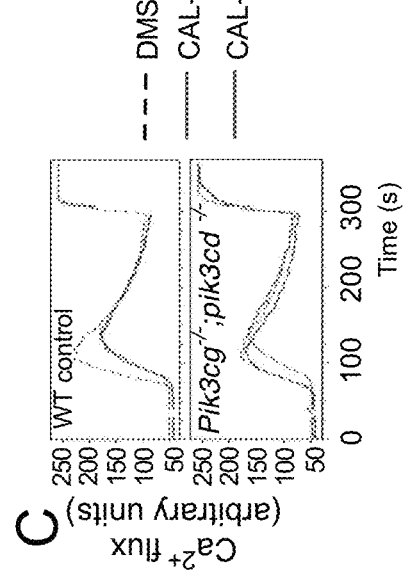
Fig. 16A
Fig. 16B
Fig. 16C
Fig. 16D

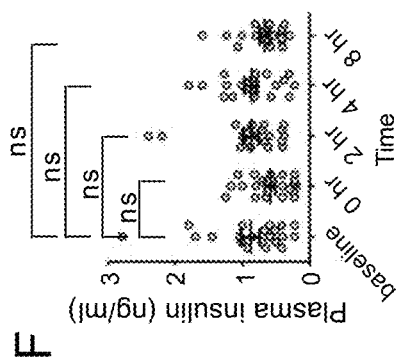
Fig. 16E
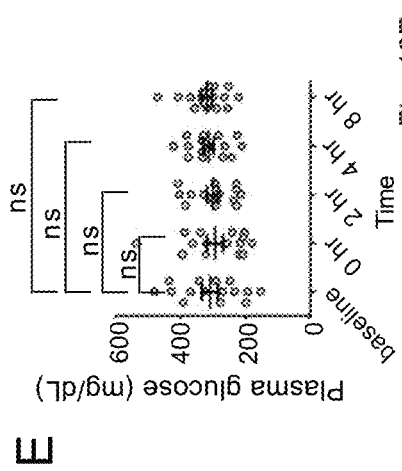
Fig. 16F
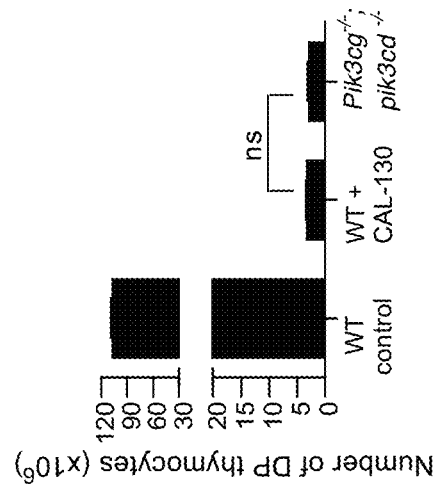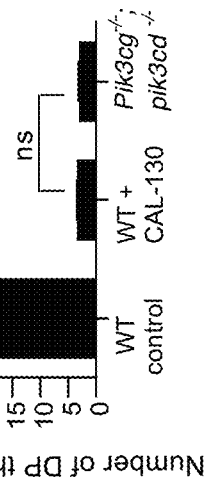
Fig. 16G
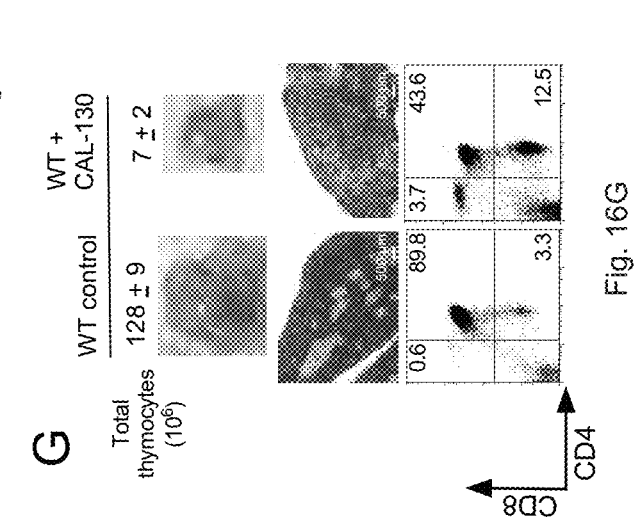
Fig. 16H

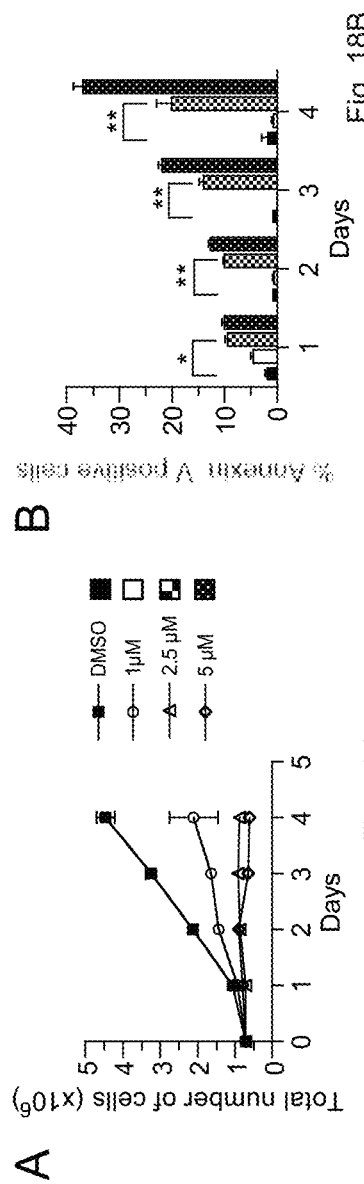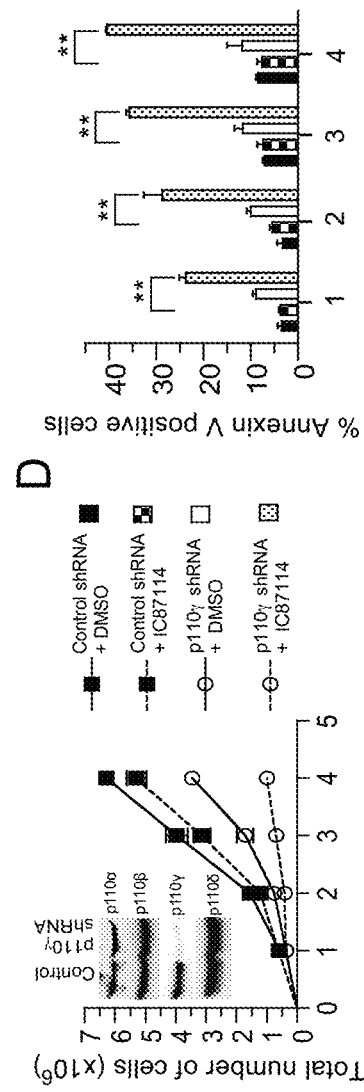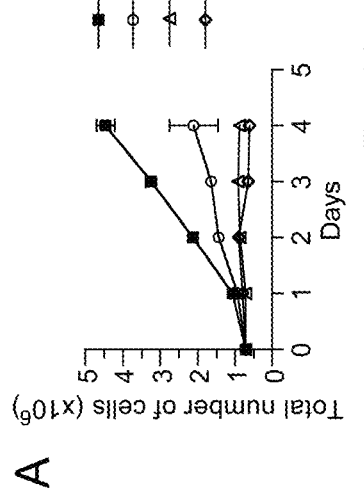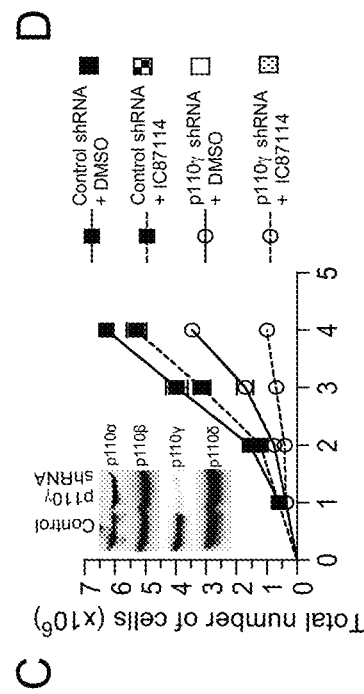

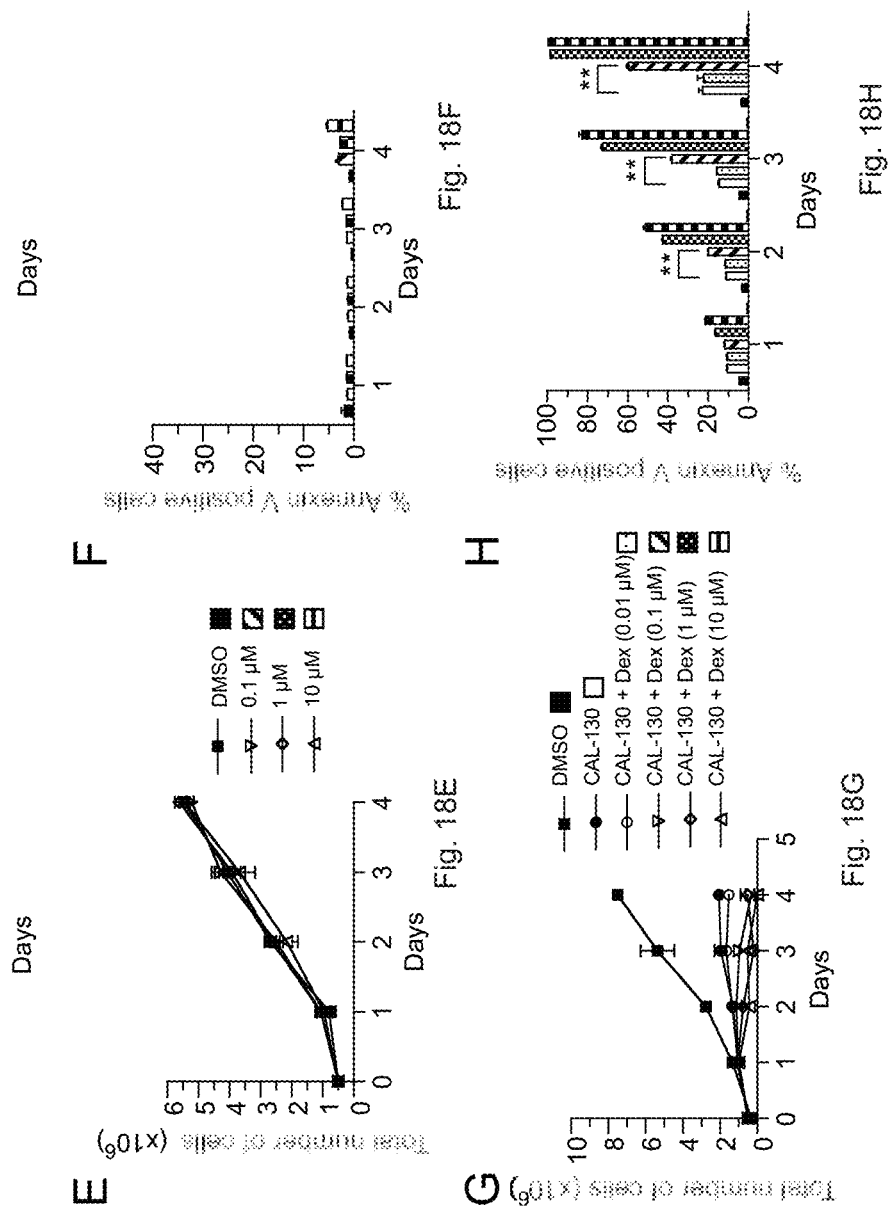

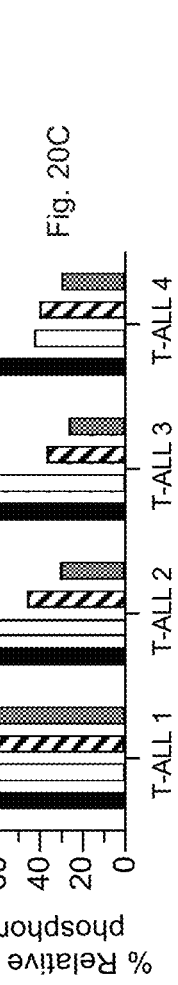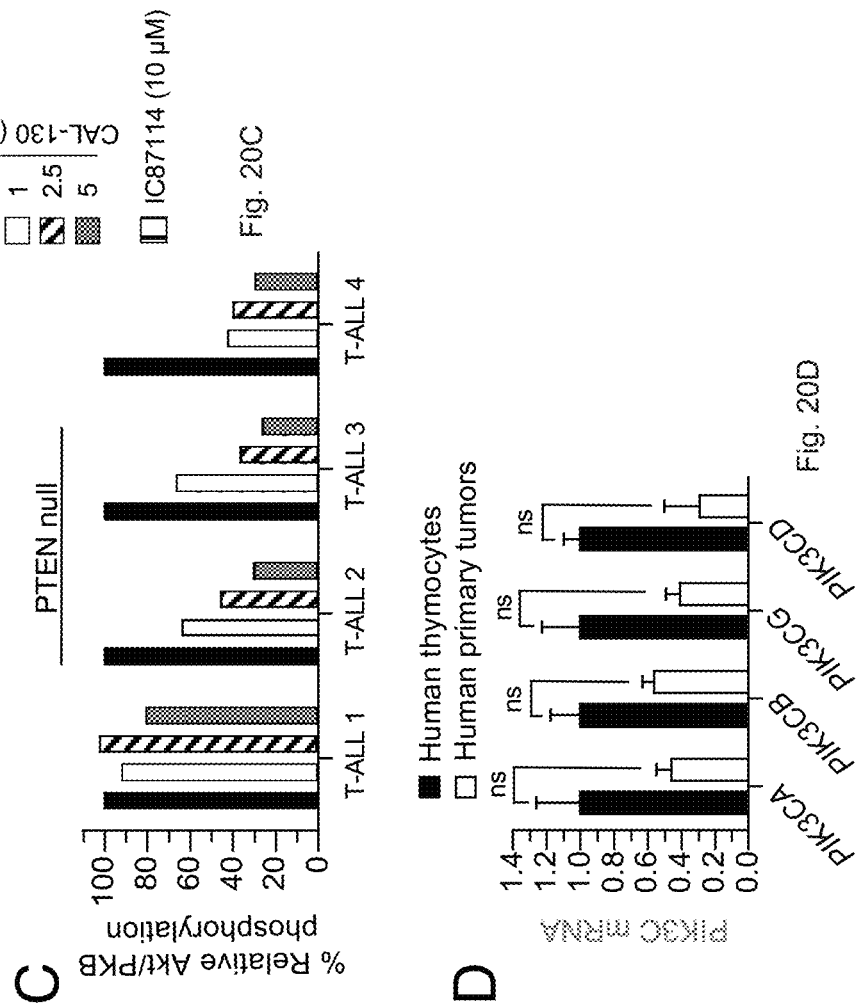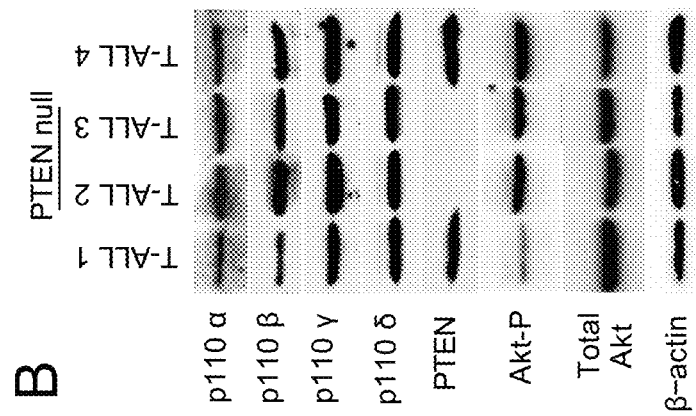
Fig. 20B
Fig. 20C
Fig. 20D

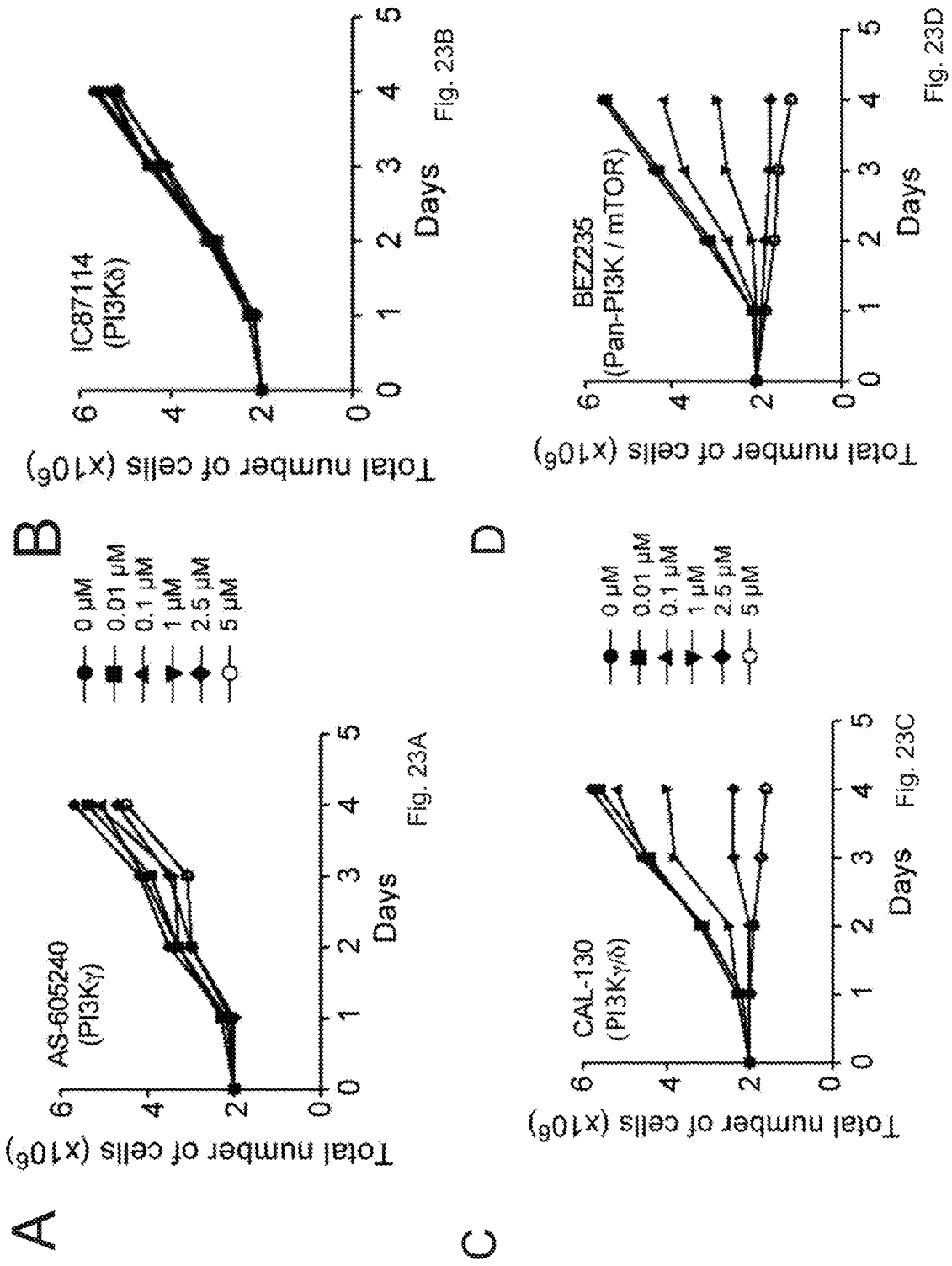

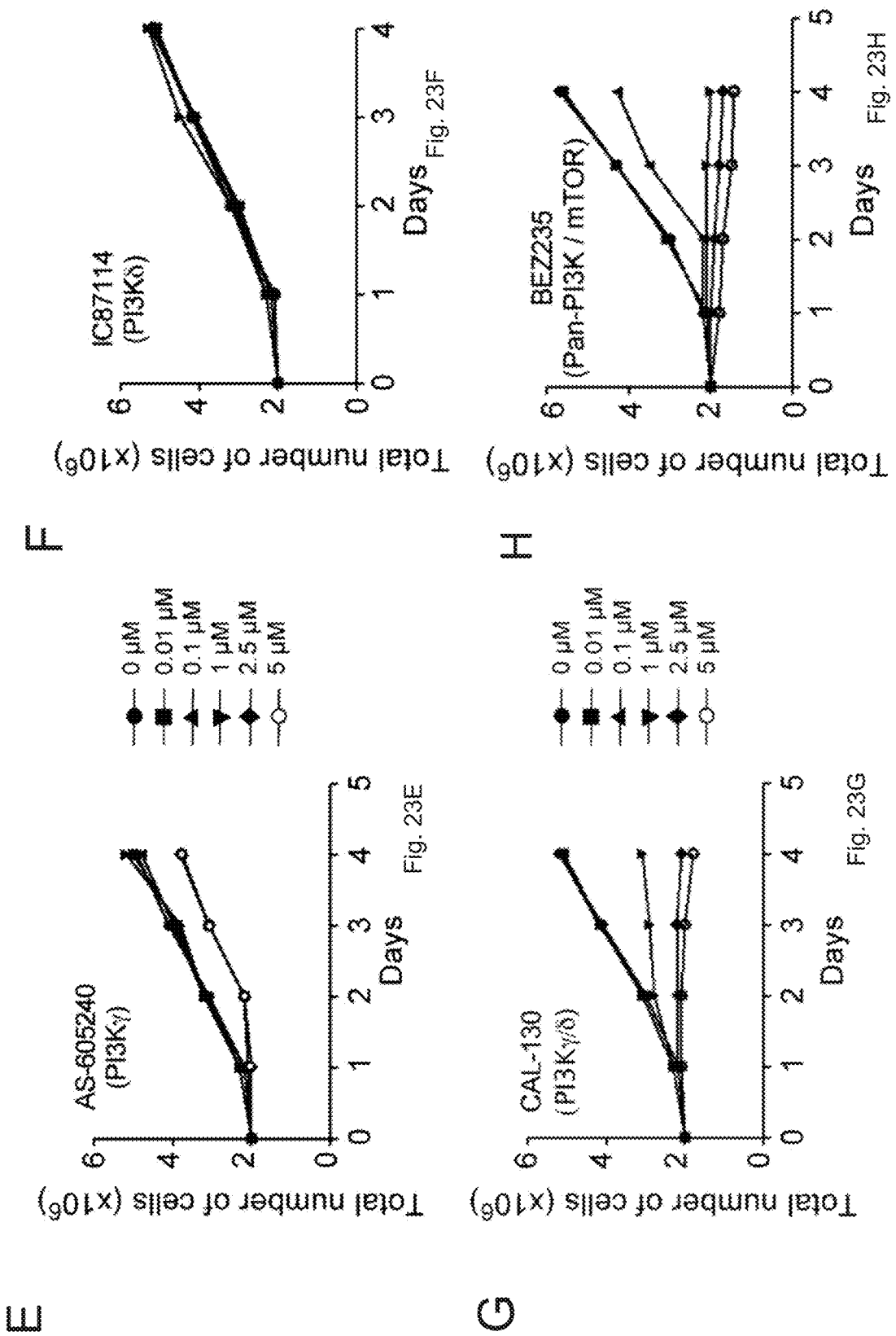

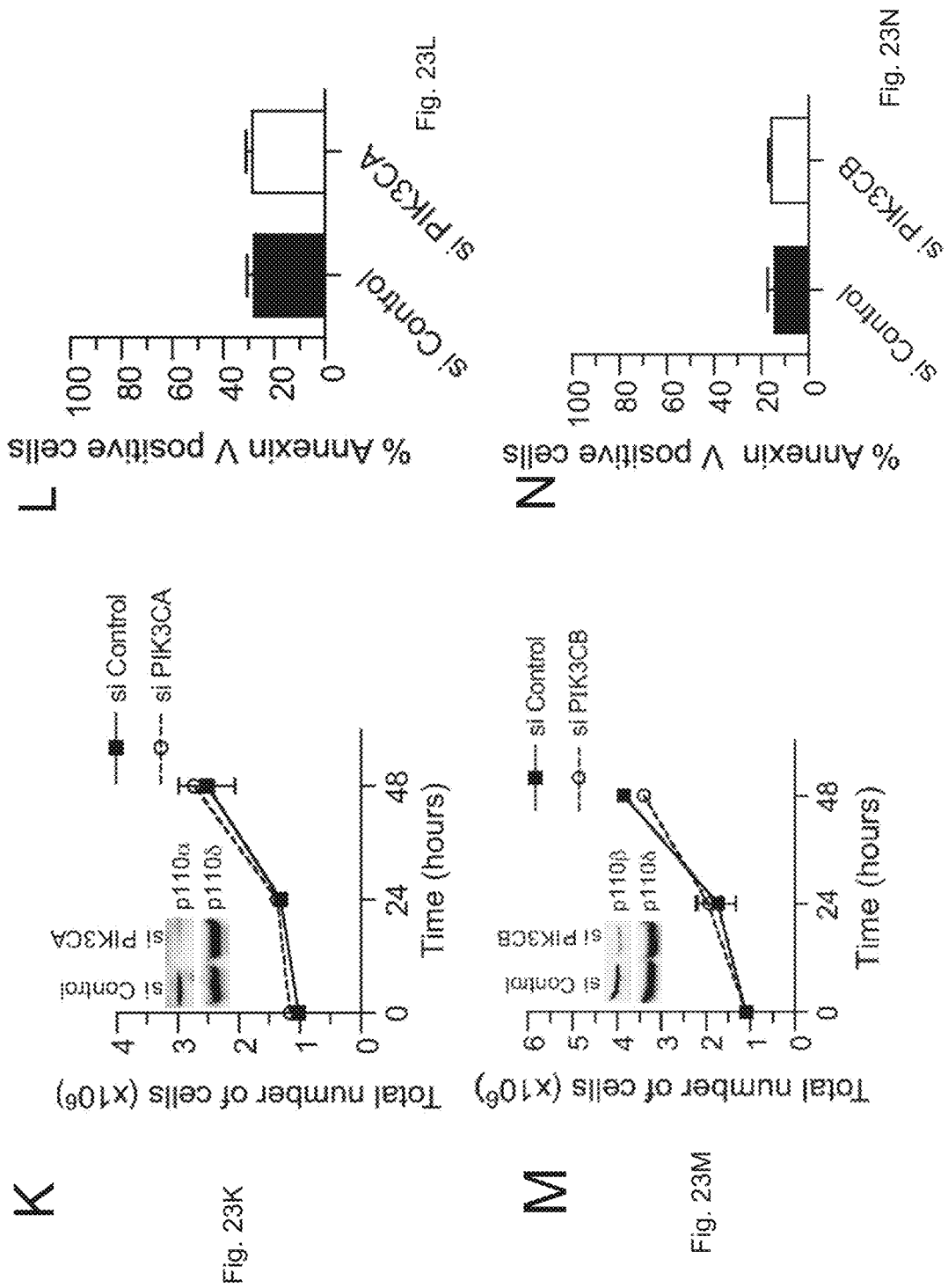

METHODS AND PHARMACEUTICAL COMPOSITIONS FOR TREATING LYMPHOID MALIGNANCY

CROSS-REFERENCE TO RELATED APPLICATIONS

The present application is a continuation of U.S. patent application Ser. No. 16/211,361, filed Dec. 6, 2018, which is a continuation of U.S. patent application Ser. No. 15/451, 306, filed Mar. 6, 2017, which is a continuation of U.S. patent application Ser. No. 14/003,873, filed Mar. 11, 2014, which is a U.S. national stage application of International Application No. PCT/US2012/027148, filed Feb. 29, 2012, which claims benefit to U.S. Provisional Application No. 61/450,341 filed Mar. 8, 2011, the entire contents of which are incorporated herein by reference in their entirety.

GOVERNMENT FUNDING

This invention was made with government support under grant no. W81XWH-10-1-0595 awarded by the ARMY/MRMC. The government has certain rights in the invention.

FIELD OF INVENTION

The present invention relates to, inter alia, methods and pharmaceutical compositions to treat, prevent, or ameliorate the effects of a lymphoid malignancy, such as T-cell acute lymphoblastic leukemia (T-ALL) or T-cell acute lymphoblastic lymphoma. Methods for identifying a subject who may benefit from co-treatment with a phosphoinositide 3-kinase-delta (PI3Kδ) inhibitor and a phosphoinositide 3-kinase-gamma (PI3Kγ) inhibitor and for identifying a compound that has both PI3Kδ and PI3Kγ inhibitory activity are also provided.

BACKGROUND OF THE INVENTION

Thymocyte development relies on a series of intracellular signaling events that regulate cell differentiation, proliferation, and survival. This process can be followed based on the presence or absence of cell surface markers such as CD4, CD8, CD25, and CD44 (Shortman et al.; 1996, Germain, 2002; Zuniga-Pflucker, 2004). Early thymocyte progenitors lack CD4 and CD8 expression and are termed double-negative (DN) cells. The DN stage is subdivided into 4 categories. The DN1 stage is characterized by surface expression of CD44 (CD25$^-$CD44$^+$). Maturation of this earliest thymocyte subset then proceeds from the DN2 stage (CD25$^+$CD44$^+$) to the DN3 stage (CD25$^+$CD44$^-$) and finally to the DN4 stage (CD25$^-$CD44$^-$). The first regulatory checkpoint in thymocyte development, termed β-selection, occurs at the DN3 stage. This involves T cell receptor β (TCRB) gene rearrangement and expression, which permits the subsequent formation of the pre-TCR complex (Dudley et al., 1994; Borowski et al., 2002). Thymocytes unable to generate a functionally rearranged TCRB gene die by apoptosis (Falk et al., 2001; Michie et al., 2002). Subsequently, signals provided by the pre-T cell receptor (pre-TCR) and local microenvironment result in the proliferation and differentiation of DN thymocytes to the CD4$^+$CD8$^+$ double positive (DP) stage. A small subset of these cells ultimately bear a mature TCRαβ$^-$CD3 complex and then further differentiate into CD4$^+$ or CD8$^+$ single-positive (SP) T cells.

In addition to TCRB selection, thymocyte development is also shaped by the induction or inhibition of apoptosis. Although many different molecules can regulate this process, the proto-oncogene Bcl-2 appears to have a protective effect with regard to thymocyte survival (Kroemer, 1997; Williams et al., 1998). This is supported by the observation that thymocytes in mice expressing a Bcl2 transgene are less prone to dexamethasone-induced cell death (Sentman et al., 1991; Strasser et al., 1991). Moreover, a strong correlation exists between Bcl-2 expression and sensitivity of specific thymocyte populations to apoptotic signals induced not only through stimulation of the TCR and coregulatory molecules, such as CD28, but also by cAMP and corticosteroids (McKean, 2001). For instance, most CD4$^+$CD8$^+$ DP thymocytes do not express Bcl-2, which may contribute to their relatively short lifespan of 3 to 4 days and to their increased sensitivity to various apoptotic stimuli, unlike their CD4$^+$ and CD8$^+$ SP counterparts (Gratiot-Deans et al., 1993; Linette et al., 1994; Punt et al., 1995). Thus, diminished Bcl-2 expression in DP cells appears to be the result of specific down-regulation, rendering these cells more amenable to thymic selection.

Class 1 phosphoinositide 3-kinases (PI3Ks) can also provide survival signals (Yao et al., 1995; Shelton et al., 2004). Structurally, they exist as heterodimeric complexes, consisting of a p110 catalytic (classified as α, β, γ, or δ) and a p50, p55, p85, or p101 regulatory subunit (Wymann et al., 1998; Vanhaesebroeck et al., 1997). These enzymes can be further divided into 2 subclasses (1a and 1b) based on their mechanism of activation. Class 1a contains p110α, p110β, and p110δ, each of which associates with a p85 regulatory protein and is activated directly or indirectly on engagement of several cell surface receptors, including TCR (Wymann et al., 1998; Vanhaesebroeck et al., 1997; Cantley et al., 2002). In contrast, class 1b consists solely of p110γ, which associates with the p101 adaptor molecule and is stimulated by G protein-coupled receptors. In either case, both subclasses transmit signals by generating a common second messenger known as phosphatidylinositol (3,4,5) trisphosphate (PIP3), which remains tethered to the lipid bilayer of the cell membrane. This results in the recruitment of the intracellular effector molecules PDK-1 and Akt/PBK that bind PIP3 through pleckstrin homology (PH) domains. Phosphorylation of Akt/PBK by PDK-1 results in its activation, which then affects cell survival by direct targeting of the proapoptotic proteins BAD and FoxO or by indirect influence on the transcriptional response to apoptotic stimuli (Franke et al., 2003; Downward, 2004). To date, limited information exists regarding the role of PI3K in thymocyte survival.

Evidence is mounting that class 1 PI3K may participate in thymocyte differentiation. For instance, mice lacking p110γ have reduced thymus size and cellularity and altered percentages of DN and DP thymocytes (Sasaki et al., 2000). Further characterization of this defect suggests partial impairment in pre-TCR-dependent DN-to-DP transition does not affect T-cell numbers in blood or secondary lymphoid organs (Rodriguez-Borlado et al., 2003). Moreover, no abnormalities were reported in TCR-mediated Ca$^{2+}$ flux, tyrosine phosphorylation, or activation of tyrosine kinases in T cells; results that have not been confirmed in thymocytes. T-cell sensitivity to typical apoptotic stimuli, such as γ irradiation or dexamethasone, also remained unaltered, although proliferation and IL-2 secretion were impaired. In contrast to p110γ$^{-/-}$ mice, the catalytic inactivation of p110δ did not perturb thymus size, cellularity, or thymocyte development but did impair antigen receptor signaling and proliferation of T cells in vitro (Okkenhaug et al., 2002). Similar observations were reported for genetic deletion of the p85 regulatory subunit, which affects the activity of all class 1a PI3Ks (Suzuki et al., 1999; Fruman et al., 1999). Thus, it appears that PI3Kδ is not required for thymic development. This may be the consequence of a lack of function, given that it is not known whether p110δ is expressed in developing thymocytes, or of residual PI3K activity due to other class 1a isoforms or perhaps by p110γ. Class 1a and 1b PI3Ks work in concert to regulate specific cellular processes. In particular, a deficiency in p110γ and p110δ catalytic subunits in venular endothelium had an additive effect in terms of the ability of this cell type to recruit neutrophils in response to cytokine stimulation (Puri et al., 2005).

Constitutive activation of the PI3K/Akt signal transduction pathway is a common event in cancer, promoting the growth, proliferation, and survival of various types of tumors including T-cell acute lymphoblastic leukemia (T-ALL) (Yuan and Cantley, 2008; Zhao and Vogt, 2008; Gutierrez et al., 2009; Palomero et al., 2008; Silva et al., 2008; Larson Gedman et al., 2009). As set forth above, class I PI3Ks are heterodimeric molecules composed of a regulatory and a catalytic subunit, the latter consisting of four unique isoforms that include p110α, p110β, p110γ, and p110δ. Each is capable of regulating distinct biological functions in normal tissues and cellular compartments. However, some overlap in activity does exist, as is the case for thymocytes where the combined activities of PI3Kγ and PI3Kδ contribute to cellular processes required for the generation and function of mature T cells (Webb et al., 2005; Swat et al., 2006; Ji et al., 2007). It is not clear, what role, if any, PI3Kγ and PI3Kδ play in malignant transformation and tumor cell survival.

Previously, it has been reported that p110α is involved in oncogenesis, because function-enhancing mutations in this catalytic subunit are found in many cancers of solid organs (Samuels et al., 2004; Zunder et al., 2008). In contrast, cancer-specific mutations have yet to be identified for the other p110 isoforms. That said, over-expression of p110δ, p110γ, or p110δ in an in vitro culture system induces cellular transformation (Kang et al., 2006). Moreover, increased or preferential expression of p110γ and p110δ has been described in chronic and acute forms of myeloid leukemia, respectively (Hickey and Cotter, 2005; Sujobert et al., 2005). However, over-expression of specific PI3K isoforms has not been reported for T-ALL and mutations in PI3Kα are rare, thus suggesting that they are not a major contributor to pathogenesis (Gutierrez et al., 2009; Lo et al., 2009).

PTEN is a nonredundant plasma-membrane phosphatase that is responsible for counteracting the potential cancer-promoting activities of class I PI3K (Sulis and Parsons, 2003; Salmena et al., 2008). It does so by limiting the levels of PIP3 generated in response to the activation of these lipid kinases. Clinically, mutations in the Pten tumor suppressor gene are common in multiple types of human cancer, resulting in unbridled PI3K/Akt signaling as well as conferring resistance to chemotherapeutic agents (Carnero et al., 2008; Huang et al., 2009). In fact, Gutierrez et al. (2009) have reported a loss of PTEN function due to mutations or deletions in approximately 40% of primary T-ALL samples, suggesting that hyperactivation of the PI3K/Akt signaling pathway is a common feature of this hematological malignancy.

Accordingly, there is a need to determine whether these non-classical oncogenes contribute to leukemogenesis and whether it is possible to exploit tumor cell "addiction" to the activity of distinct PI3K isoforms, thus permitting the rational design of a chemotherapeutic agent to treat T-ALL. This invention is directed to meeting these and other needs.

SUMMARY OF THE INVENTION

One embodiment of the present invention is a method for treating, preventing, or ameliorating the effects of a lymphoid malignancy. This method comprises administering to a subject in need thereof an effective amount of a phosphoinositide 3-kinase-delta (PI3Kδ) inhibitor and a phosphoinositide 3-kinase-gamma (PI3Kγ) inhibitor.

Another embodiment of the present invention is a method for treating, preventing, or ameliorating the effects of a lymphoid malignancy associated with a mutated phosphatase and tensin homolog (PTEN) gene in a subject. This method comprises administering to the subject an effective amount of a PI3Kδ inhibitor and a PI3Kγ inhibitor.

Yet another embodiment of the present invention is a pharmaceutical composition for treating the effects of a lymphoid malignancy. This pharmaceutical composition comprises a pharmaceutically acceptable carrier and an effective amount of a PI3Kδ inhibitor and a PI3Kγ inhibitor.

An additional embodiment of the present invention is a method for treating a subject suffering from T-ALL. This method comprises administering to the subject an effective amount of a pharmaceutical composition comprising a PI3Kδ inhibitor and a PI3Kγ inhibitor.

Another embodiment of the present invention is a method for lowering tumor burden in a subject suffering from T-ALL. This method comprises administering to the subject an effective amount of a pharmaceutical composition comprising a PI3Kδ inhibitor and a PI3Kγ inhibitor.

Yet another embodiment of the present invention is a method for identifying a subject who may benefit from co-treatment with a PI3Kδ inhibitor and a PI3Kγ inhibitor. This method comprises determining from a sample of the subject whether the subject has a mutated PTEN gene, wherein the presence of the mutated PTEN gene is indicative of a subject who may benefit from co-treatment with a PI3Kδ inhibitor and a PI3Kγ inhibitor.

An additional embodiment of the present invention is a method for identifying a compound that has both PI3Kδ and PI3Kγ inhibitory activity. This method comprises:

(a) contacting a cell with the compound; and
(b) determining whether the compound modulates an antigen receptor-induced activity in the cell;

wherein a compound that modulates the antigen receptor-induced activity has both PI3Kδ and PI3Kγ inhibitory activity.

BRIEF DESCRIPTION OF THE DRAWINGS

FIGS. 2A-2E show the role of PI3Kδ and PI3Kγ in thymocyte development. Flow cytometry analysis of expression of various markers are shown: CD4 and CD8 on total thymocyte population (FIG. 2A), CD25 and CD44 on DN thymocytes (FIG. 2B), intracellular TCRB in $CD25^+$ DN thymocytes (FIG. 2C), and TCRB on the surfaces of DP (FIG. 2D) and $CD8^+$ (FIG. 2E) thymocytes. Percentage of gated cells in a particular quadrant is indicated. Data are representative of 3 independent experiments. Total thymocyte counts are in bold (mean±SE; n=5).

FIG. 3A shows representative flow cytometry profiles of fetal thymic organ cultures harvested from day 14.5 WT, $p110δ^{-/-}$, and $p110γ^{-/-}$ embryos that were treated with either vehicle control or p110δ-specific inhibitor IC87114 (10 μM) for 1 week. FIG. 3B shows the percentage reduction in DP thymocyte population after treatment with IC87114 compared with control treatment (mean±SE; n=3).

FIG. 4A shows representative flow cytometry profiles of annexin V staining of the $PI^-$ population of DP thymocytes live-gated from WT control and $p110γ^{-/-}$ mice (n=3). PI staining of the live-gated population of thymocytes was performed first to identify and thus exclude necrotic cells as defined by forward- and side-scatter parameters. Gates in the $CD4^+$ and $CD8^+$ panels indicate the DP thymocyte population gated for analysis of annexin V staining (histogram, which was exclusive of the $PI^+$ staining, as stated). FIG. 4B shows density plots of DP thymocytes harvested from WT control and $p110γ^{-/-}$ mice after treatment with BrdU. Representative histograms depict the percentages of DP cells that stained with BrdU (n=3 for each group).

FIG. 5A shows representative immunoblots of class 1a and 1b p110 subunits expressed in thymocytes harvested from WT control and $p110γ^{-/-}$ mice. Western blot of β-actin illustrates equal loading of proteins. FIG. 5B shows the detection of Akt/PKB in Western blots of total lysates from $p110γ^{-/-}$ thymocytes treated with vehicle control or the p110δ-specific inhibitor IC87114 (10 μM) before TCR cross-linking. (C) $Ca^{2+}$ flux in $CD4^+$-gated thymocytes in WT control, $p110γ^{-/-}$, $p110δ^{-/-}$, and $p110γ^{-/-}$ mice in response to TCR cross-linking. $Ca^{2+}$ flux in $CD4^+$ $CD8^+$-sorted thymocytes from WT control and $p110γ^{-/-}$ animals is shown for comparison (inset). Data are representative of 3 to 4 separate experiments.

FIGS. 6A-6E show the effect of p110δ and p110γ deletion on extrathymic T cells. FIG. 6A shows cell counts and flow cytometry analysis of surface expression of TCRB, which were performed on whole blood and isolated peripheral blood mononuclear cells (PBMCs), respectively. CD4 and CD8 expression was evaluated on total cells harvested from peripheral lymph nodes (FIG. 6B) and spleens (FIG. 6C) of WT control and $p110γδ^{-/-}$. FIGS. 6B and 6C show histologic examination of hematoxylin and eosin-stained lymph node and splenic sections, respectively (objective magnifications each 4×). Delineation of the T-cell population by immunoperoxidase detection of $CD3^+$ counterstained with Meyer hematoxylin was also performed (100×; scale bar, 100 μm). $Ca^{2+}$ flux in $CD4^+$-gated T cells from WT control (FIGS. 6D-E), $p110γ^{-/-}$ (FIG. 6E), $p110δ^{-/-}$ (FIG. 6E), and $p110γ^{-/-}$ (FIGS. 6D-E) mice in response to TCR cross-linking. Values depicted represent the mean±SE for 3 independent experiments performed in duplicate or triplicate. *Statistical significance compared with WT control ($P<0.05$).

FIGS. 7A-7E show that absence of p110γ or p110δ alone has no apparent effect on the percentage of DP thymocytes or TCR-selection. FIG. 7A shows thymic size and architecture in four week old WT, $p110γ^{-/-}$, and $p110δ^{-/-}$ mice. Histological examination of H&E stained thymic sections from these animals are shown. Data are representative of a minimum of three animals for each genetic background. FIGS. 7B-E show representative flow cytometric analysis of expression of CD4 and CD8 SP and DP thymocytes (FIG. 7B), DN (FIG. 7C), and TCRB+ DP (FIG. 7D) and $CD8^+$ SP subsets (FIG. 7E). Data are representative of three independent experiments.

FIG. 10A shows the thymocyte population expression of CD4 and CD8 as determined by flow cytometry. Percent expression is in bold. FIG. 10B shows the total double positive (CD4/CD8 expressing) cell count (mean±SD). Data indicates an average of 4 independent experiments.

FIG. 12A shows a representative histogram of a CD3 population in peripheral blood. FIG. 12B shows the percent CD3 population in peripheral blood. Data indicates 4 independent experiments.

FIGS. 14A-14D show that PI3Kγ or PI3Kδ can support leukemogenesis in the context of PTEN deficiency. FIG. 14A shows Kaplan-Meyer survival curves demonstrating the requirement for PI3Kγ and PI3Kδ activity in the development of PTEN-null T-ALL. TKO indicates Lck/Pten$^{fl/fl}$; Pik3cg$^{-/-}$; pik3cd$^{-/-}$ triple mutant mice. All animals were followed for a period of 7 months. FIG. 14B shows representative flow cytometric profiles of peripheral blood from diseased mice lacking p110γ or p110δ in the absence of PTEN in T cell progenitors. Forward scatter (FSC) and Ki67 staining are indicators of cell size and proliferation, respectively. Thy 1.2 expression identifies T-lineage cells. FIG. 14C shows representative immunoblots depicting p110γ, p110δ, and PTEN expression as well as Akt activation state (phosphorylation of Ser473) in thymic lysates from the same animals. FIG. 14D shows a quantitative RT-PCR analysis of Pik3c (a/b/g/d) transcript levels in WT thymocytes (n=5) and tumors (n=5) harvested from Lck/Pten$^{fl/fl}$ mice. Error bars represent the standard deviation (±SD). The difference in Pik3C expression levels between the WT thymocytes and tumor cells were statistically significant (*P<0.05) using a Student's test.

FIG. 15A shows hematoxylin/eosin (H&E) staining and flow cytometric analyses of thymi derived from 6 week old mice lacking both p110γ and p110δ catalytic subunits in the presence or absence of PTEN. The panels are representative of data from five animals in each group. FIG. 15B shows immunoblots assessing for Akt phosphorylation (Ser473) and PTEN levels in thymocyte lysates. FIG. 15C shows the number of WBC and T cell subsets in the peripheral blood of the same animals. Data represent the mean±SD. *P>0.05 for Pik3cg$^{-/-}$; pik3cd$^{-/-}$ versus TKO **P<0.01 for WT versus TKO. FIG. 15D shows representative micrographs of H&E-stained peripheral lymph nodes and spleen, and FIG. 15E shows representative flow cytometry plots of blood and spleen from triple mutant animals. (n=5 mice per genotype). Histological identification of T cells was by immunoperoxidase detection of CD3. Bars correspond to 200 μm in secondary lymphoid organs and to 500 μm in thymi. Data represent the mean±SD.

FIGS. 16A-16H show the inhibitory profile of CAL-130. FIG. 16A shows the chemical structure of CAL-130. FIGS. 16B and 16C show the effect of the inhibitor on Akt phosphorylation (Ser473) or Ca$^{2+}$ flux in purified thymocytes from wild type animals in response to TCR cross-linking, respectively. Data are representative of 3 separate experiments. FIG. 16D shows plasma concentrations of CAL-130 in mice after a single oral dose (n=4). FIGS. 16E and 16F show the plasma glucose and the corresponding insulin levels, respectively, in wild type mice before and after receiving a single dose of inhibitor (10 mg kg$^{-1}$). P>0.5 for glucose and P >0.2 for insulin as compared to baseline (ns=not significant; n=15 mice per time point). FIG. 16G shows the phenotypic analyses of thymi from mice treated with either CAL-130 (10 mg kg$^{-1}$ every 8 hours) or vehicle control for 7 days. The panels are representative of data from five animals in each group. FIG. 16H shows total DP thymocyte count in the same animals. Results are compared to PI3Kγ/δ double knockout mice. Data represent the mean±SD.

FIG. 17A shows a Kaplan-Meyer survival curve for Lck/Pten$^{fl/fl}$ mice diagnosed with T-ALL and immediately treated with CAL-130 for a total of 7 days. P<0.001 for CAL-130 treated versus vehicle control. *Numbers represent the initial WBC (×10$^6$) for each animal prior to instituting therapy. FIGS. 17B and 17C show peripheral blood smears and flow cytometric profiles for diseased Lck/Pten$^{fl/fl}$ and Lck/Pten$^{fl/fl}$; Pik3cg$^{-/-}$ mice, respectively, just before treatment (day 0) and 4 days and 7 days after initiating treatment with either CAL-130 or the PI3Kγ specific inhibitor IC87114, respectively. The panels are representative of data from four Lck/Pten$^{fl/fl}$ mice and two Lck/Pten$^{fl/dl}$ Pik3d$^{-/-}$ mice with T-ALL. An untreated wild type animal is shown for comparison. FIG. 17D shows bioluminescent images and corresponding flow cytometric profiles of Lck/PTEN$^{fl/fl}$/Gt(ROSA)26Sor$^{tm1(Luc)Kael}$/j animals with T-ALL immediately before and 4 days after treatment. FIG. 17E shows weights of thymi, liver, spleen, and kidneys harvested from Lck/Pten$^{fl/fl}$ mice with T-ALL 7 days post-treatment with either CAL-130 or vehicle control (n=5, *P<0.01 for CAL-130 treated versus vehicle control). Peripheral blood counts (WBC, right axis) represent the mean±SD prior to treatment.

FIGS. 18A-18H show that PI3Kγ and PI3Kδ contribute to the growth and survival of PTEN null human T-ALL tumor cell lines. FIGS. 18A and 18B show the proliferation and survival, respectively, of CCRF-CEM cells cultured in the presence of CAL-130 or vehicle control. *P<0.01, **P<0.001 for CAL-130 treated (2.5 μM) versus DMSO. FIGS. 18E and 18F show proliferation and survival, respectively, of CCRF-CEM cells cultured in the presence of dexamethasone alone. FIGS. 18G and 18H show proliferation and survival, respectively, of CCRF-CEM cells cultured in the presence of dexamethasone in combination with 2.5 μM CAL-130. P<0.001 for dexamethasone+CAL-130 treated (2.5 μM) versus CAL-130 (2.5 μM) alone. Data represent the mean±SD of experiments performed in triplicate.

FIGS. 19A-19D show the effect of CAL-130 on signaling pathways downstream of PI3Kγ and PI3Kδ. FIG. 19A shows representative immunoblots of lysates obtained from CCRF-CEM cells treated for 6 hours with either CAL-130 or vehicle control and probed with the stated antibodies. The PI3Kγ specific inhibitor IC87114 (IC) is shown for comparison. FIG. 19B shows representative immunoblots demonstrating activation of the pro-apoptotic pathway in CAL-130 treated CCRF-CEM cells. FIG. 19C shows representative bioluminescence images (upper panel) and quantification of tumor mass changes (lower panel) in mice with subcutaneous CCRF-CEM xenografts that received vehicle control or CAL-130 for 4 days (n=7). FIG. 19D shows Kaplan-Meyer analysis of overall survival of mice treated with vehicle control or CAL-130 for 7 days in a systemic CCRF-CEM xenograft model (P<0.01 for CAL-130 treated versus vehicle control; n=7 per group).

FIGS. 20A-20D show the susceptibility of primary human T-ALL tumor cells to combined inhibition of p110γ and p110δ. FIG. 20A shows cell survival analyses of tumors cultured in the presence of increasing concentrations of CAL-130 for 72 hours. Percent viability indicates the proportion of live-gated cells in the treated populations relative to its vehicle control counterpart. Data represent the mean±SD of experiments performed in duplicate or triplicate. *P<0.01, **P<0.001 for CAL-130 treated versus DMSO control. nd=not done and ns=not significant.

FIG. 20B shows representative immunoblots of four primary human T-ALL samples to assess for expression of p110 catalytic domains and PTEN as well as phosphorylation state of Akt. FIG. 20C shows the effect of CAL-130 on Akt phosphorylation on the same four representative T-ALL samples after 6 hours of treatment. Densitometry was performed on bands from immunoblots. The P-Akt signal was normalized to total Akt. FIG. 20D shows a quantitative RT-PCR analysis of PIK3C (A/B/G/D) transcript levels in human thymocytes (n=5) and primary human T-ALL tumors (n=5). Error bars represent the standard deviation (±SD). The difference in PIK3C expression levels between the thymocytes and tumor cells was not statistically significant (P>0.05) using a Student's t-test.

FIG. 21A shows $Ca^{2+}$ flux in $CD4^+$-gated wild type versus $PI3K\delta^{ko/\delta ko}$ thymocytes treated with vehicle control or CAL-130 prior to TCR cross-linking. Data represent the mean±SD (3 separate experiments for each genotype). FIG. 21B shows the effect of CAL-130 versus the pan-PI3K/mTor inhibitor BEZ235 on Akt phosphorylation in response to PDGF-stimulation of SW3T3 cells. FIG. 21C shows the effects of CAL-130 on ADP (25 µM)-induced aggregation of platelets harvested from $pik3cg^{-/-}$; $pik3cd^{-/-}$ mice. CAL-130 was either directly added to purified platelets (upper panel) or given as an oral bolus to animals (lower panel) prior to harvesting platelets at a time point that yields a maximum plasma level of compound (2 hours).

FIGS. 23A-23N show the contribution of PI3Kγ and PI3Kδ to the growth and survival of PTEN null human T-ALL tumor cell lines. FIGS. 23A-D show the proliferation of CCRF-CEM, and FIGS. 23E-H show the proliferation of MOLT-4 cells cultured in the presence of the indicated class I PI3K inhibitors. Annexin V staining of CCRF-CEM cells (FIG. 23I) and MOLT-4 cells (FIG. 23J) cultured in the presence of the indicated class I PI3K inhibitors at 72 hours. Data represent the mean±SD of 4 independent experiments. *$P<0.004$. ns=not significant. FIGS. 23K and L show siRNA knockdown of p110α in CCRF-CEM cells. FIGS. 23M and N show siRNA knockdown of p110β in CCRF-CEM cells. Cell growth and viability were determined by cell counting (FIGS. 23K and M) and Annexin V staining (FIGS. 23L and N), respectively. Inserts are immunoblots for (FIG. 23K) p110α and (FIG. 23M) p110β. Data are representative of four independent experiments (mean±SD).

DETAILED DESCRIPTION OF THE INVENTION

Figure 1:
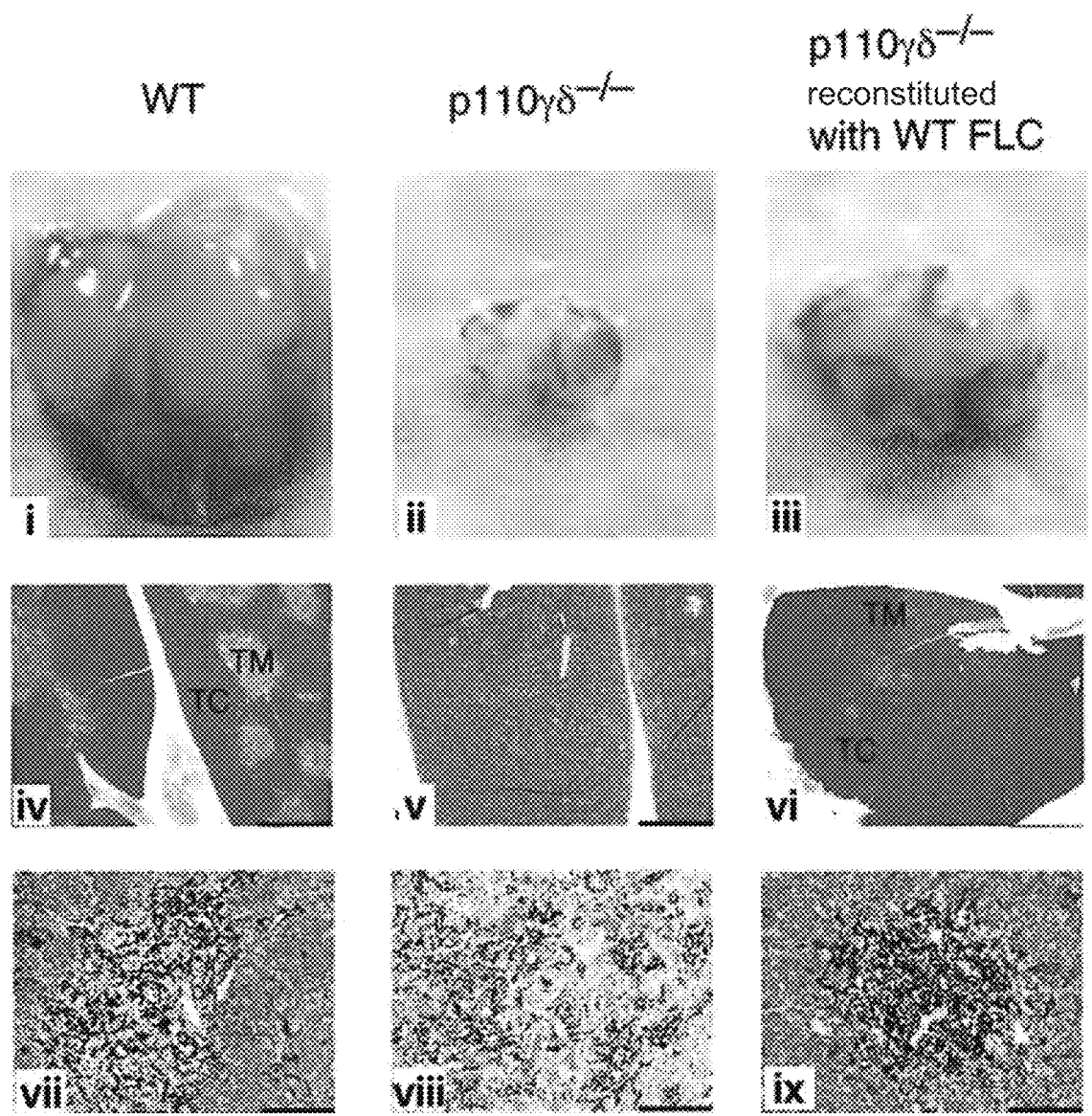
FIG. 1 shows the role of class 1 PI3Ks in supporting thymic architecture and cellularity. Representative micrographs depicting thymus size and hematoxylin and eosin-stained sections from wildtype (WT) control (i,iv) and p110γ$^{-/-}$ (ii,v) mice and from p110γ$^{-/-}$ animals reconstituted with WT fetal liver cells (iii,vi). Delineation of the thymic medulla in these animals (vii-ix) was performed by immunoperoxidase detection of Keratin5$^+$ epithelial cells counterstained with Meyer hematoxylin. Cortical and medullary regions in the thymus of p110γ$^{-/-}$ mice are indistinguishable, unlike those of WT and reconstituted animals. (Objective, magnification 40×4×/numerical aperture ("NA") 0.16) in panels iv to vi (scale bar, 500 μm) and 200× (objective, 20×/0.7 NA) in panels vii to ix (scale bar, 100 μm). TC indicates thymic cortex; TM, thymic medulla. Data are representative of at least 3 animals for each genotype depicted.

One embodiment of the present invention is a method for treating, preventing, or ameliorating the effects of a lymphoid malignancy. This method comprises administering to a subject in need thereof an effective amount of a PI3Kδ inhibitor and a PI3Kγ inhibitor.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, the terms "prevent", "preventing" and grammatical variations thereof mean to administer a compound or a composition of the present invention to a subject who has not been diagnosed as having the disease or condition at the time of administration, but who could be expected to develop the disease or condition or be at increased risk for the disease or condition. Preventing also includes administration of at least one compound or a composition of the present invention to those subjects thought to be predisposed to the disease or condition due to age, familial history, genetic or chromosomal abnormalities, due to the presence of one or more biological markers for the disease or condition and/or due to environmental factors.

As used herein, a "subject" is a mammal, preferably, a human. In addition to humans, categories of mammals within the scope of the present invention include, for example, agricultural animals, domestic animals, laboratory animals, etc. Some examples of agricultural animals include cows, pigs, horses, goats, etc. Some examples of domestic animals include dogs, cats, etc. Some examples of laboratory animals include rats, mice, rabbits, guinea pigs, etc.

As used herein, a "lymphoid malignancy" means an abnormal growth of bodily tissue or cells in the lymphoid system. Such abnormal growth may invade and destroy nearby tissue, and may spread to other parts of the body. The term "lymphoid system" refers to all of the cells, tissue aggregates, and organs which function together to produce specific resistance to disease, including without limitation, the bone marrow, the thymus, lymphatic vessels, T-cells and their progenitor cells, as well as B-cells and their progenitor cells.

Lymphoid malignancies may be divided into three classes, Hodgkin's lymphoma, non-Hodgkin's lymphoma (NHL), and composite Hodgkin's lymphoma and NHL. Hodgkin's lymphoma include lymphocyte-rich classical Hodgkin's lymphoma, mixed-cellularity classical Hodgkin's lymphoma, lymphocyte-depleted classical Hodgkin's lymphoma, and nodular lymphocyte predominant Hodgkin's lymphoma. NHL may be further divided into B-cell NHL, T-cell NHL, and NHL of unknown lineage. Exemplary B-cell NHL include without limitation precursor B-cell NHL (such as B lymphoblastic leukemia and B lymphoblastic lymphoma), chronic lymphocytic leukemia, small lymphocytic lymphoma, prolymphocytic leukemia, mantel-cell lymphoma, lymphoplasmacytic lymphoma, Waldenström macroglobulinemia, Burkitt lymphoma, follicular lymphoma, splenic marginal-zone lymphoma, extranodal marginal-zone lymphoma, nodal marginal-zone lymphoma, hairy-cell leukemia, diffuse large B-cell lymphoma, intravascular large B-cell lymphoma, primary effusion lymphoma, mediastinal large B-cell lymphoma, plasmacytoma, and multiple myeloma/plasma cell leukemia. T-cell NHL include precursor T-cell NHL (such as T-cell acute lymphoblastic leukemia (T-ALL) and T-cell acute lymphoblastic lymphoma), mycosis fungoides, Sezary syndrome, adult T-cell leukemia, adult T-cell lymphoma, NK/T-cell lymphoma, aggressive NK-cell leukemia, T-cell large granular lymphocytic leukemia, T-cell prolymphocytic leukemia, and peripheral T-cell lymphoma (such as angioimmunoblastic lymphoma, subcutaneous panniculitis-like T-cell lymphoma, anaplastic large-cell lymphoma, hepatoplenic T-cell lymphoma, enteropathy-type T-cell lymphoma, cutaneous T-cell lymphoma, primary cutaneous anaplastic large-cell lymphoma). Preferably, the lymphoid malignancy is T-ALL or T-cell acute lymphoblastic lymphoma. In another preferred embodiment, wherein the lymphoid malignancy is T-ALL.

As used herein, a "PI3Kδ inhibitor" is an agent that is able to lower the activity level or the expression level of PI3Kδ. Preferably, the PI3Kδ inhibitor has few or no off-target effects; except that it is permissible, in accordance with the present invention, to also have an inhibitory effect on PI3Kγ as set forth in more detail below. The PI3Kδ inhibitor according to the present invention may be a biologic, a chemical, or combinations thereof. PI3Kδ inhibitors include, without limitation, AMG-319 (Amgen, Thousand Oaks, CA); PI3-delta inhibitors, Cellzome (Cellzome AG, Heidelberg, Germany); PI3-delta/gamma inhibitors, Cellzome (Cellzome AG); CHR-4432 (Chroma Therapeutics, Ltd., Abingdon, UK); XL-499 (Evotech, Hamburg, Germany); CAL-120 (Gilead Sciences, Foster City, CA); CAL-129 (Gilead Sciences); CAL-130 (Gilead Sciences); CAL-253 (Gilead Sciences); CAL-263 (Gilead Sciences); GS-1101 (CAL-101) (Gilead Sciences); benzimidazole series, Genentech (Roche Holdings Inc., South San Francisco, CA); PI3 kinase delta inhibitors, Genentech (Roche Holdings Inc.); PI3 kinase inhibitor, Roche-4 (Roche Holdings Inc.); PI3 kinase inhibitors, Roche (Roche Holdings Inc.); PI3 kinase inhibitors, Roche-5 (Roche Holdings Inc.); pictilisib (Roche Holdings Inc.); PI3 kinase delta inhibitors, Incozen (Incozen Therapeutics, Pvt. Ltd., Hydrabad, India); PI3 kinase delta inhibitors-2, Incozen (Incozen Therapeutics); PI3-delta inhibitors, Intellikine (Intellikine Inc., La Jolla, CA); PI3-delta/gamma inhibitors, Intellikine (Intellikine Inc.); PI3K delta/gamma inhibitors, Intellikine-1 (Intellikine Inc.); KAR-4139 (Karus Therapeutics, Chilworth, UK); KAR-4141 (Karus Therapeutics); PI3 kinase delta inhibitor, Merck KGaA (Merck & Co., Whitehouse Station, NJ); OXY-111A (NormOxys Inc., Brighton, MA); PI3-alpha/delta inhibitors, Pathway Therapeutics (Pathway Therapeutics Ltd., South San Francisco, CA); PI3-delta inhibitors, Pathway Therapeutics-1 (Pathway Therapeutics Ltd.); PI3-delta inhibitors, Pathway Therapeutics-2 (Pathway Therapeutics Ltd.); PI3-delta/gamma inhibitors, Pathway Therapeutics (Pathway Therapeutics Ltd.); SF-1126 (Semafore Pharmaceuticals, Indianapolis, IN); X-339 (Xcovery, West Palm Beach, FL); IC87114 (Gilead Science); TG100-115 (Targegen Inc., San Diego, CA); and combinations thereof. Preferably, the PI3Kδ inhibitor is CAL-130. PI3Kδ inhibitor may also be a nucleic acid comprising an shRNA or an siRNA, preferably an shRNA.

As used herein, a "biologic" means a substance which is derived from or produced by a living organism or synthesized to mimic an in vivo-derived agent or a derivative or product thereof. A biologic may be, for example, a nucleic acid, a polypeptide, or a polysaccharide. Preferably, the biologic is a nucleic acid, a protein, or a combination thereof. More preferably, the nucleic acid comprises an shRNA.

As used herein, a "chemical" means a substance that has a definite chemical composition and characteristic properties and that is not a biologic. Non-limiting examples of chemicals include small organic compounds and small inorganic compounds.

As used herein, a "PI3Kγ inhibitor" is an agent that is able to lower the activity level or the expression level of PI3Kγ. Preferably, the PI3Kγ inhibitor has few or no off-target effects; except that it is permissible, in accordance with the present invention, to also have an inhibitory effect on PI3Kδ as set forth in more detail above. The PI3Kγ inhibitor according to the present invention may be a biologic, a chemical, and combinations thereof. PI3Kγ inhibitors include, without limitation, PI3-delta/gamma inhibitors, Cellzome (Cellzome AG); PI3-gamma inhibitor, Cellzome (Cellzome AG); PI3-gamma inhibitor Evotec (Evotec); PI3 kinase inhibitors, Roche (Roche Holdings Inc.); pictilisib (Roche Holdings, Inc.); IPI-145 (Intellikine Inc.); PI3-delta/gamma inhibitors, Intellikine (Intellikine Inc.); PI3K delta/gamma inhibitors, Intellikine-1 (Intellikine Inc.); KIN-1 (Karus Therapeutics); PI3-delta/gamma inhibitors, Pathway Therapeutics (Pathway Therapeutics Ltd.); PI3-gamma inhibitors, Pathway Therapeutics (Pathway Therapeutics Ltd.); SC-103980 (Pfizer, New York, NY); SF-1126 (Semafore Pharmaceuticals); AS-041164 (5-benzo[1,3]dioxol-5-ylmethylene-thiazolidine-2,4-dione); AS-604850 (5-(2,2-Difluoro-benzo[1,3]dioxol-5-ylmethylene)-thiazolidine-2,4-dione); TG100-115 (Targegen Inc., San Diego, CA); AS-605240 (5-quinoxilin-6-methylene-1,3-thiazolidine-2,4-dione); CAL-130 (Gilead Sciences); and combinations thereof. Preferably, the PI3Kγ inhibitor is CAL-130. PI3Kγ inhibitor may also be a nucleic acid comprising an shRNA or an siRNA, preferably an shRNA.

In the present invention, a single agent that inhibits both PI3Kδ and PI3Kγ, but has no or limited effect on other PI3K isoforms, is also contemplated. Non-limiting examples of such an agent having dual inhibitory function include CAL-130; TG100-115; PI3-delta/gamma inhibitors, Cellzome; PI3 Kinase inhibitors, Roche-5; pictilisib; PI3-delta/gamma inhibitors, Intellikine; PI3-delta/gamma inhibitors, Intellikine-1; PI3-delta/gamma inhibitors, Pathway Therapeutics, and SF-1126. As disclosed previously, the present invention also includes co-treatment with one or more PI3Kδ and one or more PI3Kγ inhibitors. Such co-treatment may be by co-administration of each inhibitor or administration of one inhibitor followed by another inhibitor with each such administration being temporally spaced apart to achieve a clinically effective result. Determination of such dosing regimens may be determined empirically for each subject or be based on the treating physicians' knowledge and experience.

In one aspect of this embodiment, this method further comprises co-administering to the subject at least one chemotherapeutic agent. Such chemotherapeutic agent includes, without limitation, actinomycin, amsacrine, anthracycline, busulfan, cisplatin, cytoxan, epirubicin, hexamethylmelamineoxaliplatin, iphosphamide, mitoxantrone, taxotere, teniposide, triethylenethiophosphoramide, hydrocortisone, cortisone, methylprednisolone, prednisolone, dexamethasone, prednisone, betamethasone, triamcinolone, beclometasone, fludrocortisones, deoxycorticosterone, aldosterone, oxaliplatin, zoledronic acid, ibandronate, verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin, methotrexate, L-asparaginase, rapamycin, dibenzazepine (DBZ), uramustine, carmustine, lomustine, streptozocin, temozolomide, oxaliplatin, idarubicin, topotecan, premetrexed, 6-mercaptopurine, darcarbazine, fludarabine, 5-fluorouracil, arabinosycytosine, 5-fluorouracil, arabinosylcytosine, capecitabine, gemcitabine, decitabine, vinca alkaloids, paclitaxel (Taxol®), docetaxel (Taxotere®), ixabepilone (Ixempra®), and combinations thereof. Preferably, the chemotherapeutic agent is a glucocorticoid, such as hydrocortisone, cortisone, methylprednisolone, prednisolone, dexamethasone, prednisone, betamethasone, triamcinolone, beclometasone, fludrocortisones, deoxycorticosterone, aldosterone, and combinations thereof. In a preferred embodiment, the chemotherapeutic agent is dexamethasone.

In the present invention, one or more PI3Kδ and/or PI3Kγ inhibitors and/or one or more chemotherapeutic agents may be co-administered to a subject in need thereof together in the same composition, simultaneously in separate compositions, or as separate compositions administered at different times, as deemed most appropriate by a physician.

In the present invention, an "effective amount" or "therapeutically effective amount" of a PI3K inhibitor, whether a PI3Kγ inhibitor or a PI3Kδ inhibitor, is an amount of such an inhibitor that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a PI3K inhibitor according to the invention will be that amount of the PI3K inhibitor, which is the lowest dose effective to produce the desired effect with no or minimal side effects. The effective dose of a PI3Kγ inhibitor or a PI3Kδ inhibitor may be administered as two, three, four, five, six or more sub-doses, administered separately at appropriate intervals throughout the day, with the proviso that the doses of the PI3Kγ inhibitor or a PI3Kδ inhibitor simultaneously reduce or inhibit the activity or the expression levels of PI3Kγ and PI3Kδ.

A suitable, non-limiting example of a dosage of a PI3K inhibitor according to the present invention, particularly a PI3Kγ inhibitor and/or a PI3Kδ inhibitor, is from about 1 ng/kg to about 1000 mg/kg, such as from about 1 mg/kg to about 100 mg/kg, including from about 5 mg/kg to about 50 mg/kg. Other representative dosages of a PI3K inhibitor include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

Another embodiment of the present invention is a method for treating, preventing, or ameliorating the effects of a lymphoid malignancy associated with a mutated phosphatase and tensin homolog (PTEN) gene in a subject. This method comprises administering to the subject an effective amount of a PI3Kδ inhibitor and a PI3Kγ inhibitor.

As used herein, a "mutated phosphatase and tensin homolog (PTEN) gene" means having one or more variations in the exon or the intron sequence of PTEN. A lymphoid malignancy "associated with a mutated PTEN gene" means a lymphoid malignancy in which one or more variations in the PTEN gene sequence is found. Such lymphoid malignancies include, e.g., T-ALL, lymphoblastic lymphoma, large B-cell lymphoma, Burkitt's lymphoma, large B-cell lymphoma, and myeloma.

The PI3Kδ inhibitor and the PI3Kγ inhibitor are as disclosed herein. Preferably, the PI3Kδ inhibitor and the PI3Kγ inhibitor are CAL-130.

In one aspect of this embodiment, the method further comprises administering an effective amount of a chemotherapeutic agent as disclosed herein, such as a glucocorticoid. Preferably, the chemotherapeutic agent is dexamethasone.

Yet another embodiment of the present invention is a pharmaceutical composition for treating the effects of a lymphoid malignancy. This pharmaceutical composition comprises a pharmaceutically acceptable carrier and an effective amount of a PI3Kδ inhibitor and a PI3Kγ inhibitor.

In one aspect of this embodiment, the pharmaceutical composition is in a unit dosage form.

In another aspect of this embodiment, the pharmaceutical composition further comprises an effective amount of a chemotherapeutic agent as disclosed herein, such as a glucocorticoid. Preferably, the chemotherapeutic agent is dexamethasone.

An additional embodiment of the present invention is a method for treating a subject suffering from T-ALL. This method comprises administering to the subject an effective amount of a pharmaceutical composition comprising a PI3Kδ inhibitor and a PI3Kγ inhibitor.

The PI3Kδ inhibitor and the PI3Kγ inhibitor are as disclosed herein. Preferably, the PI3Kδ inhibitor and the PI3Kγ inhibitor are CAL-130. The pharmaceutical composition of this embodiment may be a single composition containing a dual inhibitor such as, e.g., CAL-130, a single composition containing two active agents, one a PI3Kδ inhibitor and the other a PI3Kγ inhibitor, or two or more compositions each containing at least one active agent that is a PI3Kδ inhibitor or a PI3Kγ inhibitor.

In one aspect of this embodiment, the method further comprises administering an effective amount of a chemotherapeutic agent as disclosed herein, such as a glucocorticoid. Preferably, the chemotherapeutic agent is dexamethasone.

Another embodiment of the present invention is a method for lowering tumor burden in a subject suffering from T-ALL. This method comprises administering to the subject an effective amount of a pharmaceutical composition comprising a PI3Kδ inhibitor and a PI3Kγ inhibitor.

As used herein, "tumor burden" means the number of tumor (whether benign or malignant) cells in the subject's body, or the size of a tumor.

The PI3Kδ inhibitor and the PI3Kγ inhibitor are as disclosed herein. Preferably, the PI3Kδ inhibitor and the PI3Kγ inhibitor are CAL-130.

In one aspect of this embodiment, the method further comprises administering an effective amount of a chemotherapeutic agent as disclosed herein, such as a glucocorticoid also as defined herein. Preferably, the chemotherapeutic agent is dexamethasone.

Yet another embodiment of the present invention is a method for identifying a subject who may benefit from co-treatment with a PI3Kδ inhibitor and a PI3Kγ inhibitor. This method comprises determining from a sample of the subject whether the subject has a mutated PTEN gene, wherein the presence of the mutated PTEN gene is indicative of a subject who may benefit from co-treatment.

In this embodiment, the sample is obtain from the subject by any conventional means. Such a sample contains DNA and may be a tissue and/or blood sample, such as a peripheral blood sample. Such a sample may also be biopsy from a tumor. Determining whether a subject has a mutated PTEN gene may be carried out using any conventional genotyping methods known in the art, or by assaying for the PTEN gene product using any conventional means, including the methods disclosed herein, including in the Examples.

The PI3Kδ inhibitor and the PI3Kγ inhibitor are as disclosed herein. Preferably, the PI3Kδ inhibitor and the PI3Kγ inhibitor are CAL-130.

An additional embodiment of the present invention is a method for identifying a compound that has both PI3Kδ and PI3Kγ inhibitory activity. This method comprises:

(a) contacting a cell with the compound; and
(b) determining whether the compound modulates an antigen receptor-induced activity in the cell;
wherein a compound that modulates the antigen receptor-induced activity has both PI3Kδ and PI3Kγ inhibitory activity.

As used herein, an "antigen receptor-induced activity" means an event resulting from T-cell receptor signaling, such as, e.g., phosphorylation of AKT, GSK3β, mTOR, p70S6K, BAD proteins and calcium flux in CD4$^+$ T cells. Assays for such activities are as disclosed herein.

A pharmaceutical composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a pharmaceutical composition of the present invention may be administered in conjunction with other treatments. A pharmaceutical composition of the present invention maybe encapsulated or otherwise protected against gastric or other secretions, if desired.

The pharmaceutical compositions of the invention are pharmaceutically acceptable and comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, PA).

Pharmaceutically acceptable carriers are well known in the art (see, e.g., Remington, The Science and Practice of Pharmacy (21$^{st}$ Edition, Lippincott Williams and Wilkins, Philadelphia, PA) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the invention may, optionally, contain additional ingredients and/or materials commonly used in such pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Additional Definitions

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Nucleic Acid

"Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (siRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

siRNA gene-targeting may be carried out by transient siRNA transfer into cells, achieved by such classic methods as lipid-mediated transfection (such as encapsulation in liposome, complexing with cationic lipids, cholesterol, and/or condensing polymers, electroporation, or microinjection). siRNA gene-targeting may also be carried out by administration of siRNA conjugated with antibodies or siRNA complexed with a fusion protein comprising a cell-penetrating peptide conjugated to a double-stranded (ds) RNA-binding domain (DRBD) that binds to the siRNA (see, e.g., U.S. Patent Application Publication No. 2009/0093026).

An shRNA molecule has two sequence regions that are reversely complementary to one another and can form a double strand with one another in an intramolecular manner. shRNA gene-targeting may be carried out by using a vector introduced into cells, such as viral vectors (lentiviral vectors, adenoviral vectors, or adeno-associated viral vectors for example). The design and synthesis of siRNA and shRNA molecules are known in the art, and may be commercially purchased from, e.g., Gene Link (Hawthorne, NY), Invitrogen Corp. (Carlsbad, CA), Thermo Fisher Scientific, and Dharmacon Products (Lafayette, CO).

The nucleic acid may also be an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'—OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, NH$_2$, NHR, NR$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No. 20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

Peptide, Polypeptide, Protein

The terms "peptide," "polypeptide," and "protein" are used interchangeably herein. In the present invention, these terms mean a linked sequence of amino acids, which may be natural, synthetic, or a modification, or combination of natural and synthetic. The term includes antibodies, antibody mimetics, domain antibodies, lipocalins, targeted proteases, and polypeptide mimetics. The term also includes vaccines containing a peptide or peptide fragment intended to raise antibodies against the peptide or peptide fragment.

Polysaccharides

The term "polysaccharides" means polymeric carbohydrate structures, formed of repeating units (either mono- or di-saccharides) joined together by glycosidic bonds. The units of mono- or di-saccharides may be the same or different. Non-limiting examples of polysaccharides include starch, glycogen, cellulose, and chitin.

Small Organic or Inorganic Molecules

The phrase "small organic" or "small inorganic" molecule includes any chemical or other moiety, other than polysaccharides, polypeptides, and nucleic acids, that can act to affect biological processes. Small molecules can include any number of therapeutic agents presently known and used, or can be synthesized in a library of such molecules for the purpose of screening for biological function(s). Small molecules are distinguished from macromolecules by size. The small molecules of this invention usually have a molecular weight less than about 5,000 daltons (Da), preferably less than about 2,500 Da, more preferably less than 1,000 Da, most preferably less than about 500 Da.

As used herein, the term "organic compound" refers to any carbon-based compound other than biologics such as nucleic acids, polypeptides, and polysaccharides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, mono-saccharides, di-saccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds. Collections of small molecules, and small molecules identified according to the invention are characterized by techniques such as accelerator mass spectrometry (AMS; see Turteltaub et al., Curr Pharm Des 2000 6:991-1007, Bioanalytical applications of accelerator mass spectrometry for pharmaceutical research; and Enjalbal et al., Mass Spectrom Rev 2000 19:139-61, Mass spectrometry in combinatorial chemistry.)

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

The following examples are provided to further illustrate the methods and compositions of the present invention. These examples are illustrative only and are not intended to limit the scope of the invention in any way.

EXAMPLES

Example 1

Materials and Methods

Mice and Animal Procedures.

All mice were kept in a specific pathogen-free facility at Columbia University Medical Center. All mice studies and breeding were carried out under the approval of the Institutional Animal Care and Use Committee of Columbia University.

Mice (p110$\delta^{-/-}$ and p110$\gamma^{-/-}$) on a mixed B6/129 background were described previously (Sasaki et al., 2000; Clayton et al., 2002). Animals were bred to generate a deficiency in both p110 catalytic subunits, the p110$\gamma^{-/-}$ mice. Other names for the mouse include p110$\gamma\delta^{ko}$ and Pik3cg$^{-/-}$; Pik3cd$^{-/-}$, because p110$\gamma$ is encoded by Pik3cg and p110$\delta$ is encoded by Pik3cd.

NOD.Cg-Prkdc$^{scid}$ Il2rg$^{tm1}$Wjl/Sz mice for xenograft experiments and Gt(ROSA)26Sor$^{tm1(Luc)Kael}$/J for bioimaging studies were obtained from The Jackson Laboratory (Bar Harbor, ME). Mice deficient for PTEN in the T cell lineage were generated by crossing Lck-cre with floxed Pten (Hennet et al., 1995; Trotman et al., 2003). P110$\gamma^{-/-}$ and p110$\delta^{-/-}$ mice were intercrossed with Lckcre/Pten$^{fl/fl}$ animals to generate mice homozygous mutant for either p110$\gamma$ or p110$\delta$ and Pten or homozygous mutant for p110$\gamma$, 110$\delta$, and Pten.

For subcutaneous xenograft experiments, luminescent CCRF-CEM (CEM-luc) cells were generated by lentiviral infection with FUW-luc and selection with neomycin. Luciferase expression was verified with the Dual-Luciferase Reporter Assay kit (Promega Corp., Madison, WI). $2.5\times10^6$ CEM-luc cells embedded in Matrigel (BD Biosciences, San Jose, CA) were injected into the flank of NOD.Cg-Prkdc$^{scid}$ Il2rg$^{tm1\,Wjl}$/Sz mice. After 1 week, mice were treated by oral gavage with vehicle (0.5% methyl cellulose, 0.1% Tween-80), or CAL-130 (10 mg kg$^{-1}$) (Gilead Sciences, Foster City, CA) every 8 hours daily for 4 days and then tumors imaged as follows: mice anesthetized by isoflurane inhalation were injected intraperitoneally with D-luciferin (50 mg kg$^{-1}$, Xenogen, Calipers Life Sciences, Hopkinton, MA). Photonic emission was imaged with the In Vivo Imaging System (IVIS, Xenogen). Tumor bioluminescence was quantified by integrating the photonic flux (photons per second) through a region encircling each tumor using the LIVING IMAGES software package (Xenogen). Administration of D-luciferin and detection of tumor bioluminescence in Lck/Pten$^{fl/fl}$/Gt (ROSA)26Sor$^{tm1(Luc)Kael}$/J mice was performed in a similar manner.

For intravenous xenograft transplantation, $5\times10^6$ CCRF-CEM cells were injected intravenously in fourteen NOD.Cg-Prkdc$^{scid}$ Il2rg$^{tm1\,Wjl}$/Sz mice. After 3 days, mice were segregated into two treatment groups that received either CAL-130 or vehicle by oral gavage as described above for 7 days. Mice in both groups were then followed until moribund (and euthanized).

Cell Counts, Antibodies, Flow Cytometry, Cell Lines, and Reagents.

Cell counts were measured on a Hemavet 850FS system (CDC Technologies, Oxford, CT), and standard procedures were followed for staining cells with the following antibody conjugates for flow cytometry (BD Biosciences, San Jose, CA) (Cella et al., 2004): phycoerythrin (PE) anti-CD4 (clone H129.19), fluorescein (FITC), PE, cytochrome c (CyC), or biotin anti-CD8a, FITC CD3c, CyC anti-B220, and Thy 1.2. Biotinylated antibodies were detected with either streptavidin-PE or streptavidin-CyC. Subsets of DN thymocytes were analyzed based on expression of CD25 and CD44 after gating out cells that stained with a cocktail of biotinylated antibodies to CD4, CD8, B220, Mac-1, and Gr-1 followed by streptavidin Cy-Chrome.

For intracellular staining of TCRB, cells were first labeled with PE-CD4 and Cy-Chrome-CD8$\alpha$, then were fixed and permeabilized in 1% saponin, and finally were stained with FITC-labeled anti-C$\beta$-specific antibody. For identifying apoptotic thymocytes, cell suspensions in DMEM and 10% fetal calf serum (FCS; $2\times10^6$/mL) were first labeled with PE-CD4 or PE-Cy5 CD8a, washed, and incubated with annexin V-FITC (BD Biosciences) according to the manufacturer's recommendations. A viable lymphocyte gate was first established based on forward and side scatter parameters, and dead cells were excluded by the detection of propidium iodide (PI) uptake in the absence of CD4 or CD8 labeling.

For studies evaluating spontaneous apoptosis, purified thymocytes were resuspended in DMEM, 10% FCS, and 2 mM glutamine ($25\times10^5$ cells/mL), and 200 µL was placed in 96-well plates (5% $CO_2$, 37° C.). Cells were harvested at 24 hours to determine the extent of apoptosis, as described. All samples were analyzed on a FACS Calibur flow cytometer (BD Biosciences) using CellQuest or FlowJo software. Data are displayed as histograms or dot blots with logarithmic scale. Each plot represents analysis of $2\times10^5$ or more events collected as list mode files.

For cell surface staining in mouse whole blood, following incubation with appropriate antibodies, blood was processed using the BD Bioscience BD FACS Lysing Solution according to the manufacturer's instructions. For intracellular staining of Ki67, immediately after RBC lysis with the BD FACS Lysing solution cells were permeabilized without washing with 0.025% Tween-20 in lysing solution for an additional 15 minutes, washed, and then incubated with Ki67 antibodies.

Thymic tissue, peripheral blood, spleens, and lymph nodes from the mice displaying the following combinations of PI3K genetic deletion were used: WT (full activity of both PI3Kγ and PI3δ), $\gamma^{het}/\delta^{het}$ (50% reduction in activity of both PI3Kγ and PI3δ), $\gamma^{ko}/\delta^{het}$ (full reduction of PI3Kγ activity and 50% reduction of PI3Kδ activity), $\gamma^{het}/\delta^{ko}$ (50% reduction of PI3Kγ activity and full reduction of PI3Kδ activity) and $\gamma^{ko}/\delta^{ko}$ (full reduction of PI3Kγ and PI3Kδ activity). Analyses included tissue histology of thymi, spleens, and lymph nodes to determine structure and organization of cells, cell counts to determine differences of WBC numbers in tissues and blood for each genotype, and flow cytometry to evaluate differences in total thymocyte populations ($CD3^+$ and subsets $CD4^+/CD8^+$).

CCRF-CEM, CEM/C1, and MOLT-4 cells were obtained from ATCC and grown in RPMI-1640 medium containing 10% FBS and antibiotics.

Antibodies to Akt (catalog #9272), phospho-Akt (S473, clone 193H12), phosphomTOR (S2448, catalog #2971S), mTOR (catalog #2972), phospho-GSK3αβ (S21/9, catalog #9331S), GSK-3β (clone 27C10), phospho-p70S6K (Thr389, catalog #9205S) and p70S6K (catalog #9202) and β-actin (catalog #4967S) were from Cell Signaling Technology (Danvers, MA). Antibodies to class I PI3K subunits were as follows: p110α (catalog #4255) from Cell Signaling Technology; p110β (clone Y384) from Millipore and mouse p110β from Santa Cruz Biotechnology (Santa Cruz, CA) (catalog #sc-602); p110γ (clone H1) from Jena Biosciences (Jena, Germany); p110δ (clone H-219) from Santa Cruz Biotechnology. Antibodies to PTEN (clone 6H2.1) were from Cascade Bioscience (Winchester, MA). For flow cytometry, antibodies were obtained from BD Biosciences: CD3c-Alexa 488 (clone 145-2C11), CD4-APC (clone RM4-5), CD8-PerCP-Cy5.5 (clone 53-6.7), CD90.2-APC (Thy-1.2, clone 53-2.1), Ki67-FITC (clone B56), and Annexin V-APC. Antibodies to Bim, phospho-Bad, Bad, and BclXL were from Cell Signaling Technology (pro-apoptotic sampler kit #9942S).

The shRNA construct for p110γ (MISSION® shRNA Plasmid DNA; clone ID: NM_002649.2-4744s1c1; TRC number: TRCN0000196870). siRNA constructs for p110α (ON-TARGET plus SMARTpool #L-003018-00) and p110β (ON-TARGET plus SMARTpool #L-003019-00) were obtained from Dharmacon (Thermo Scientific, Waltham, MA).

Primary Leukemia Samples.

Cryopreserved samples were provided by collaborating institutions in the US (Department of Pediatrics, Columbia Presbyterian Hospital and Departments of Medicine and Pathology, Vanderbilt University), The Netherlands (Erasmus MC-Sophia Children's Hospital), and Italy (Hemato-Oncology Laboratory, Department of Pediatrics, University of Padua). All samples were collected with informed consent and under the supervision of the Medical Ethics Committee of the Erasmus Medical Center, the Columbia University Medical Center Institutional Review Board, the Vanderbilt University Medical Center Institutional Review Board, and the Acute Lymphoblastic Leukemia Strategic Scientific Committee.

Cell Proliferation and Cell Viability Assay.

Cell proliferation of CCRF-CEM cells or shRNA transfected CCRF-CEM cells, in the presence or absence of appropriate drug, was followed by cell counting of samples in triplicate using a hemocytometer and trypan blue. For apoptosis determinations of untransfected or shRNA transfected CCRF-CEMs, cells were stained with APC-conjugated Annexin-V (BD Biosciences) in Annexin Binding Buffer (Miltyeni Biotec) and analyzed by flow cytometry. For primary T-ALL samples, cell viability was assessed using the BD Cell Viability kit (BD Biosciences) coupled with the use of fluorescent counting beads as previously described (Armstrong et al., 2009). For this, cells were plated with MS5-DL1 stroma cells, and after 72 hours following drug treatment cells were harvested and stained with an APC-conjugated anti-human CD45 followed by a staining with the above kit according to the manufacturer's instructions.

Fetal Liver Reconstitution

Timed pregnant wild-type (WT) littermates were killed on day 14.5 after coitus, and single-cell suspensions of fetal livers were prepared (Puri et al., 2005). Briefly, $1.5\times10^6$ cells in PBS were injected intravenously (tail vein) into lethally irradiated 6-week-old p110γ$^{-/-}$ mice (950 rads [9.5 Gy] single dose, 6 hours before injection). At 6 to 8 weeks after transplantation, complete blood cell counts were taken to confirm engraftment before using mice in experiments.

Tissue Histology

Thymi, spleens, and lymph nodes harvested from 4-week-old mice were either formalin-fixed and paraffin embedded or snap frozen at −80° C. in liquid nitrogen. Hematoxylin-eosin staining was applied on fixed material for morphologic analysis. Immunohistochemistry was performed according to an indirect immunoperoxidase technique using the following primary antibodies: B220 (Valter Occhiena, Milan, Italy; 1:10), CD3 (Valter Occhiena; 1:10), CD4-biotinylated (Southern Biotechnology, Birmingham, AL; 1:200), CD8 (Valter Occhiena; 1:10), cytokeratin 5 (anti-K5, rabbit polyclonal; Covance, Princeton, NJ; 1:50), and cytokeratin 8 (anti-K8; Progen Biotechnik, Heidelberg, Germany; 1:20). Specimens were visualized using an Olympus BX60 optical microscope, and images were acquired with a DP70 digital camera (Olympus). Image analysis was performed using analySIS (Soft Imaging System, Munster, Germany).

CAL130 $IC_{50}$.

CAL-130 is a derivative of IC87114 (Gilead Sciences, Foster City, CA), the synthesis of which has been previously described (Sadhu et al., 2003 and Sadhu et al., U.S. Pat. Nos. 6,518,277 and 6,667,300, which are incorporated by reference as if recited in full herein). 1050 values for CAL-130 inhibition of PI3K isoforms were determined in ex-vivo PI3 kinase assays using recombinant PI3K. A 10-point kinase inhibitory profile was determined with ATP at a concentration consistent with the $K_m$ for each enzyme (Puri et al., 2004).

Calcium Flux Assay

Thymocytes or lymphocytes were preloaded with Fluo-4 AM (Molecular Probes, Eugene, OR) at 5 µg/mL for 30 minutes at 37° C., labeled with anti-CD4-APC conjugate (BD Biosciences) to permit gating on this T-cell subset during analysis, and finally washed and resuspended ($2\times10^6$/ mL) in DMEM and 10% FCS. After a baseline was established at quiescence, $Ca^{2+}$ flux was induced by the addition in tandem of anti-CD3e (hamster antimouse antibody; BD Biosciences) and the anti-hamster IgG polyclonal antibody (Jackson ImmunoResearch, West Grove, PA) for cross-linking. The resultant flux in $Ca^{2+}$ was measured for 5 minutes by flow cytometry, and total flux was established by the addition of ionomycin (0.5 μg/mL). Drug inhibition of $Ca^{2+}$ flux was measured after 30 minute pre-incubation with CAL-130 at room temperature of dye loaded cells. Percentage overall change in $Ca^{2+}$ flux is reported as $(Ca^{2+} flux_{peak} - Ca^{2+} flux_{baseline} / Ca^{2+} flux_{ionomycin} - Ca^{2+} flux_{baseline}) \times 100$.

Western Blot Analysis

Protein extracts from thymus homogenates (30 μg protein per lane) were electrophoresed in polyacrylamide gels (Invitrogen Life Technologies, Carlsbad, CA), transferred to a PVDF membrane (Immobilon-P; Millipore, Billerica, MA) and incubated overnight (4° C.) with antibodies to p110α, p110β, p110γ, p110δ, or p85α (Santa Cruz Biotechnology, Santa Cruz, CA) and then with horseradish peroxidase-conjugated secondary antibodies. Bound antibody was detected by chemiluminescence according to the manufacturer's instructions (Amersham Biosciences, Piscataway, NJ). Membranes were stripped and reblotted with anti-actin antibody (Sigma-Aldrich, St Louis, MO) to verify equal loading of protein.

Cell lysates (from cell lines or thymocytes) were prepared on ice in M-PER Mammalian Protein Extraction reagent (Pierce) containing a cocktail of protease and phosphatase inhibitors (Swat et al., 2006). Equal amounts of total protein from lysates were subjected to SDS-PAGE, transferred to PVDF membrane (Immobilon-P, Millipore), and membranes probed by overnight incubation with appropriate primary antibodies. Bound antibodies were visualized with HRP-conjugated secondary antibodies and ECL chemistry (Super-Pico West, Pierce).

Akt/PBK Activation

To assess the requirement for p110δ in TCR-induced phosphorylation of Akt/PBK, single-cell suspensions of thymocytes ($1 \times 10^8$/mL) from PI3Kγ-deficient animals were incubated with the p110δ-specific inhibitor IC87114 (10 μM) or with vehicle control (DMSO) for 30 minutes before TCR cross-linking, as described for the $Ca^{2+}$ flux assay. Aliquots (100 μL) were collected at 0, 10, 30, and 60 minutes after TCR cross-linking, briefly centrifuged to pellet, and subsequently lysed with ice-cold M-Per (Pierce, Rockford, IL) (according to the manufacturer's recommendations) that contained a cocktail of phosphatase and protease inhibitors (Puri et al., 2005). Lysates were clarified by centrifugation (12,000 g for 15 minutes at 4° C.), and total and phosphorylated Akt/PBK were determined by Western blot analysis.

In Vivo BrdU Labeling

BrdU incorporation analyses were performed using a BrdU labeling kit (BD Biosciences). In brief, mice received intraperitoneal injections with 150 μL BrdU solution (10 mg/mL), and BrdU incorporation was analyzed 20 hours after injection. Thymocyte suspensions were first surface stained with anti-CD4-PE and anti-CD8-CyC antibodies, fixed, and permeabilized in BD Cytofix/Cytoperm buffer, then washed and refixed. To expose incorporated BrdU, cells were treated with DNase solution, washed, stained with anti-BrdU-FITC antibodies, and analyzed by flow cytometry.

Organ Culture of E14.5 Thymus Lobes

Thymus lobes were obtained from mouse embryos, with embryonic day 0 (EO) considered the day of vaginal plug detection. Fetal thymus organ cultures were used to compare the effects of pharmacologic blockade of p110δ activity on thymocyte development in WT, p110δ$^{-/-}$, and p110γ$^{-/-}$ mice. Briefly, 3 to 4 intact thymi were placed on bare filter inserts (transwell, 3-μm pore size; Corning Costar, Cambridge, MA) and then were inserted into wells containing DMEM, 10% FCS supplemented with either p110δ-specific inhibitor IC87114 (10 μM) or vehicle control (DMSO), and incubated for 1 week at 37° C. in 5% $CO_2$. Thymocyte differentiation was evaluated by flow cytometry.

Statistical Analysis

Statistical analyses were performed using Student's t-test (GraphPad Prizm software). Kaplan-Meier survival curves were analyzed using a logrank test (Graph Pad Prism software). Values were considered significant at $P<0.5$.

Histological and Immunohistochemical Study of Tissue Samples.

Formalin-fixed paraffin-embedded 5 μm tissue sections were stained with Hematoxylin & Eosin for histopathological diagnosis. For immunohistochemistry, anti-Ki67 (rabbit monoclonal, Abcam) and anti-CD3 (rabbit polyclonal, Dako) staining were performed on similar tissue sections after antigen retrieval by microwave heating in citrate buffer (pH 6.0). After epitope recovery, slides were incubated with antibody (anti-Ki67 1:50, anti-CD3 1:50) overnight at room temperature before antigen detection with diaminobenzidine (DAB) using a Ventana automated staining platform (Ventana).

shRNA and siRNA Knockdown.

CCRF-CEMs were transfected using the Amaxa Human T cell Nucleofector kit (Lonza, Basel, Switzerland) according to the manufacturer's optimized protocol kit for this cell line.

For shRNA knockdown of p110γ, CCRF-CEM ($2 \times 10^6$ cells) were transfected with 2 μg of purified plasmid DNA, and clones were selected by high dilution in puromycin used at a concentration pre-determined by a killing curve. Expression of p110γ and p110δ were determined by Western blotting.

For siRNA knockdown of p110α or p110δ, CCRF-CEM ($2 \times 10^6$ cells) were transfected with 300 nM of siRNA construct. After a brief recovery period, cells were diluted to between $1-2 \times 10^5$ per ml and grown for further 48 hours for cell counting, flow cytometry and Western blotting.

Plasma Levels of CAL130, Glucose and Insulin.

For CAL-130 level determinations, animals received a single oral dose (10 mg kg$^{-1}$ or 20 mg kg$^{-1}$) of inhibitor. Plasma was collected at 0, 2, 4, 8, and 12 hours and subjected to high-performance liquid chromatography-MS/MS (sensitivity 1 ng/mL). The concentration of CAL-130 in plasma was determined using a standard curve (analyte peak area versus concentration) generated with calibration standard pools. Values represent the mean (±SD) for four animals per group.

Plasma glucose and insulin levels were determined following a single oral dose of CAL-130 (10 mg kg$^{-1}$). Blood was collected into $K_2$EDTA tubes by cardiac puncture at baseline and 0, 2, 4, and 8 hours post-dose, and plasma samples frozen at −80° C. until analysis. The insulin and glucose levels were determined by using an Ultra Sensitive Mouse Insulin ELISA Kit (Crystall Chem Inc.) or WaveSense Presto Blood Glucose Monitoring System (Agamatrix Inc., Boston, MA), respectively.

Quantitative Real-Time PCR.

RNA from cells was isolated using the Qiagen RNeasy Mini Kit (cat #74104) according to the manufacturer's protocol. The isolated total RNA was reverse transcribed using a high capacity cDNA synthesis kit (SuperScript First-Stand Synthesis System, Invitrogen part number 11904-018) according to the manufacturer's protocol. Pre-designed labeled primer and probe sets for human p110 alpha (Hs00180679_m1), human p110 beta (Hs00927728_m1), human p110 delta (Hs00192399_m1), human p110 gamma (Hs00277090_m1), human GAPDH (Hs03929097_g1), mouse p110 alpha (Mm00435673_m1), mouse p110 beta (Mm00659576_m1), mouse p110 delta (Mm00435674_m1), mouse p110 gamma (Mm00445038_m1), and mouse GAPDH (Mm99999915_g1) were from Applied Biosystems.

The PCR reactions were set up following the protocol of USB (hotStart-IT Probe qPCR system Cat #75764). Real time relative quantitative PCR was run on AB17500 with cycling conditions of 50° C. for 2 minutes, 95° C. for 10 minutes, 40 cycles of 95° C. for 15 seconds and 60° C. for 1 minute. Data exported from the AB17500 machine were processed and analyzed using an Excel spread sheet. Briefly, target genes were normalized to the housekeeping gene GAPDH to obtain a $\Delta$CT value. Relative quantitative expression was calculated with equation ($2^{-\Delta\Delta CT}$) where the $\Delta\Delta$CT is the difference between the $\Delta$CT of tumor samples and control samples ($\Delta\Delta$CT=$\Delta$CT tumor−$\Delta$CT control). A Student's t-test was used to determine statistical difference in expression levels with P values <0.05 considered significant.

PI3K$\alpha$ □ Isoform Selective Cell-Based Assay.

For the analysis of p110$\alpha$-mediated signaling, SW3T3 cells were placed in serum free media (3 hours) and incubated with either CAL-130 or the Pan-PI3K/mTor inhibitor BEZ235 (Selleck Chemicals) for 1 hour prior to stimulation with PDGF (10 ng/ml; Cell Signaling) for 10 minutes at 37° C. After washing once in cold phosphate-buffered saline (PBS), the cell pellet was resuspended in lysis buffer (50 mM HEPES [N-2-hydroxyethylpiperazine-N-2-ethanesulfonic acid], pH 7.4, 150 mM NaCl, 10% glycerol, 1% Triton X-100, 1.5 mM $MgCl_2$, 1 mM EGTA [ethylene glycol tetraacetic acid], 100 mM NaF, 1 mM phenylmethylsulfonyl fluoride, 1 mM NaVO4, 1 µg/ml leupeptin, and 1 µg/ml aprotinin) for 15 minutes on ice. Whole-cell lysates were obtained by centrifugation, and the soluble protein analyzed by Western blotting for Akt and P-Akt levels. Quantification was done using the Li-COR Odyssey imaging system.

CAL-130 Inhibits Proliferation and Induces Apoptosis in CEM/C1 and MOLT-4 Cell Lines.

Cell proliferation of CEM/C1 and MOLT-4 was determined in the presence or absence of PI3K$\gamma$ inhibitor 1C87114 (Gilead Sciences, Foster City, CA), the PI3K$\delta$ inhibitor AS-650240 (Selleck Chemicals), the PI3K$\delta$/$\gamma$ dual inhibitor CAL-130 (Gilead Sciences), or the Pan-PI3K/mTor inhibitor BEZ235 (Selleck Chemicals) by cell counting of samples in triplicate using a hemocytometer and trypan blue. Cells were cultured for 72 hours at 37° C. with or without inhibitors. The percentage of apoptotic cells was determined by Annexin V-FITC/7AAD staining followed by 2-color flow cytometric analysis.

Platelet Aggregation.

Blood was obtained from anesthetized p110$\delta$/$\gamma$ double knockout mice via cardiac puncture. Platelets were purified from PRP by centrifugation and resuspended to a final concentration of 400,000/pl in buffer (145 mM NaCl, 10 mM Hepes, 0.5 mM Na2HPO4, 5 mM KCl, 2 mM $MgCl_2$, 1 mM $CaCl_2$, 0.1% glucose, pH 7.4). CAL-130 (1 µM, 2.5 µM, or 5 µM final concentration) or DMSO was added to platelet suspensions 5 minutes prior to inducing aggregation with ADP (25 µM). Mouse fibrinogen (final concentration 200 µg/ml) was also added to the platelet suspensions just prior to activation as previously described (Magallon et al., 2011). Aggregation was assessed using a Chronolog Lumi-Aggregometer (model 540 VS, Chronolog, Havertown, PA). In some experiments, blood was collected 2 hours after administering a single dose of CAL-130 (10 mg $kg^{-1}$) or vehicle control and ADP-induced aggregation evaluated.

P110 Catalytic Domain Selectivity of CAL-130 as Assessed by Ambit KinomeScan Screening.

CAL-130 (10 µM) was evaluated for its ability to prevent tagged kinases from interacting with immobilized "bait" ligand (Karaman et al., 2008). Results are reported as "% of control binding", where lower numbers indicate stronger interactions with the tagged kinase. Values of >35% are considered "no hits". PI3K$\delta$ had the lowest percentage of control binding at 0.2% followed by PI3K$\gamma$ at 3.2% (See Table 1 below). These values indicate a high probability of a potent interaction. 353 kinases were assessed in the screen (Table 2).

TABLE 1

P110 catalytic domain selectivity of CAL-130 as assessed by Ambit KinomeScan screening.

| Ambit Gene Symbol | Percent of Control Binding |
|---|---|
| PIK3CA | 12 |
| PIK3CG | 10 |
| PIK3CB | 3.2 |
| PIK3CD | 0.2 |

TABLE 2

Ambit KinomeScan screening of 353 kinases.

| Ambit Gene Symbol | Percent of Control Binding | Ambit Gene Symbol | Percent of Control Binding |
|---|---|---|---|
| AAK1 | 100 | BMPR2 | 100 |
| ABL1 | 100 | BMX | 100 |
| ABL1(E255K) | 100 | BRAF | 100 |
| ABL1(F317I) | 100 | BRAF(V600E) | 100 |
| ABL1(F317L) | 100 | BRK | 100 |
| ABL1(H396P) | 100 | BRSK1 | 100 |
| ABL1(M351T) | 100 | BRSK2 | 100 |
| ABL1(Q252H) | 100 | BTK | 100 |
| ABL1(T315I) | 100 | CAMK1 | 100 |
| ABL1(Y253F) | 100 | CAMK1D | 100 |
| ABL2 | 100 | CAMK1G | 100 |
| ACVR1 | 100 | CAMK2A | 100 |
| ACVR1B | 100 | CAMK2B | 100 |
| ACVR2A | 100 | CAMK2D | 100 |
| ACVR2B | 100 | CAMK2G | 100 |
| ACVRL1 | 100 | CAMK4 | 100 |
| ADCK3 | 100 | CAMKK1 | 100 |
| ADCK4 | 100 | CAMKK2 | 18 |
| AKT1 | 100 | CDC2L1 | 100 |
| AKT2 | 100 | CDC2L2 | 100 |
| AKT3 | 100 | CDK11 | 100 |
| ALK | 100 | CDK2 | 100 |
| AMPK-α1 | 100 | CDK3 | 100 |
| AMPK-α2 | 100 | CDK5 | 100 |
| ANKK1 | 100 | CDK7 | 100 |
| ARK5 | 100 | CDK8 | 100 |
| ASK1 | 100 | CDK9 | 100 |
| ASK2 | 100 | CDKL2 | 100 |
| AURKA | 100 | CDKL3 | 100 |
| AURKB | 100 | CDKL5 | 100 |
| AURKC | 100 | CHEK1 | 100 |
| AXL | 100 | CHEK2 | 100 |
| BIKE | 100 | CIT | 100 |
| BLK | 100 | CLK1 | 100 |
| BMPR1A | 100 | CLK2 | 100 |

TABLE 2-continued

Ambit KinomeScan screening of 353 kinases.

| Ambit Gene Symbol | Percent of Control Binding | Ambit Gene Symbol | Percent of Control Binding |
|---|---|---|---|
| BMPR1B | 100 | CLK3 | 100 |
| CLK4 | 100 | EPHA1 | 100 |
| CSF1R | 100 | EPHA2 | 100 |
| CSK | 100 | EPHA3 | 100 |
| CSNK1A1L | 100 | EPHA4 | 100 |
| CSNK1D | 100 | EPHA5 | 100 |
| CSNK1E | 100 | EPHA6 | 100 |
| CSNK1G1 | 100 | EPHA7 | 100 |
| CSNK1G2 | 100 | EPHA8 | 100 |
| CSNK1G3 | 100 | EPHB1 | 100 |
| CSNK2A1 | 100 | EPHB2 | 100 |
| CSNK2A2 | 100 | EPHB3 | 100 |
| CTK | 100 | EPHB4 | 100 |
| DAPK1 | 100 | EPHB6 | 100 |
| DAPK2 | 100 | ERBB2 | 100 |
| DAPK3 | 100 | ERBB3 | 100 |
| DCAMKL1 | 100 | ERBB4 | 100 |
| DCAMKL2 | 100 | ERK1 | 100 |
| DCAMKL3 | 100 | ERK2 | 100 |
| DDR1 | 100 | ERK3 | 100 |
| DDR2 | 100 | ERK4 | 100 |
| DLK | 100 | ERK5 | 100 |
| DMPK | 100 | ERK8 | 100 |
| DMPK2 | 100 | ERN1 | 100 |
| DRAK1 | 100 | FAK | 100 |
| DRAK2 | 100 | FER | 100 |
| DYRK1A | 100 | FES | 100 |
| DYRK1B | 100 | FGFR1 | 100 |
| DYRK2 | 100 | FGFR2 | 100 |
| EGFR | 100 | FGFR3 | 100 |
| EGFR(E746-A750DEL) | 100 | FGFR3(G697C) | 100 |
| EGFR(G719C) | 100 | FGFR4 | 100 |
| EGFR(G719S) | 100 | FGR | 100 |
| EGFR(L747-E749DEL, A750P) | 100 | FLT1 | 100 |
| EGFR(L747-S752DEL, P753S) | 100 | FLT3 | 100 |
| EGFR(L747-T751DEL, SINS) | 100 | FLT3(D835H) | 100 |
| EGFR(L858R) | 100 | FLT3(D835Y) | 100 |
| EGFR(L858R, T790M) | 100 | FLT3(ITD) | 100 |
| EGFR(L861Q) | 100 | FLT3(K663Q) | 100 |
| EGFR(S752-I759DEL) | 100 | FLT3(N841I) | 100 |
| FLT4 | 100 | KIT(V559D, V654A) | 100 |
| FRK | 100 | LATS1 | 100 |
| FYN | 100 | LATS2 | 100 |
| GAK | 100 | LCK | 100 |
| GCN2(S808G) | 100 | LIMK1 | 100 |
| GRK1 | 100 | LIMK2 | 100 |
| GRK4 | 100 | LKB1 | 100 |
| GRK7 | 100 | LOK | 100 |
| GSK3A | 100 | LTK | 100 |
| GSK3B | 100 | LYN | 100 |
| HCK | 100 | LZK | 100 |
| HIPK1 | 100 | MAK | 100 |
| HIPK2 | 100 | MAP3K1 | 100 |
| HIPK3 | 100 | MAP3K15 | 100 |
| HIPK4 | 100 | MAP3K2 | 100 |
| HPK1 | 100 | MAP3K3 | 100 |
| HUNK | 100 | MAP3K4 | 100 |
| ICK | 100 | MAP4K2 | 100 |
| IGF1R | 100 | MAP4K3 | 100 |
| IKK-α | 100 | MAP4K4 | 100 |
| IKK-β | 100 | MAP4K5 | 100 |
| IKK-□ | 100 | MAPKAPK2 | 100 |
| INSR | 100 | MAPKAPK5 | 100 |
| INSRR | 100 | MARK1 | 100 |
| IRAK1 | 100 | MARK2 | 100 |
| IRAK3 | 100 | MARK3 | 100 |
| ITK | 100 | MARK4 | 100 |
| JAK1(JH1domain) | 100 | MAST1 | 100 |
| JAK1(JH2domain) | 100 | MEK1 | 100 |
| JAK2(JH1domain) | 100 | MEK2 | 100 |
| JAK3(JH1domain) | 100 | MEK3 | 100 |
| JNK1 | 100 | MEK4 | 100 |
| JNK2 | 100 | MEK6 | 100 |
| JNK3 | 100 | MELK | 100 |
| KIT | 100 | MERTK | 100 |
| KIT(D816V) | 100 | MET | 100 |
| KIT(L576P) | 100 | MET(M1250T) | 100 |
| KIT(V559D) | 100 | MET(Y1235D) | 100 |
| KIT(V559D, T670I) | 100 | MINK | 100 |
| MKNK1 | 100 | PAK7 | 100 |
| MKNK2 | 16 | PCTK1 | 100 |
| MLCK | 100 | PCTK2 | 100 |
| MLK1 | 100 | PCTK3 | 100 |
| MLK2 | 100 | PDGFRA | 100 |
| MLK3 | 100 | PDGFRB | 100 |
| MRCKA | 100 | PDPK1 | 100 |
| MRCKB | 100 | PFTAIRE2 | 100 |
| MST1 | 100 | PFTK1 | 100 |
| MST1R | 100 | PHKG1 | 100 |
| MST2 | 100 | PHKG2 | 100 |
| MST3 | 100 | PI3KCA | 12 |
| MST4 | 100 | PI3KCB | 10 |
| MUSK | 100 | PI3KCD | 0.1 |
| MYLK | 100 | PI3KCG | 1.2 |
| MYLK2 | 100 | PIK4CB | 100 |
| MYO3A | 100 | PIM1 | 100 |
| MYO3B | 100 | PIM2 | 100 |
| NDR1 | 100 | PIM3 | 100 |
| NDR2 | 100 | PIP5K1A | 100 |
| NEK1 | 100 | PIP5K2B | 100 |
| NEK2 | 100 | PKAC-α | 100 |
| NEK5 | 100 | PKAC-β | 100 |
| NEK6 | 100 | PKMYT1 | 100 |
| NEK7 | 100 | PKN1 | 100 |
| NEK9 | 100 | PKN2 | 100 |
| NIM1 | 100 | PLK1 | 100 |
| NLK | 100 | PLK2 | 100 |
| OSR1 | 100 | PLK3 | 100 |
| p38-α | 100 | PLK4 | 100 |
| p38-β | 100 | PRKCD | 100 |
| p38-δ | 100 | PRKCE | 100 |
| p38-γ | 100 | PRKCH | 100 |
| PAK1 | 100 | PRKCQ | 100 |
| PAK2 | 100 | PRKD1 | 100 |
| PAK3 | 100 | PRKD2 | 100 |
| PAK4 | 100 | PRKD3 | 100 |
| PAK5 | 100 | PRKG1 | 100 |
| PAK6 | 100 | PRKG2 | 100 |
| PRKR | 100 | STK35 | 100 |
| PRKX | 100 | STK36 | 100 |
| PRP4 | 100 | STK39 | 100 |
| PYK2 | 100 | SYK | 100 |
| QSK | 100 | TAK1 | 100 |
| RAF1 | 100 | TAO1 | 100 |
| RET | 100 | TAOK1 | 100 |
| RET(M918T) | 100 | TAOK3 | 100 |
| RET(V804L) | 100 | TBK1 | 100 |
| RET(V804M) | 100 | TEC | 100 |
| RIOK1 | 100 | TESK1 | 100 |
| RIOK2 | 100 | TGFBR1 | 100 |
| RIOK3 | 100 | TGFBR2 | 100 |
| RIPK1 | 100 | TIE1 | 100 |
| RIPK2 | 100 | TIE2 | 100 |
| RIPK4 | 100 | TLK1 | 100 |
| ROCK1 | 100 | TLK2 | 100 |
| ROCK2 | 100 | TNIK | 100 |
| ROS1 | 100 | TNK1 | 100 |
| RPS6KA1 | 100 | TNK2 | 100 |
| RPS6KA2 | 100 | TNNI3K | 100 |
| RPS6KA3 | 100 | TRKA | 100 |
| RPS6KA4 | 100 | TRKB | 100 |
| RPS6KA5 | 100 | TRKC | 100 |
| RPS6KA6 | 100 | TSSK1B | 100 |
| SBK1 | 100 | TTK | 11 |
| SgK085 | 100 | TXK | 100 |

TABLE 2-continued

Ambit KinomeScan screening of 353 kinases.

| Ambit Gene Symbol | Percent of Control Binding | Ambit Gene Symbol | Percent of Control Binding |
|---|---|---|---|
| SgK110 | 100 | TYK2(JH1domain) | 100 |
| SIK | 100 | TYK2(JH2domain) | 100 |
| SIK2 | 100 | TYRO3 | 100 |
| SLK | 100 | ULK1 | 100 |
| SNARK | 100 | ULK2 | 100 |
| SRC | 100 | ULK3 | 100 |
| SRMS | 100 | VEGFR2 | 100 |
| SRPK1 | 100 | WEE1 | 100 |
| SRPK2 | 100 | WEE2 | 100 |
| SRPK3 | 100 | YANK2 | 100 |
| STK16 | 100 | YANK3 | 100 |
| STK33 | 100 | YES | 100 |
| YSK1 | 100 | ZAK | 100 |
| YSK4 | 100 | ZAP70 | 100 |

Example 2

Abnormal Thymus Size and Structure in p110γδ$^{-/-}$ Mice

Figure 7B:
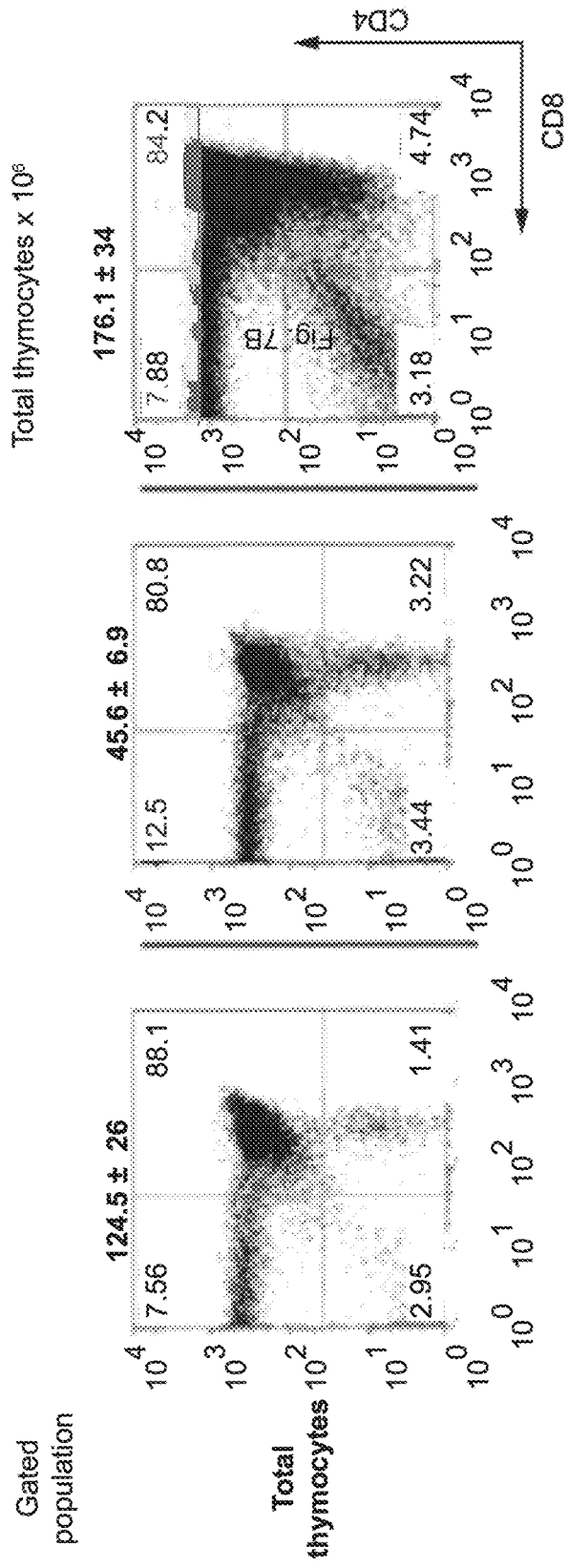
Figure 7C:
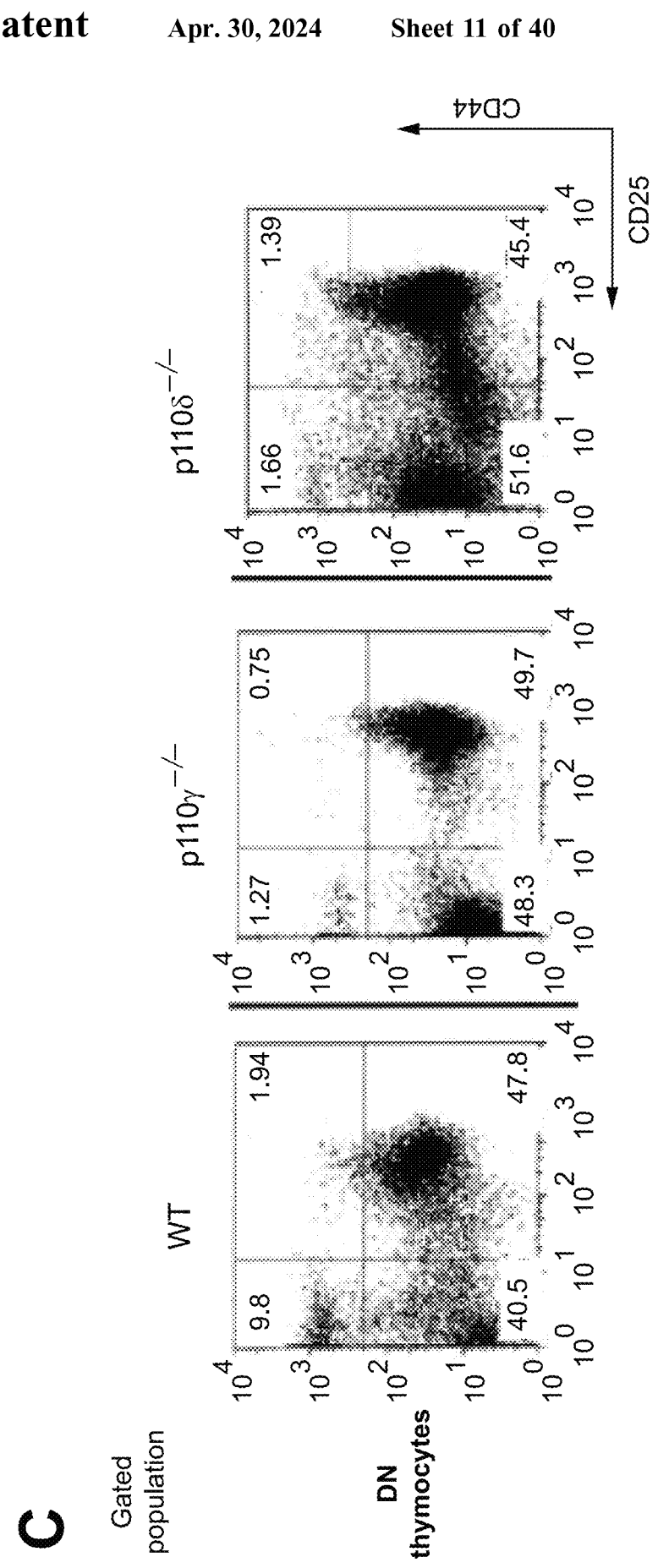

The absence of p110δ and p110γ catalytic subunits in 4-week-old mice resulted in a significant reduction in thymus size compared with either age-matched WT littermate controls (FIG. 1Ai-ii) or singly deficient animals (FIG. 7). Consequently, total cell counts in p110γ$^{-/-}$ thymi were significantly reduced compared with WT control (approximately 27-fold) or p110γ-deficient (approximately 10-fold) animals. No defect in thymus size or total cell count, however, was observed for mice deficient in p110δ. Strikingly, thymic sections from p110γ$^{-/-}$ mice revealed a unique phenotype, that is, a lack of corticomedullary differentiation (FIG. 1Aiv-v). This was confirmed by the disorganized pattern of K5$^+$ medullary epithelial cells (ECs), a finding consistent with disorders in T-cell development (FIG. 1Aviii) (Anderson et al., 2001). Moreover, this defect in corticomedullary differentiation was corrected on the reconstitution of p110γ$^{-/-}$ animals with WT fetal liver cells (FLCs), as the results of thymic histologic examination were relatively normal (FIG. 1Aix). Thymus size and cellularity were also restored to those observed for p110γ$^{-/-}$ mice, which is consistent with previous reports that the activity of this class 1b PI3K is required for thymic growth (FIG. 1Aiii) (Rodriguez-Borlado et al., 2003). Together, these results suggest a previously unrecognized interplay between class 1a and 1b PI3Ks in maintaining thymic organization and cellularity.

Example 3

Figures 8A, 8B:
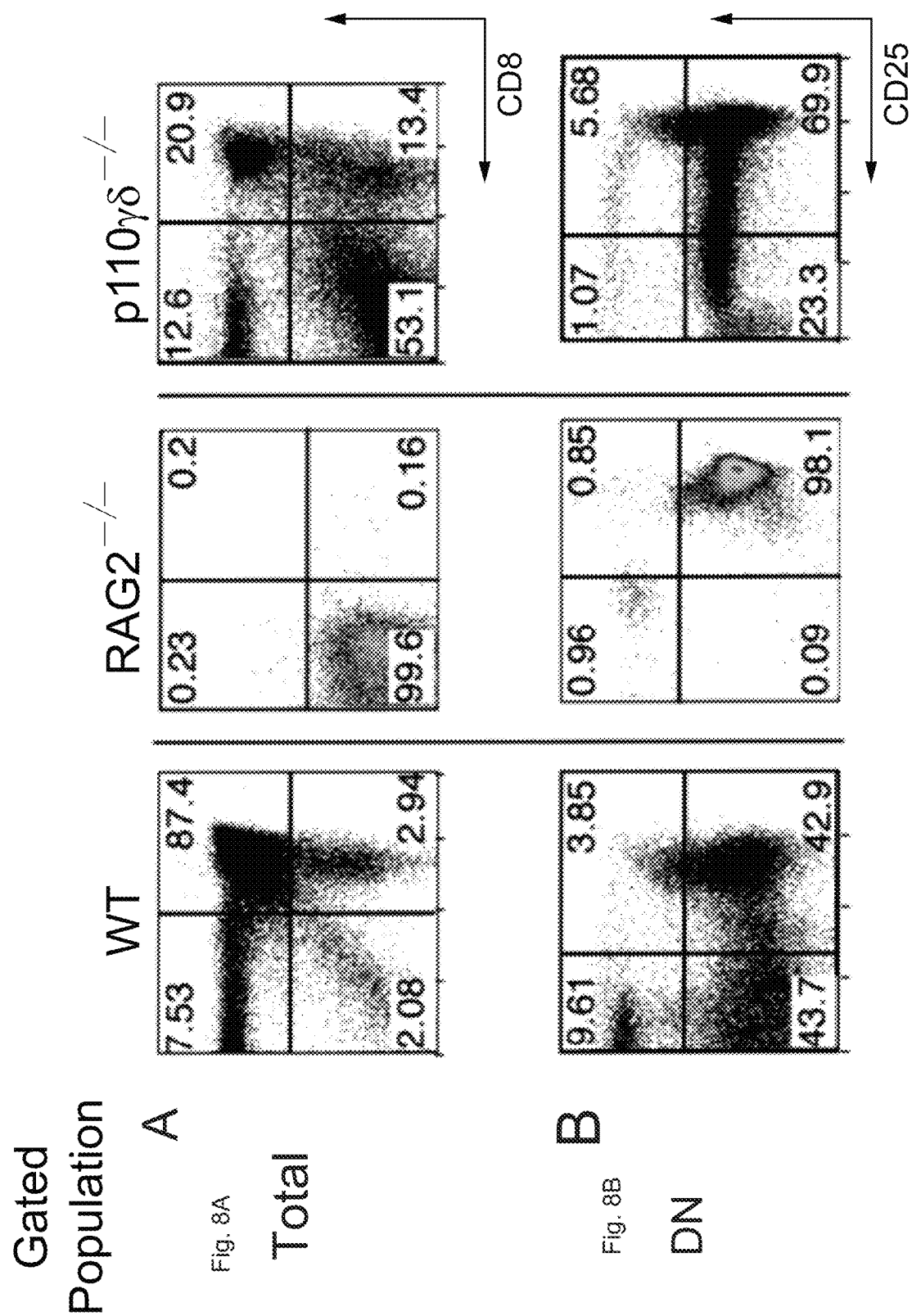
FIGS. 8A-8B show that representative flow cytometric analysis of expression of CD4 and CD8 SP and DP (FIG. 8A) and DN (FIG. 8B) thymocyte subsets from WT, $RAG2^{-/-}$, and $p110γ^{-/-}$ thymi. Data are representative of two independent experiments.

Depletion of DP Thymocytes but Intact TCRB Expression Define p110γδ$^{-/-}$ Thymi To determine the thymocyte population(s) most affected by the absence of PI3Kδ and PI3Kγ, flow cytometry analyses were performed to detect markers associated with thymocyte differentiation. Although the total number of CD4$^+$ and CD8$^+$ SP and DP cells were reduced overall, the absence of catalytic subunits had the greatest effect on the number of DP cells, typically the largest population of thymocytes in WT mice (FIG. 2A). In contrast, DN cells were the preponderant population in p110γ$^{-/-}$ thymi, as occurs, for instance, in RAG2$^{-/-}$ mice (FIG. 8). In the latter, TCRB selection cannot occur at the DN3 stage, resulting in thymocyte death by apoptosis. Although a percentage of the DN3 population (CD44$^-$CD25$^+$) increased in thymi of p110γ$^{-/-}$ mice, these cells were still capable of differentiating to the DN4 stage (CD44$^-$CD25$^-$) (FIG. 2B). The populations of DN3 and DN4 thymocytes developing in p110γ$^{-/-}$ mice, however, appeared to be phenotypically different from those of WT mice. Specifically, there appeared to be a continuum of DN3 to DN4 cells expressing gradually lower levels of CD25$^+$ T cells. Although there was some variation in the percentages of DN1 cells (1.07%-8.82%), a modest but reproducible increase in the percentages (but not the total numbers) of immature CD8$^+$ SP thymocytes bearing low-level surface TCRB was observed (FIG. 2D). These cells are the direct precursors of DP thymocytes. Importantly, the proportion of DN3 cells in p110γ$^{-/-}$ thymi that expressed TCRB protein was comparable to that of WT controls, as demonstrated by intracellular staining (FIG. 2C). Thus, unlike RAG-deficient mice, the depletion of DP cells lacking p110 catalytic subunits does not appear to have resulted from a failure to undergo TCRB selection. The few remaining DP cells, however, still were capable of differentiating into TCR B$^{high}$ SP T cells, suggesting that positive selection may be intact (FIG. 2D-E). In contrast, the reconstitution of lethally irradiated p110γ$^{-/-}$ mice with WT FLC restored the proportions of DN, DP, and SP populations to those observed for WT littermates, suggesting that the combined activities of PI3Kδ and PI3Kγ in cells other than thymocytes are not critical for their overall development. Of note, this dramatic alteration in DP and DN thymocyte populations was not observed in p110δ- or p110γ-deficient animals (FIG. 7).

Example 4

Figure 3A:
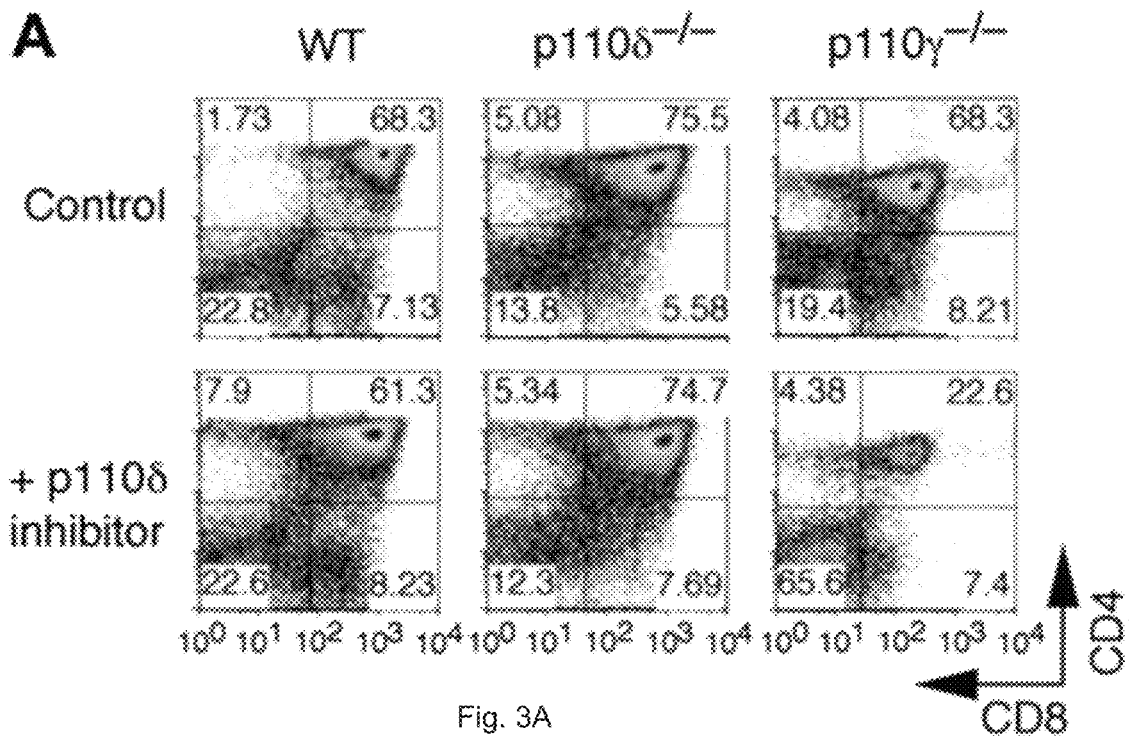
FIGS. 3A-3B show the contribution of p110γ and p110δ activity in thymocyte development in vitro.
Figure 3B:
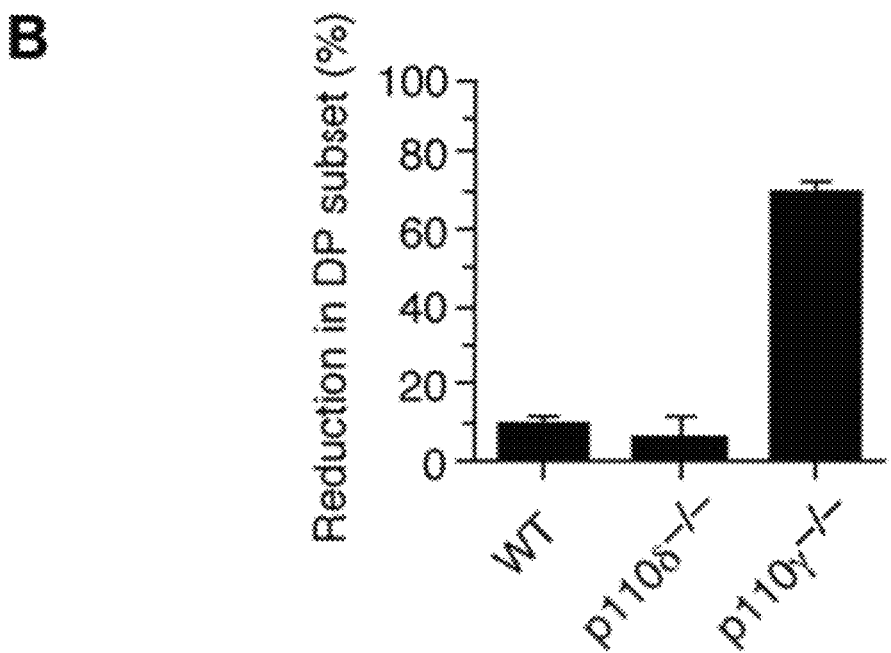

Absence of PI3Kγ and PI3Kδ Activity Results in Depletion of DP Thymocytes In Vitro To confirm the in vivo observations and thus demonstrate that a deficiency in PI3Kδ contributed to the reduction in the DP thymocyte population, day 14.5 fetal thymi were harvested from WT, p110δ$^{-/-}$, and p110γ$^{-/-}$ mice and were cultured in the presence of either p110δ-selective inhibitor IC87114 or vehicle control. Blockade of p110δ activity, in combination with genetic deletion of its gamma counterpart, resulted in a 69.2%±2.7% (mean±SE) reduction in the population of CD4$^+$CD8$^+$ DP thymocytes (FIG. 3A-B). Identical treatment of thymic cultures derived from p110δ$^{-/-}$ or WT control mice yielded a 10% or lower decrease in DP cells. Thus, blockade of p110δ function in p110γ$^{-/-}$ mice in lieu of its genetic deletion resulted in a similar alteration in the proportion of DP cells, as observed in p110γ$^{-/-}$ animals (FIG. 2B). Surprisingly, no significant alterations in the percentages of DN or DP populations were detected in p110γ$^{-/-}$ fetal thymi, suggesting that this class 1b PI3K does not have a major effect on thymocyte development under in vitro culture conditions. Moreover, the use of fetal thymic organ cultures excludes the possibility of glucocorticoid-induced thymocyte apoptosis as the primary mechanism for the observed reduction in cell numbers in vivo (Ashwell et al., 2000).

Example 5

Increased Apoptosis in p110γδ$^{-/-}$ DP Thymocytes

Figure 4A:
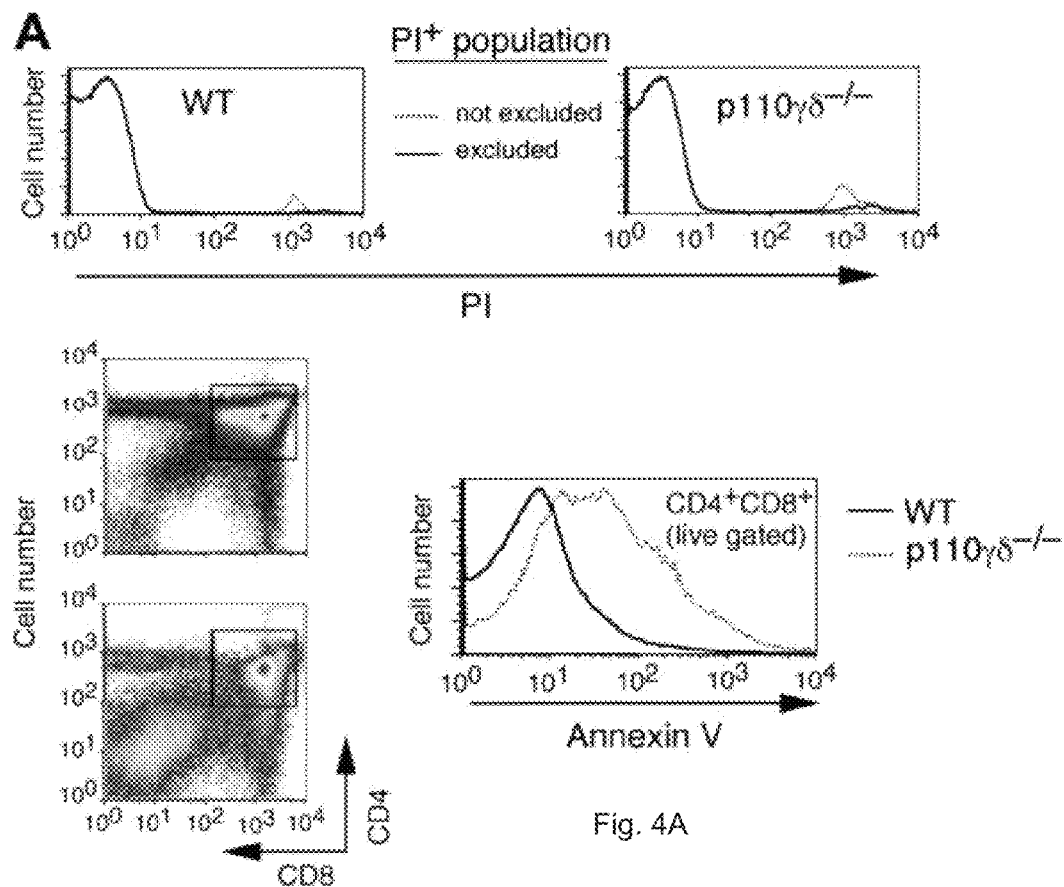
FIGS. 4A-4B show that DP thymocytes lacking p110γ and p110δ are prone to apoptosis.
Figure 4B:
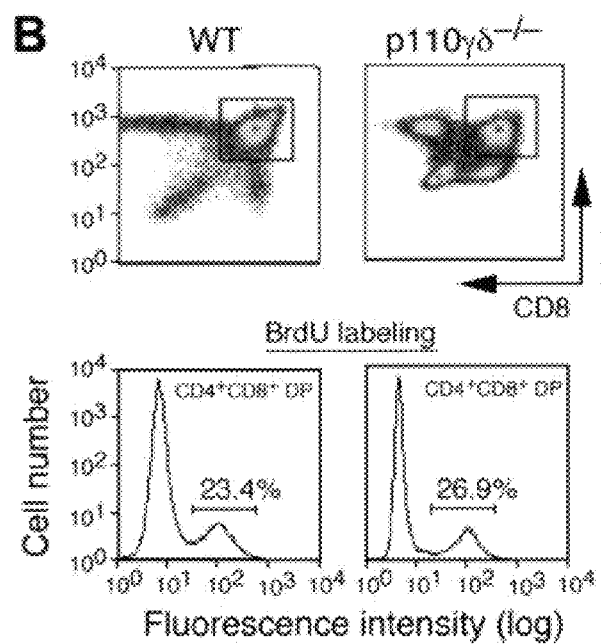

It is conceivable that the observed reduction in the DP thymocyte population in p110γ$^{-/-}$ mice may result from either an increase in cell death or an overall decrease in the generation of this subset of cells. To determine whether this reduced cellularity might have reflected the former, this population of cells was evaluated for evidence of enhanced apoptosis. Flow cytometry analysis of PI-negative DP thymocytes revealed a 42%±6.1% increase in annexin V staining compared with WT littermates (FIG. 4A). Moreover, DP thymocytes from p110γδ$^{-/-}$ mice showed decreased survival in in vitro cultures compared with WT or DP cells lacking p110γ or p110δ alone (data not shown). On the other hand, in vivo labeling of thymocytes with BrdU revealed no differences in the rate of generation of p110γδ$^{-/-}$ or WT DP 20 hours after the BrdU pulse (25.4±5.7 vs 23.3±0.2, respectively), indicating that PI3Kγ and PI3Kδ activity is not essential for the generation of DP thymocytes (FIG. 4B), (Penit et al., 1995). Rather, these results suggest that one major function of class 1 PI3Ks is to protect DP thymocytes from enhanced cell death, which, in turn, has a direct effect on thymic cellularity.

Example 6

Figure 5A:
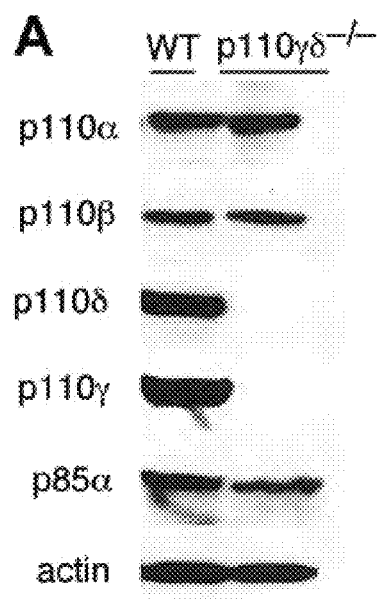
FIGS. 5A-5C show the evaluation for p110δ protein and activity in thymocytes.
Figure 5B:
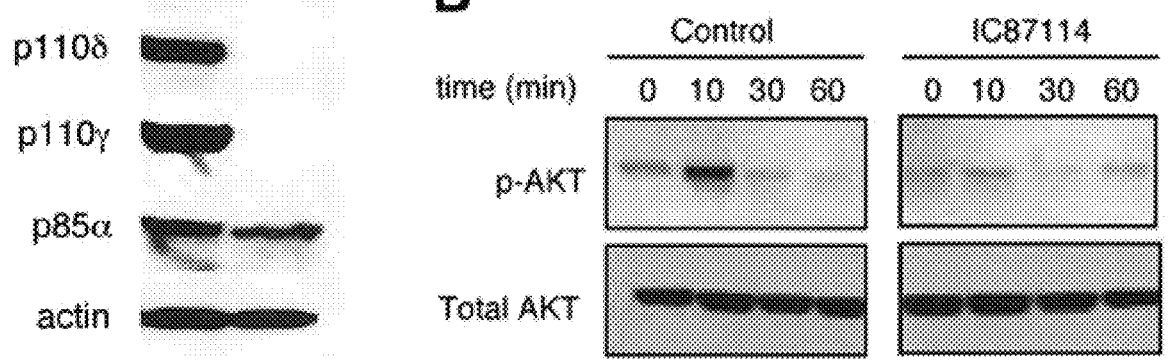
Figure 5C:
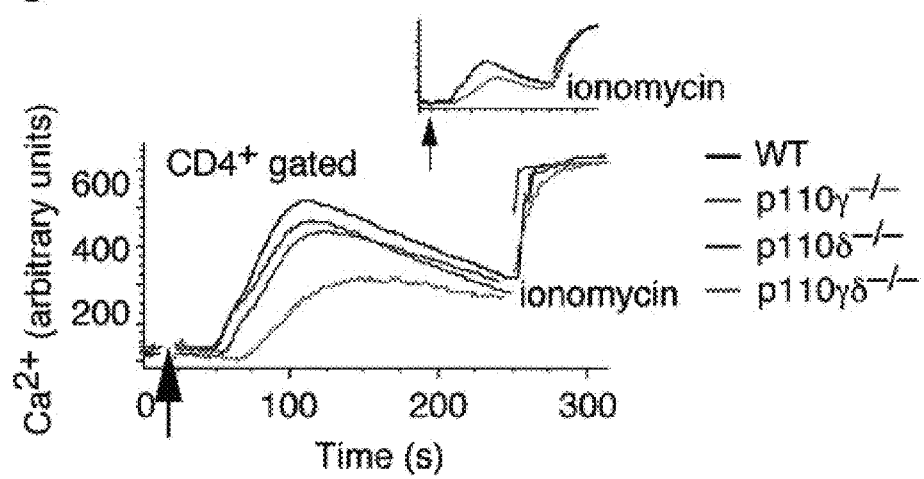

Akt/PBK Phosphorylation and Ca$^{2+}$ Flux in the Absence of PI3Kδ and PI3Kγ Function Western blot analysis revealed the presence of a p110δ catalytic subunit and other class 1a and class 1b isoforms in thymocytes harvested from WT control mice (FIG. 5A). Importantly, the expression pattern of p110α and p110β remained unchanged in thymocytes harvested from p110γ$^{-/-}$ mice, with the exception of a small reduction in levels of the p85a regulatory subunit. The latter, however, is consistent with that previously reported for B cells obtained from mice lacking p110δ alone (Clayton et al., 2002). To demonstrate that p110δ is functional in thymocytes, TCR-induced phosphorylation of the PI3K target Akt/PKB was used as an indirect measure of its activity. To isolate PI3Kδ activity, thymocytes from p110γ$^{-/-}$ mice were harvested and pretreated with vehicle control or with the p110δ-specific inhibitor IC87114 before TCR cross-linking. The results indicate that PI3Kδ does contribute to antigen receptor-induced activation of Akt/PKB in thymocytes because the phosphorylated form of this protein kinase was not detected in p110γ$^{-/-}$ cells treated with IC87114 under the assay conditions used (FIG. 5B). Optimal TCR-induced Ca$^{2+}$ flux required the activity of both class 1 PI3K isoforms (FIG. 5C). Given that the proportion of cells capable of responding to TCR cross-linking in doubly-deficient thymi was different from that of its WT counterpart because of a larger proportion of DN cells in the former, Ca$^{2+}$ flux in DP cells sorted from p110γδ$^{-/-}$ mice was also evaluated. Results indicate the persistence of this attenuated response, implicating both PI3Kδ and PI3Kγ as important mediators of antigen receptor signals in DP thymocytes (FIG. 5C, inset).

Example 7

Figure 6D:
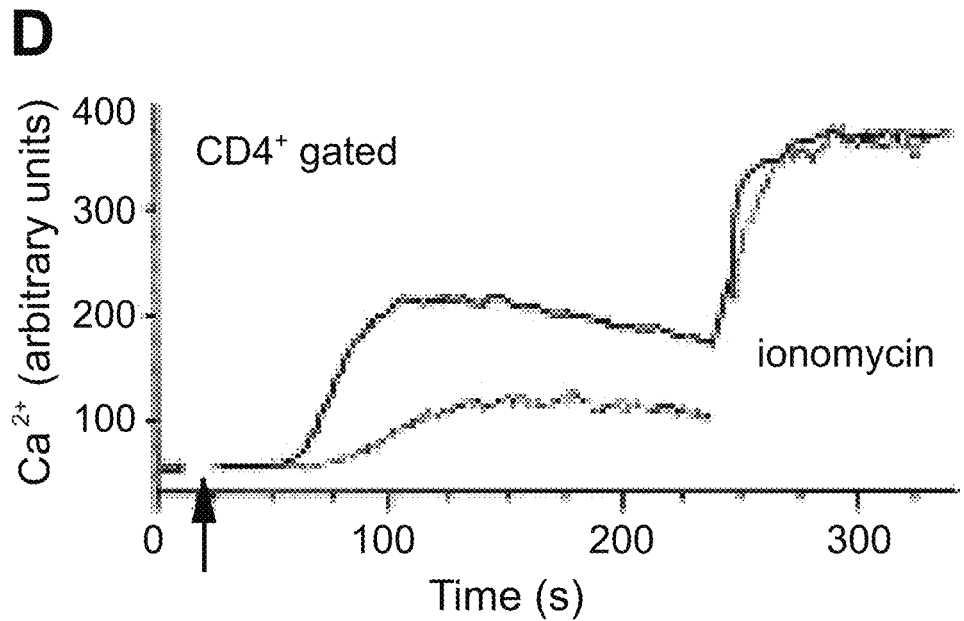
Figure 6E:
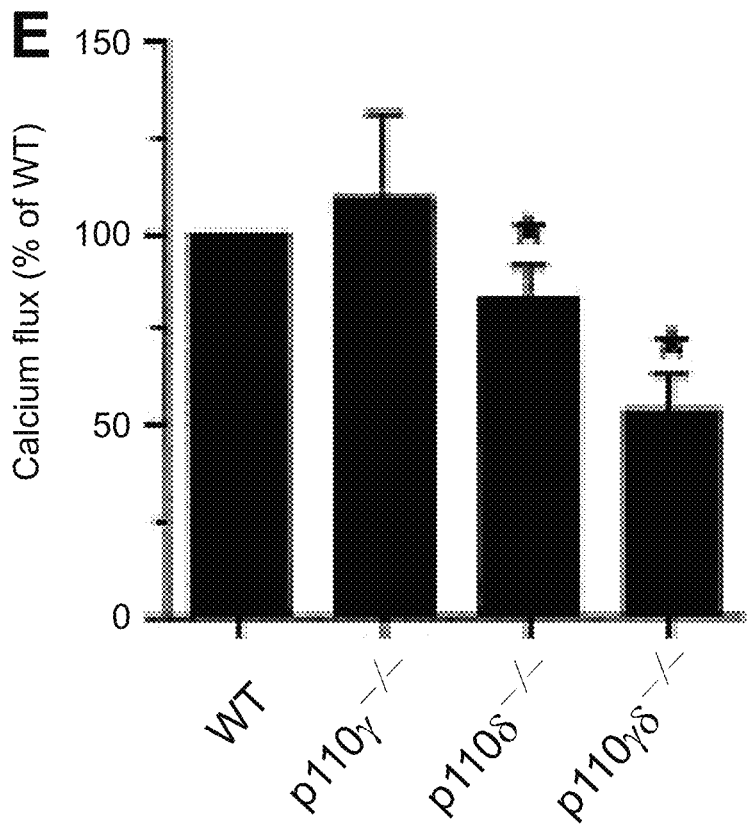

Effect of PI3Kδ and PI3Kγ Deficiency on T-Cell Numbers and Ca$^{2+}$ Mobilization The abnormalities observed in T-cell numbers and TCR-signaling associated with a deficiency in p110γ and p110δ catalytic subunits was not limited to the thymus but persisted in secondary lymphoid organs. In particular, a defect in DP cell development appears to have a direct effect on extra-thymic T-cell populations. Although the white blood cell count was similar among all genetic phenotypes tested, the total lymphocyte count was significantly reduced in p110γ$^{-/-}$ mice compared with WT littermates (2.9±1.1 K/μL vs 6.2±2.1 K/μL, respectively; FIG. 6A). Moreover, this corresponded to a 5-fold reduction in total number of circulating TCRB+ cells in the former. Similarly, T-cell populations in peripheral lymph nodes and spleen were diminished, as determined by immunohistology (FIGS. 6B-C). No such dramatic reduction of T cells was observed in secondary lymphoid organs in p110γ- or p110δ-deficient mice (data not shown). TCR-induced Ca$^{2+}$ flux in mature T cells also relied on the activity of class 1 PI3Ks, mirroring the defect observed in thymocytes. For example, a greater than 45% reduction in Ca$^{2+}$ flux in CD4$^+$ T cells from p110γδ$^{-/-}$ animals compared with WT littermates was observed (FIG. 6D-E). No defect was observed for p110γ-deficient cells, results consistent with those of a previous study (Sasaki et al., 2000). Moreover, only a modest reduction (approximately 15%) was noted for CD4$^+$ T cells from p110δ$^{-/-}$ mice. These results suggest that PI3Kγ and PI3Kδ must work in concert to ensure effective signaling through this antigen receptor in mature T cells.

Class 1 PI3Ks are essential for supporting innate and adaptive immune responses. By contrast, previous studies suggest they play a more limited role in thymocyte development and differentiation. Here, a novel defect in thymocyte development in mice that is dependent on the activities of 2 distinct subclasses of PI3Ks is disclosed. Genetic deletion of p110δ, in conjunction with its gamma counterpart, had a dramatic and unanticipated effect on thymus size, cellularity, and architecture. In particular, the combined absence of these 2 catalytic subunits resulted in a more than 4-fold reduction in the percentage and a 10- to 30-fold reduction in total numbers of cortical CD4$^+$CD8$^+$ DP thymocytes compared with WT littermates. Depletion of DP cells in p110γ$^{-/-}$ thymi was accompanied by a corresponding compensatory increase in percentages, but not total numbers, of DN thymocytes and a paucity in the number of mature CD4$^+$ and CD8$^+$ SP T cells found in blood and secondary lymphoid organs. Thus, the reduction in DP thymocytes is of importance as it relates to T-lymphocyte production because there may be insufficient quantities of this subset in p110γ$^{-/-}$ thymi to yield normal numbers of mature SP cells compared with WT animals (1.0×10$^6$±0.3 vs 109.6×10$^6$±22.6 DP cells, respectively).

Mechanistically, it is believed that the combined activity of PI3Kδ and PI3Kγ is critical to the survival of DP thymocytes in vivo. Indeed, given the inherent susceptibility of DP thymocytes to programmed cell death, presumably because of the down-regulation of the anti-apoptotic Bcl-2 protein at this stage of development, this population would be particularly vulnerable to the loss of survival signals generated by class 1 PI3Ks. In this context, an anti-apoptotic role has been indicated by the immunologic consequences of constitutive PI3K signaling that occurs in the absence of the tumor-suppressor gene PTEN, a phosphatase that converts PIP3 to PIP2. Selective deletion of PTEN in murine T cells not only results in uncontrolled proliferation of this lymphocyte subset, it leads to autoimmunity that is thought to be a consequence of impaired programmed cell death in the thymus (Penit et al., 1995). Thus, the ability to demonstrate that class 1 PI3Ks do indeed participate in PIP3 generation in thymocytes was central to this hypothesis (FIG. 5B). Further evidence in support of this claim is provided by annexin V staining. A significant percentage of DP cells in p110γ$^{-/-}$ thymi were annexin V-positive, a marker indicative of apoptosis, unlike that of WT and single null animals. Moreover, the ability to reproduce this in vivo abnormality in thymocyte development by exogenously blocking the activity of PI3Kδ in cultured fetal thymi harvested from E14 p110γ$^{-/-}$ embryos suggests an inherent defect in thymocyte signaling. Thus, a role for external factors such as a potential elevation in glucocorticoid levels in p110γδ$^{-/-}$ animals in this process was excluded.

Although the activity of PI3Kδ and PI3Kγ is involved in maintaining DP thymocyte survival, it is conceivable that they could participate in TCRB-selection. During normal development, TCRB chain gene rearrangement and expression reaches completion at the DN3 stage, permitting the formation of the pre-TCR complex. As a result, DN3 thymocytes can activate several signaling pathways, including lck/fyn and ZAP-70/Syk tyrosine kinases, SLP-76 and LAT linker proteins, Vav-family GEFs, and PLCγ1 phospholipase, that collectively mediate the transition of these cells to the CD4$^+$CD8$^+$ DP stage (Xu et al., 1995; Collins et al., 1997; Jordan et al., 2003; Kong et al., 1998; Reynolds et al., 2002). Consequently, mice lacking structural or signaling components of the pre-TCR complex exhibit a developmental block at the DN3 stage. In this context, PI3K activity has been implicated in Vav and PLCγ activation and Ca$^{2+}$ flux through direct (PIP3 binding to PH domains) and indirect (induction of Tec-family kinases) mechanisms (Okkenhaug et al., 2003; Okkenhaug et al., 2004). Indeed p110γ$^{-/-}$ thymocytes show impaired TCR-mediated Ca$^{2+}$ flux in vitro. Thus, a deficiency in p110δ and p110γ could result in the perturbation of DN to DP checkpoint through defective pre-TCR signaling. The data above, however, do not appear to support this mechanism because equal proportions of p110γ$^{-/-}$ compared with WT DN3 thymocytes express TCRB intracellularly. Moreover, pre-TCR complex-mediated events such as proliferative expansion, loss of CD25$^+$ expression (transition to the DN4 stage), and acquisition of CD8$^+$ and CD4$^+$ coreceptors (transition to DP stage) were readily visible in thymocytes from p110γ$^{-/-}$ mice. Thus, the resultant phenotype is clearly distinct from that associated with known defects in TCRB selection, such as RAG deficiency (FIG. 8). Importantly, animals lacking both PI3Kδ and PI3Kγ can still generate DP thymocytes at rates similar to those in WT mice, as indicated by BrdU-incorporation experiments. Despite this finding, it was noted that the populations of DN3 and DN4 thymocytes in p110γδ$^{-/-}$ mice were phenotypically different from those of WT mice because there appeared to be a continuum of DN3 to DN4 cells expressing gradually lower levels of CD25$^+$ T cells in the former. Although the mechanism for this abnormality is not completely understood, the most plausible explanation is that the gradual loss of CD25$^+$ cells simply mirrors Bcl-2 down-regulation and the subsequent necessity for class 1 PI3K-dependent survival signals.

Although the combined activities of PI3Kδ and PI3Kγ are essential for thymocyte development, it appears that either subclass is sufficient to maintain T-cell production. This potential redundancy in function may ensure that adequate levels of PIP3 are maintained to protect cells from proapoptotic stimuli. How these 2 PI3K subclasses, which are activated through distinct pathways, are linked through receptors (such as the TCR) that promote the development and survival of immature DP thymocytes remains to be determined. That said, it has been demonstrated that ligation of an ITAM-bearing receptor on cells, such as FcγRI, can result in the activation of class 1a and class 1b PI3Ks (Melendez et al., 1998). Moreover, it was speculated that the activation of p110γ, which typically occurs through G protein-coupled receptors, may involve the Tec family of tyrosine kinases, which have the capacity to physically interact with PIP3 and heterotrimeric G-protein subunits (Lewis et al., 2001). Such a scenario may hold true for T cells, because PI3Ks and Tec kinases are intricately linked in TCR-mediated signaling. For example, Tec kinases are required for the regulation of PLCγ activity and Ca$^{2+}$ signaling, an event that involves PI3Kδ (Okhenhaug et al., 2002). Thus, it is conceivable that in response to PI3Kδ activation or other class 1a isoforms, a Tec tyrosine kinase family member will become localized at the plasma membrane through interactions with PIP3, which in turn may recruit a heterotrimeric G-protein that could activate p110γ and thus enhance PIP3 production.

Example 8

Effects of Partial Inhibition of Class I PI3K on Immunological Tissues

Figure 9:
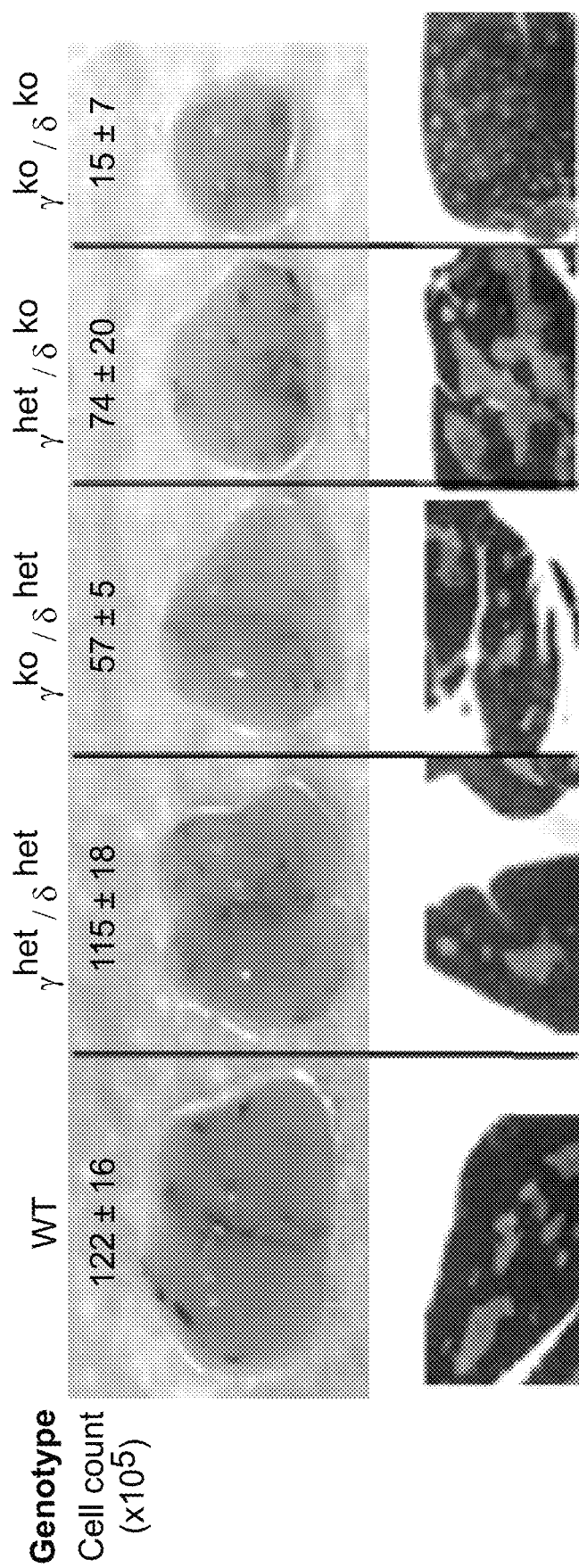
FIG. 9 shows the effect of the genetic deletion of p110γ and p110δ on thymus size and cellularity. Top row shows the size and cell counts of thymi of different PI3K genotypes. Bottom row shows the micrographs of hematoxylin and eosin-stained thymi. (Objective, magnification 40×4×/NA).

As set forth above, the genetic deletion of both p110γ and p110δ resulted in a significant reduction of thymus size and cellularity (about 8-fold). This deficiency also resulted in a lack of corticomedullary differentiation as compared to WT mice, indicating abnormal T cell development. Although p110γ$^{ko}$/δ$^{het}$ and p110γ$^{het}$/δ$^{ko}$ mice exhibited reduced thymus size and cell counts (2.1-fold and 1.6-fold, respectively), there was no obvious defect in corticomedullary differentiation (FIG. 9).

Figure 10A:
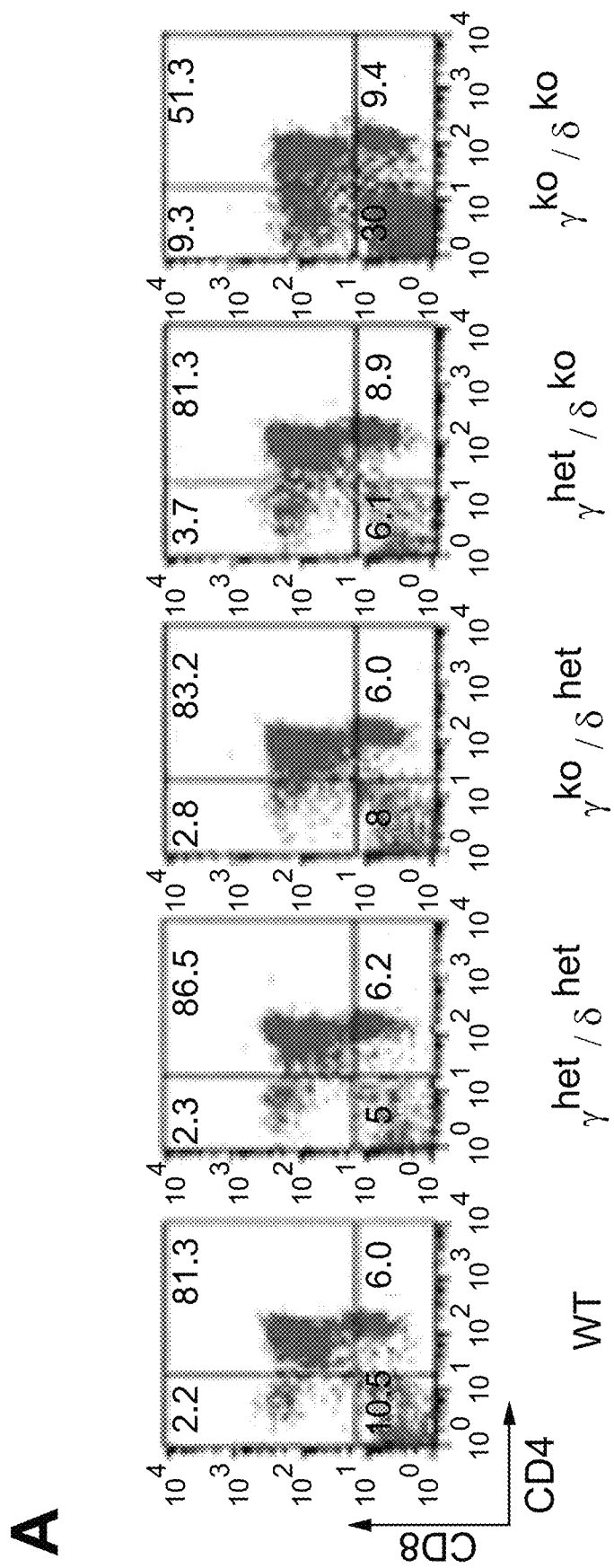
FIGS. 10A-10B show the effect of genetic deletion of p110γ and p110δ on CD4/CD8 DP thymocyte population.
Figure 10B:
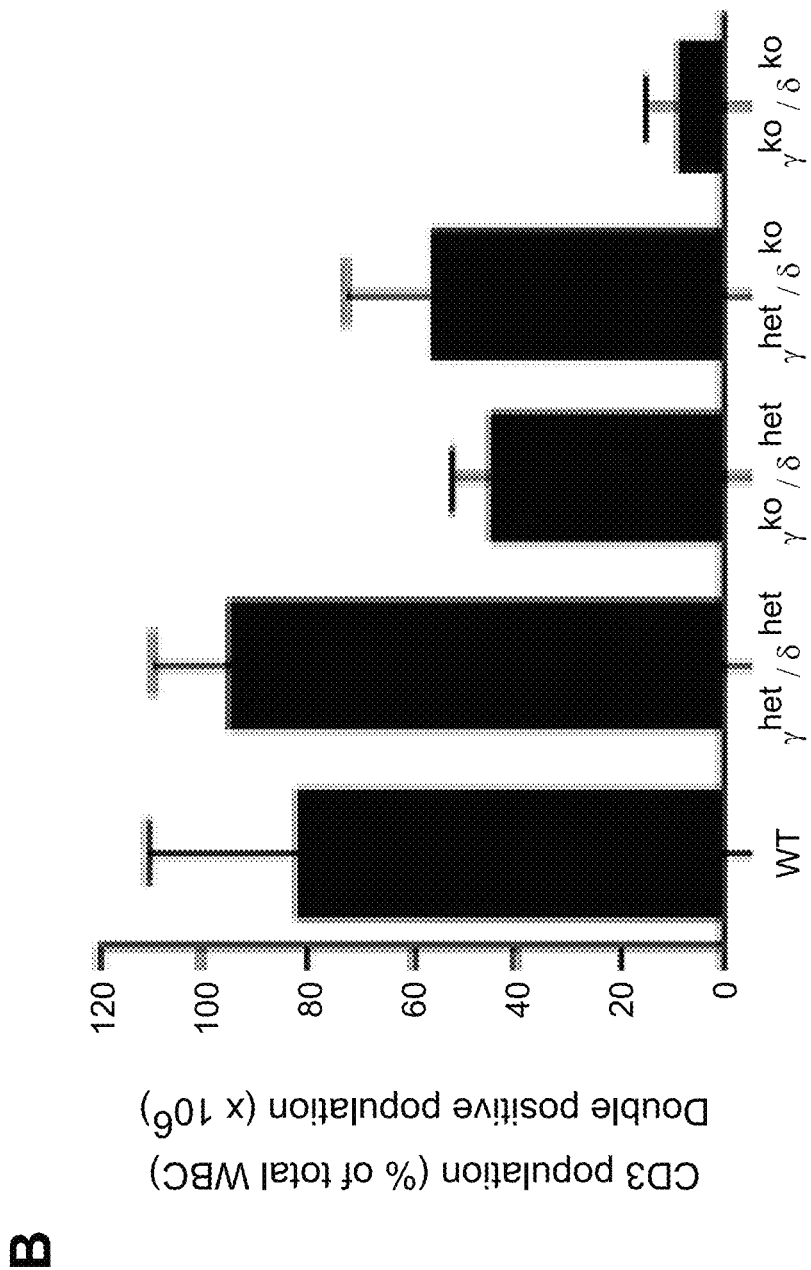

Flow cytometry was utilized to evaluate the expression of the cell surface markers CD4 and CD8 in order to track the development of thymocytes. The double-positive (DP) population, cells expressing both CD4 and CD8 in their second stage of development, was significantly reduced in mice deficient in both PI3Kγ and PI3Kδ (9-fold as compared to WT). By contrast, 50% PI3Kγ or PI3Kδ activity was sufficient to maintain the normal percentage of DP thymocyte population (FIG. 10A). There was, however, a significant reduction in total numbers of DP cells in p110γ$^{ko}$/δ$^{het}$ and γ$^{het}$/δ$^{ko}$ thymi as compared to WT (45±7 and 56±17 vs. 82±29, respectively; mean±SD) (FIG. 10B).

Figure 11:
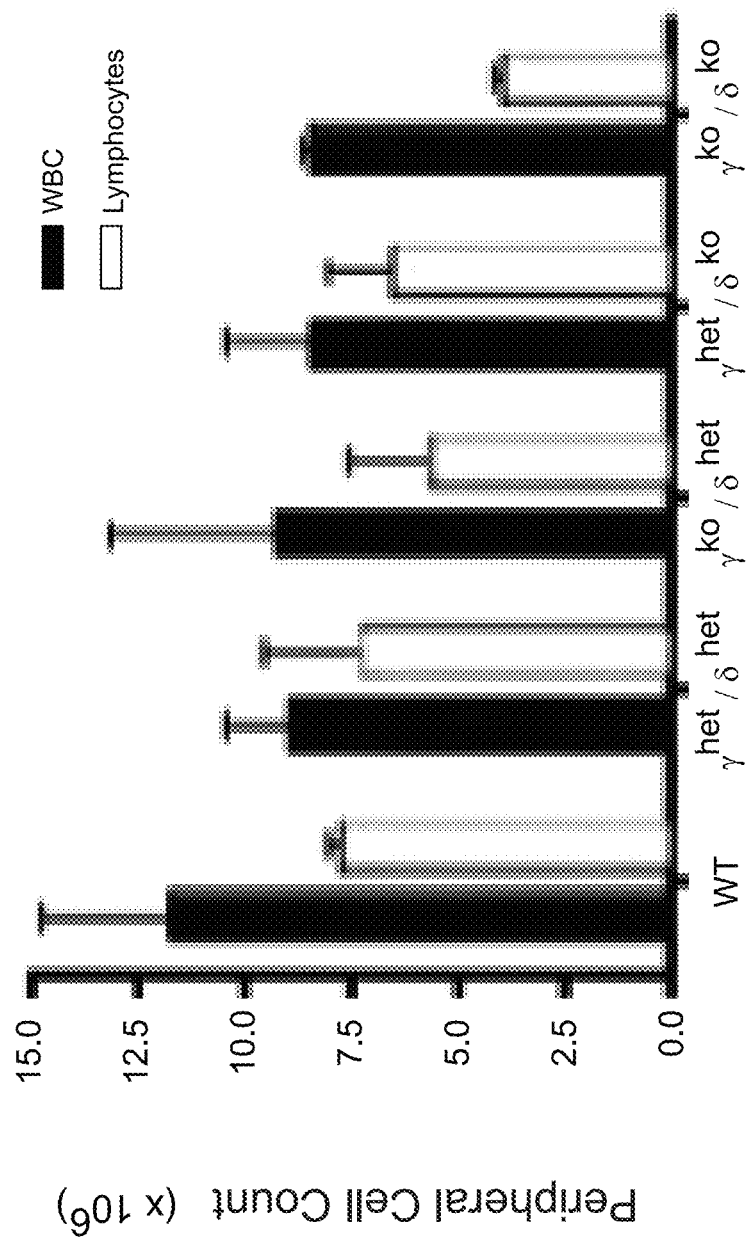
FIG. 11 shows the effect of genetic deletion of p110γ and p110δ on peripheral blood WBC counts. Total WBC and lymphocyte counts for each genotype (mean±SD) are shown. Data indicates an average of 3 independent experiments.
Figure 12A:
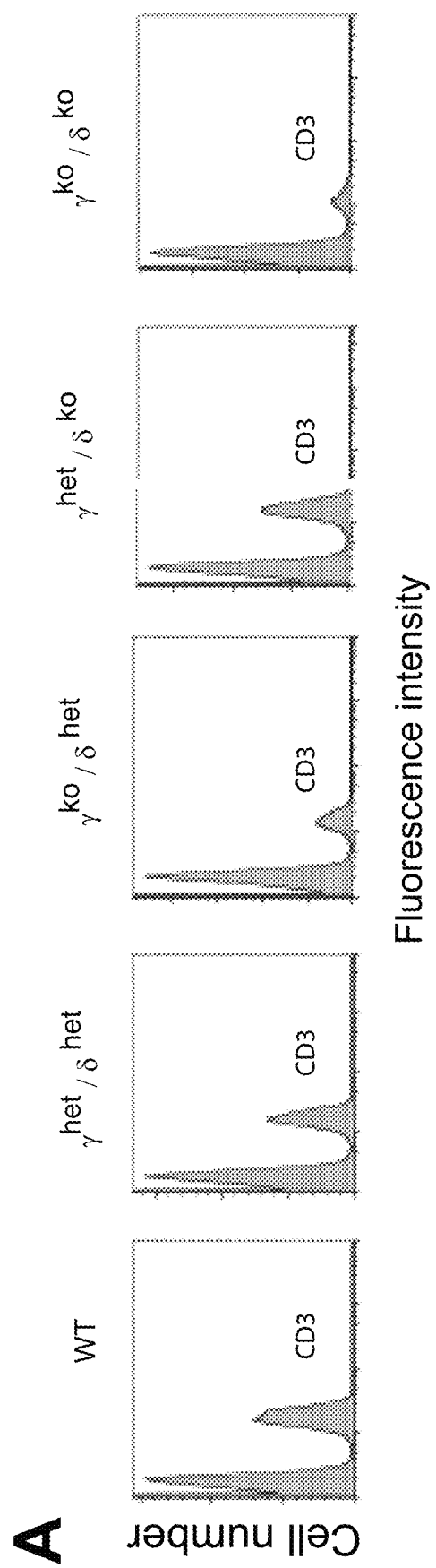
FIGS. 12A-12B show the effect of genetic deletion of p110γ and p110δ on CD3 cell count in peripheral blood.
Figure 12B:
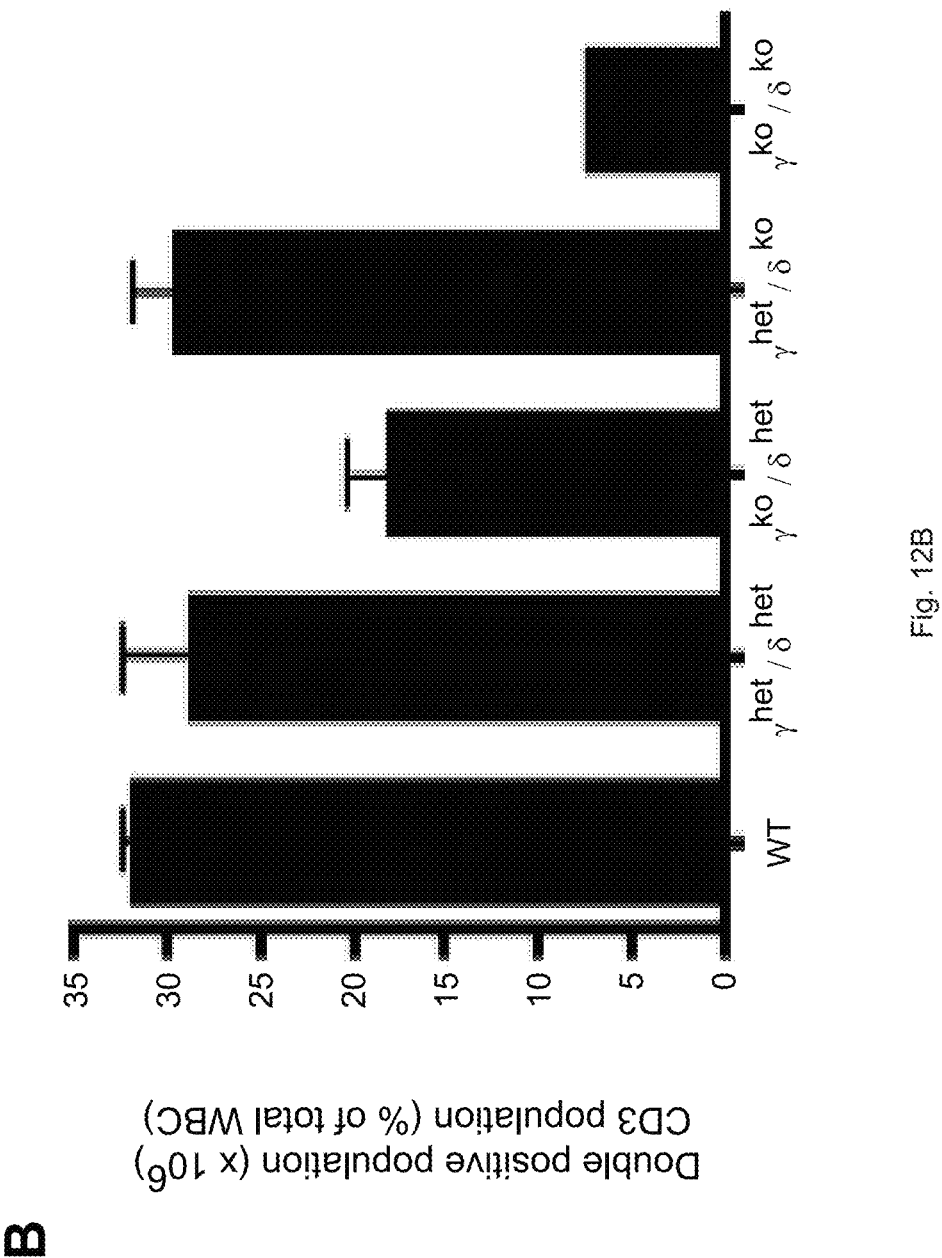
Figure 13:
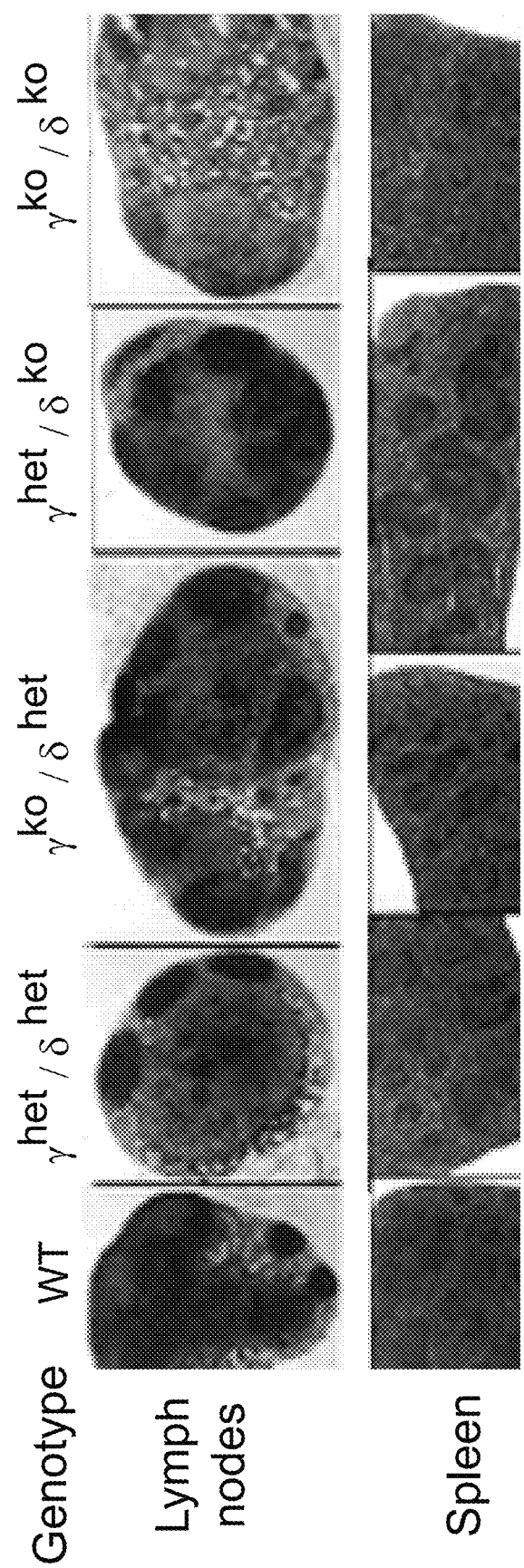
FIG. 13 shows the effect of genetic deletion of p110γ and p110δ on size and cellularity of spleen and lymph nodes. Top row shows the micrographs of hematoxylin and eosin-stained peripheral lymph node. (Objective, magnification 40×4×/NA 0.16). Bottom row shows the micrographs of hematoxylin and eosin-stained spleen. (Objective, magnification 40×4×/NA 0.16).

The observed defects in T cell numbers were not limited to the thymus as they were also seen in the peripheral blood of mice deficient in PI3K activity (FIG. 11). Total WBC counts were relatively unaffected; however, the number of circulating T cells as defined by CD3 positivity was reduced in γ$^{ko}$/δ$_{het}$ and γ$^{ko}$/δ$^{ko}$ mice (2.2-fold and 5.9-fold as compared to WT, respectively). No such reduction was seen in γ$^{het}$/δ$^{ko}$ despite a significant decrease in DP thymocytes (FIG. 12). Still, the tissue organization and structure of peripheral lymph nodes and spleen did not seem to exhibit any anatomical defects in all mice except γ$^{ko}$/δ$^{ko}$ animals (FIG. 13).

Thus, a partial reduction in both PI3Kγ and PI3Kδ activity can have a profound effect on T cell development, although not to the extent of complete absence in activity. In particular, PI3Kγ appears to play a more important role in this process than that of PI3Kδ, because peripheral blood from γ$^{het}$/δ$^{ko}$ mice did not exhibit as significant a reduction in the number of circulating T cells as their γ$^{ko}$/δ$^{het}$ counterpart. Blood and tissues from animals with 50% activity in both p110 isoforms showed no major changes as compared to WT. Therefore, the order of genotypes displaying the least effect to most effect on T cells is as follows: WT<γ$_{het}$/δ$^{het}$<γ$^{het}$/δ$^{ko}$<γ$^{ko}$/δ$^{het}$<γ$^{ko}$/δ$^{ko}$. Based on these findings, it can be concluded that a drug that inhibits 50% of p110γ and 100% of p110δ would result in the least consequential impact on the immune system. Determining the exact amount of PI3K activity necessary to maintain the immune system could culminate in safer and more effective treatment of inflammatory diseases and blood cancers.

Example 9

PI3Kγ or PI3Kδ can Support Malignant Transformation of T Cells

Deletion of the tumor suppressor gene PTEN in T cell progenitors drives the malignant transformation of these cells within the thymus of mice (Suzuki et al., 2001; Hagenbeek and Spits, 2008; Liu et al., 2010). Moreover, the resulting tumors possess similar genetic and biochemical aberrations associated with a subset of patients with T-ALL including hyperactivation of the PI3K/Akt signaling pathway (Maser et al., 2007; Guo et al., 2008). Because PI3Kγ and PI3Kδ play a role in T cell development, their contribution to tumor formation was assessed by crossing mice containing PTEN alleles floxed by the loxP Cre excision sites with Lck-cre transgenic animals (Lck/Pten$^{fl/fl}$) alone or together with those lacking p110γ (encoded by Pik3cg) and/or p110δ (encoded by Pik3cd) catalytic subunits. Consistent with previous studies, >85% of Lck/Pten$^{fl/fl}$ mice develop T-ALL and eventually succumb to the disease (median survival of 140 days), which was confirmed by flow cytometric analysis (FIGS. 14A and 14B). In contrast to PTEN null tumors of solid organs that have been reported to rely on PI3Kδ activity (Jia et al., 2008; Wee et al., 2008), tumorigenesis in the context of a deficiency of PTEN in T cell progenitors appears to be critically dependent on PI3Kγ and PI3Kδ. This is evidenced by the marked delay in the onset of disease and increased survival of Lck/Pten$^{fl/fl}$; Pik3cg$^{-/-}$; pik3cd$^{-/-}$ triple mutant mice (TKO) as <20% of animals succumb to T-ALL by 220 days.

However, the activity of either isoform alone was sufficient to promote tumor formation, yielding similar median survival times for Lck/Pten$^{fl/fl}$; Pik3cg$^{-/-}$ and Lck/Pten$^{fl/fl}$; Pik3cd$^{-/-}$ mice (175 days versus 178 days, respectively). Comparable percentages of these animals developed and died of T-ALL (65% versus 64%, respectively) and tumors had evidence of activation of the PI3K/Akt signaling pathway, albeit much reduced as compared to those from Lck/Pten$^{fl/fl}$ animals (FIG. 14C). However, there was no evidence of over-expression of any Pik3c isoform in thymic tumors (FIG. 14D).

Figure 15A:
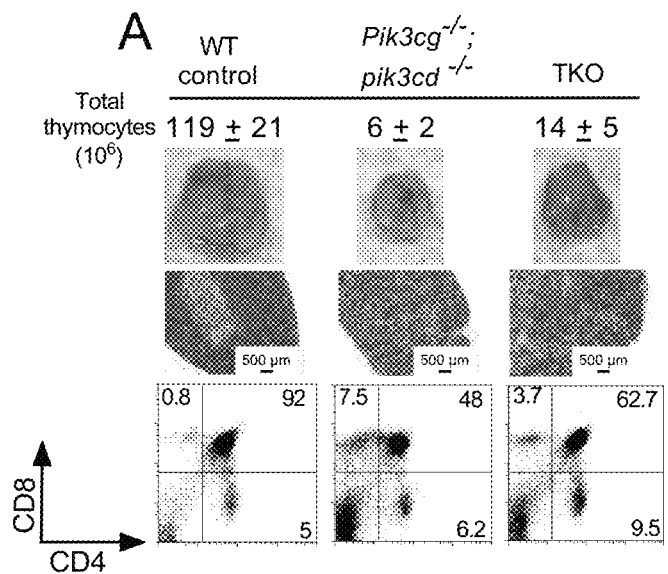
FIGS. 15A-15E show that persistence of cellular and structural defects in thymi is associated with a combined deletion of p110γ/δ and PTEN.
Figure 15B:
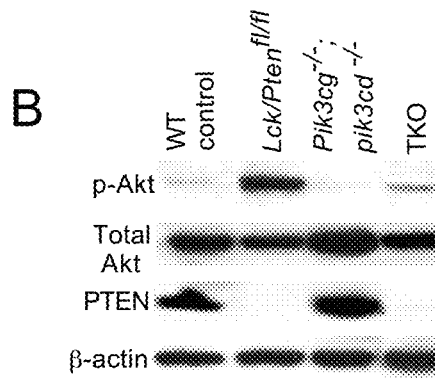
Figure 15C:
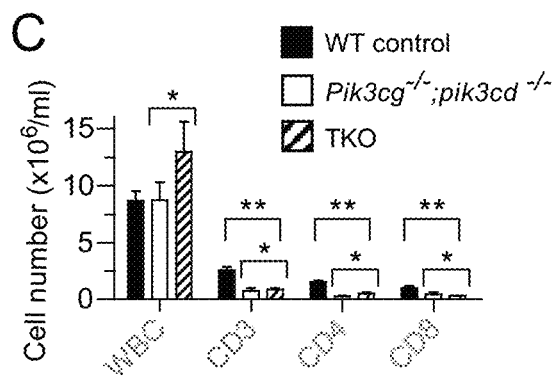
Figure 15D:
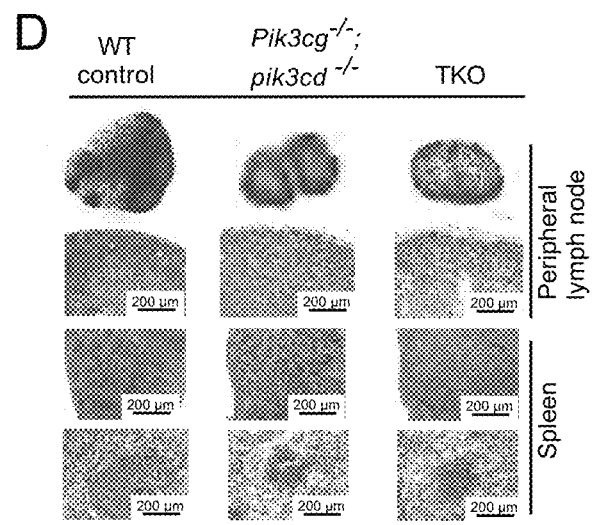
Figure 15E:
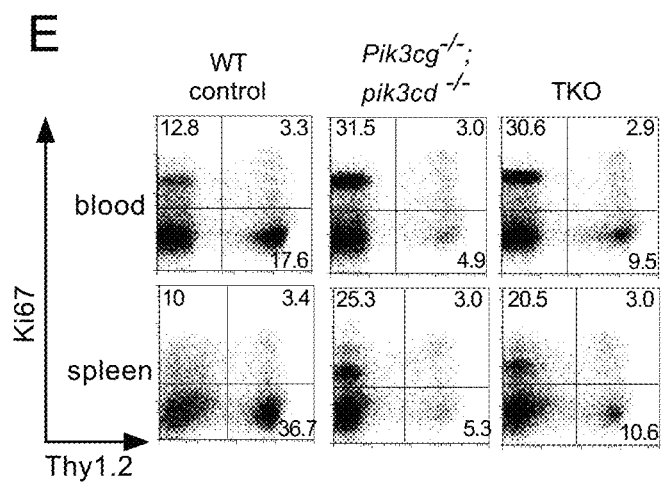

Further evidence demonstrating that it is the unleashed activities of PI3Kγ and PI3Kδ that provide the signals necessary for the development of T-ALL is suggested by the continued reduction in thymus size and cellularity in 6 week old TKO mice (FIG. 15A). Although absence of PTEN should permit unrestricted activity of all four class I PI3K isoforms, it appears that PI3Kα and PI3Kβ cannot adequately compensate for their gamma and delta counterparts as evidenced by the persistent diminution in the total number of CD4$^+$CD8$^+$ double positive thymocyte population and near basal levels of phosphorylated Akt (Ser473) as compared to mice deficient in PTEN alone (FIGS. 15A and 15B). Cellular alterations associated with p110γ/δ double deficiency also persisted in the peripheral blood and in secondary lymphoid organs of TKO mice and included a paucity of CD3$^+$ T cells (FIGS. 15C and 15D). No active tumor was found in peripheral blood or spleen of the surviving animals at about 7 months of age as determined by absence of staining for the proliferation marker Ki67 on Thy1.2 positive cells (FIG. 15E).

Example 10

Effect of PI3Kγ/PI3Kδ Dual Inhibition on Thymocyte Signaling and Development

In order to ascertain whether PI3Kγ and PI3Kδ are also required for tumor maintenance and can be targeted therapeutically in T-ALL, a small molecule that preferentially inhibits the function of both p110γ and p110δ catalytic domains was generated. This small molecule was designated CAL-130 (FIG. 16A). IC$_{50}$ values of this compound were 1.3 nM and 6.1 nM for p110δ and p110γ, respectively, as compared to 115 nM and 56 nM for p110α and p110β.

Figure 21A:
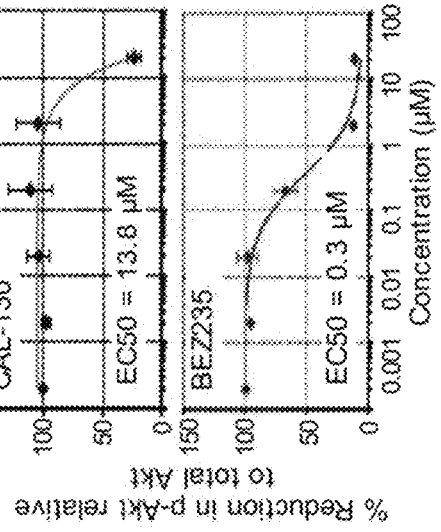
FIGS. 21A-21C show an inhibitory profile of CAL-130.

Importantly, this small molecule does not inhibit additional intracellular signaling pathways (i.e. p38 mitogen-activated protein kinase or insulin receptor tyrosine kinase) that are critical for general cell function and survival (Tables 1 and 2). To demonstrate that CAL-130 can block the activities of both PI3Kδ and PI3Kγ in thymocytes, its ability to prevent phosphorylation of Akt (Ser473) and calcium flux in response to TCR-cross-linking were evaluated. As set forth above, the combined activities of these two class I PI3K isoforms are necessary for phosphorylation of this protein kinase in this cell population (Swat et al., 2006). Consistent with these results, CAL-130 treatment of thymocytes harvested from 6 week old wild type animals prevented TCR induced Akt phosphorylation and attenuated calcium flux to levels observed for their Pik3cg$^{-/-}$; pik3cd$^{-/-}$ counterparts (FIGS. 16B, 16C, and 21A).

Figure 21B:
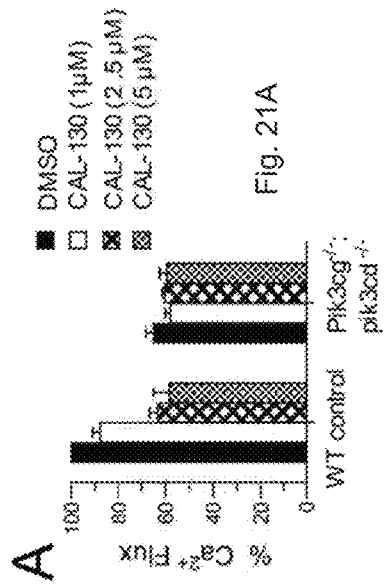
Figure 21C:
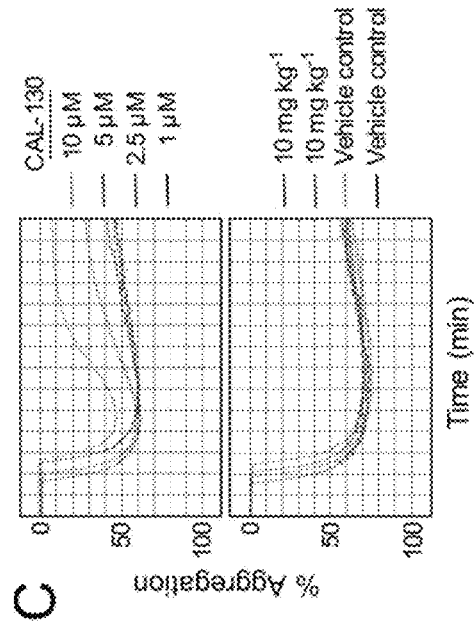

To assess the in vivo efficacy of the inhibitor, its effects on thymi of 6 week old mice were determined, specifically for its ability to recapitulate the phenotype observed when both p110γ and p110δ are deficient. Animals received 10 mg kg$^{-1}$ of the inhibitor orally, which was sufficient to maintain plasma concentrations of 0.33±0.18 μM at the end of 8 hours (FIG. 16D). Notably, this dose did not affect either plasma glucose or insulin levels in contrast to the metabolic perturbations associated with tissue specific deficiencies in p110α and p110β (FIGS. 16E and 16F) (Jia et al., 2008; Sopasakis et al., 2010). CAL-130 was also found to have a limited ability to impair PDGF-induced activation of PI3Kα as compared to the pan-PI3K/mTOR inhibitor BEZ235 (FIG. 21B). Similarly, platelets harvested from Pik3cd$^{-/-}$; pik3cd$^{-/-}$ mice 2 hours post administration of CAL-130 had no obvious defect in ADP-mediated platelet aggregation, a process known to rely predominantly on PI3KP (FIG. 21C) (Jackson et al., 2005). However, CAL-130 treatment (10 mg kg$^{-1}$ every 8 hours) for a period of 7 days markedly affected the size, cellularity, and overall architecture of the thymus faithfully reproducing the phenotype associated with Pik3cd$^{-/-}$; pik3cd$^{-/-}$ mice (FIG. 16G). In particular, there was a 18-fold reduction in total thymocyte number in comparison to controls, which was primarily due to the loss of DP population (FIG. 16H). These observations are consistent with the ability of CAL-130 to preferentially block the function of both PI3Kγ and PI3Kδ.

Example 11

Figure 17A:
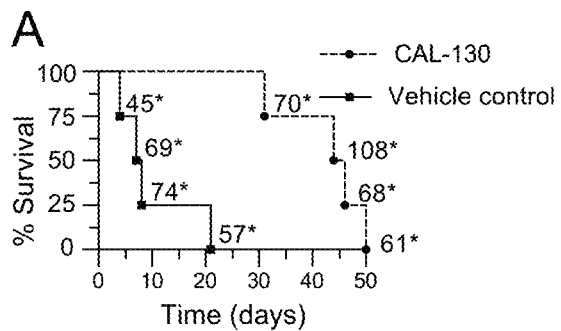
FIGS. 17A-17E show that combined inhibition of p110γ and p110δ reduces tumor burden and increases survival in animals with PTEN null T-ALL.

Antileukemic Effects of Pharmacological Inhibition of PI3Kγ and PI3Kδ in PTEN Null T-ALL Tumors in Mice The clinical significance of interfering with the combined activities of PI3Kγ and PI3Kδ was determined by administering CAL-130 to Lck/Pten$^{fl/fl}$ mice with established T-ALL. Candidate animals for survival studies were ill-appearing, had a WBC above 45K μl$^{-1}$, evidence of blasts on peripheral smear, and a majority of circulation cells (>75%) staining double positive for Thy1.2 and Ki-67. Mice received an oral dose (10 mg kg$^{-1}$) of the inhibitor every 8 hours for a period of 7 days and were then followed until moribund. Despite the limited duration of therapy, CAL-130 was highly effective in extending the median survival for treated animals to 45 days as compared 7.5 days for the control group (FIG. 17A).

Figure 17B:
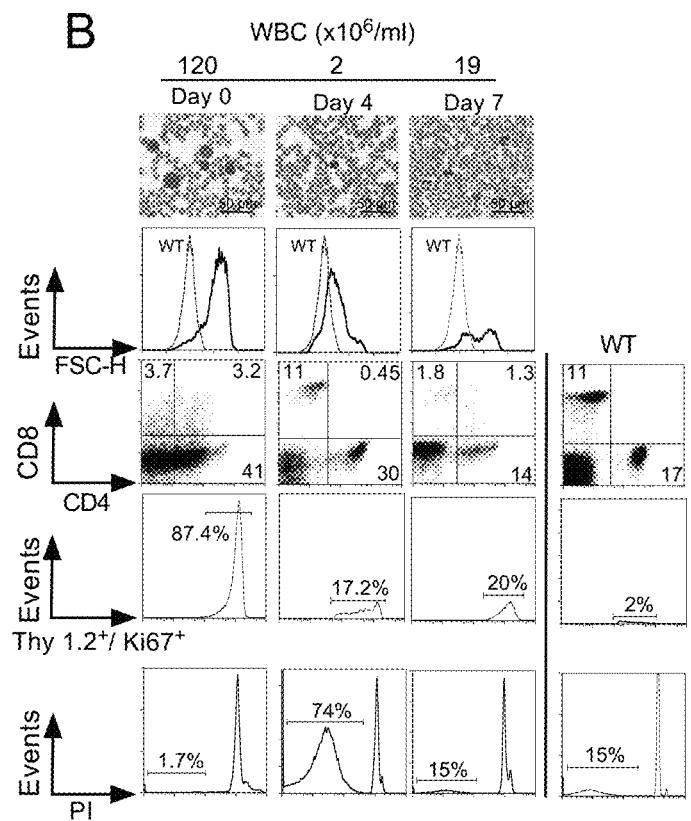
Figure 17C:
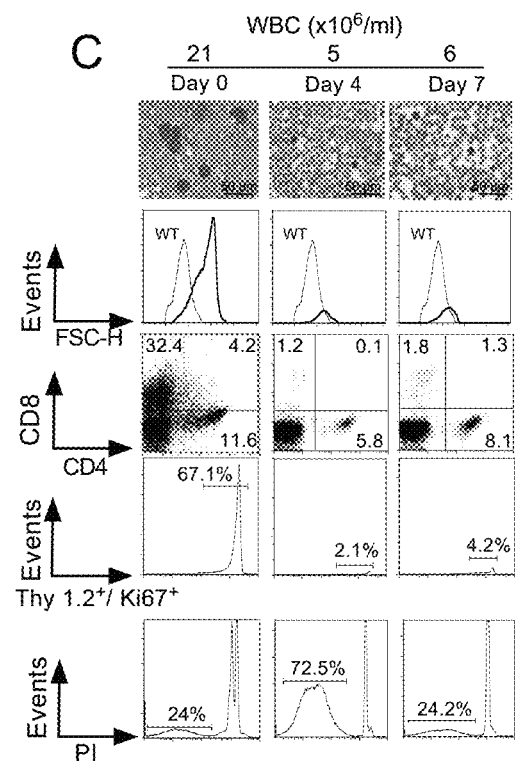
Figure 22A:
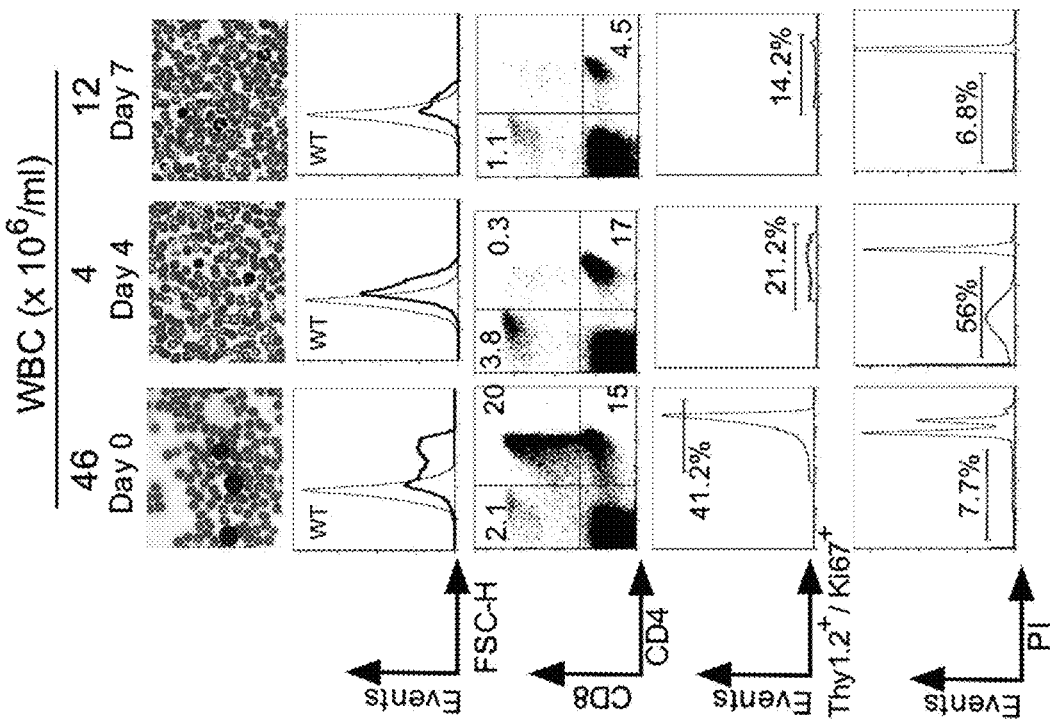
FIGS. 22A-22D show peripheral blood smears and flow cytometric profiles for diseased Lck/Pten$^{fl/fl}$ mice just before and after treatment with either CAL-130 (FIGS. 22A-C) or IC87114 (FIG. 22D) at the indicated time points. Forward scatter (FSC) and Ki67 staining are indicators of cell size and proliferation, respectively. Apoptosis was detected by assessing the sub-G0 population after PI staining.
Figure 22B:
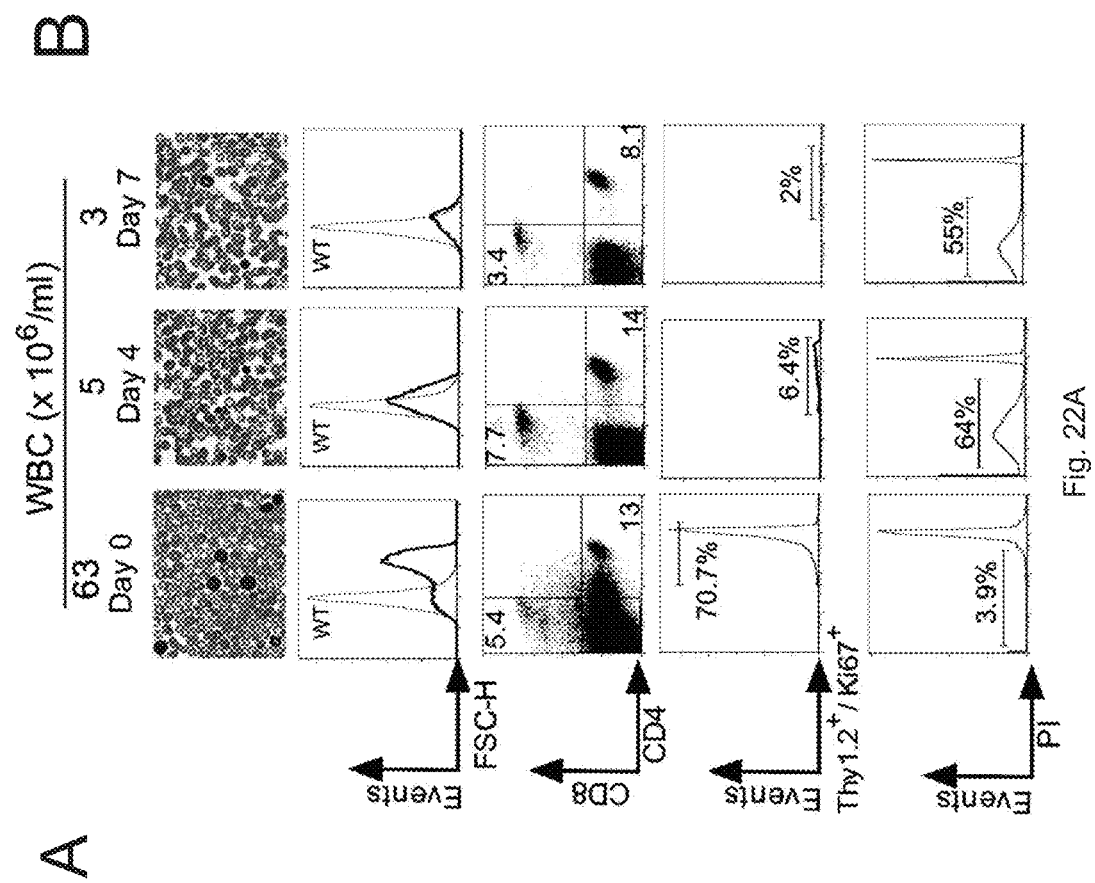
Figures 22C, 22D:
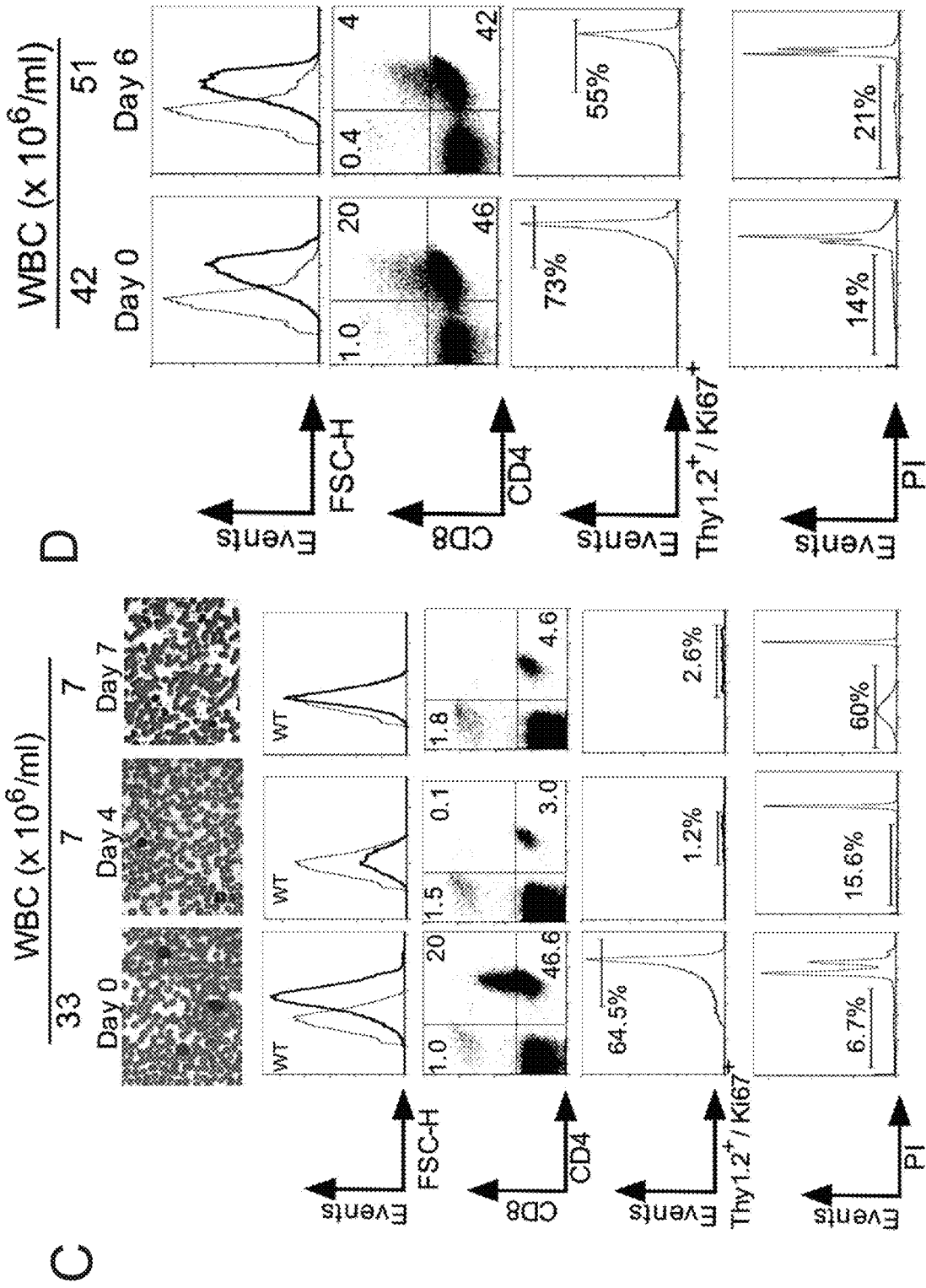
Figure 23I:
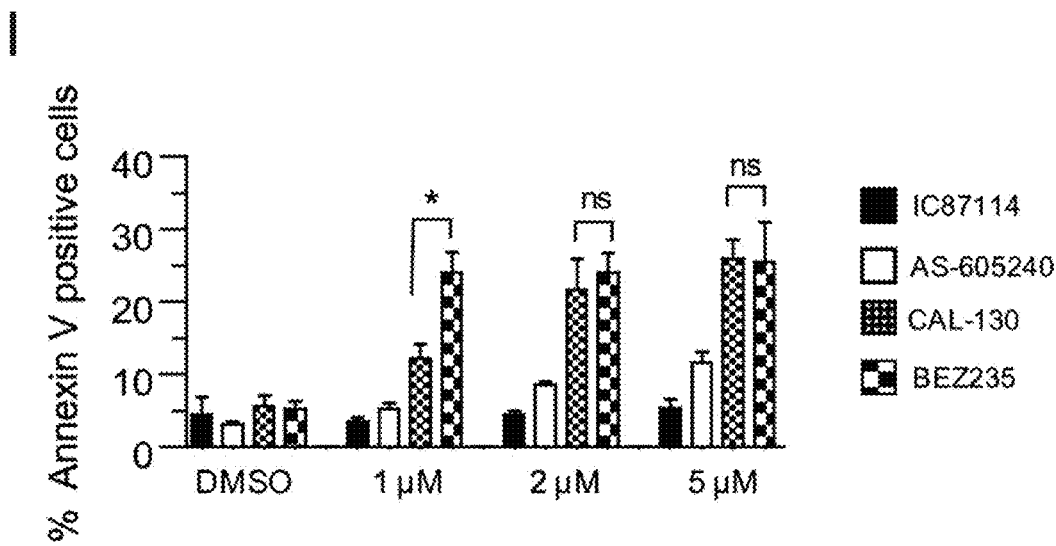
Figure 23J:
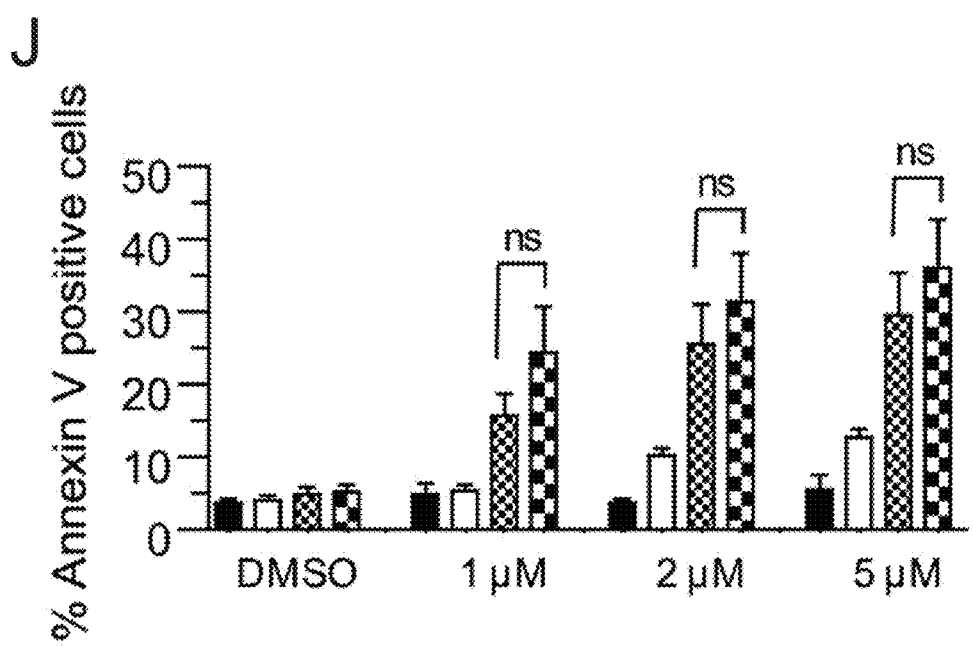

To determine the effect of CAL-130 on disease burden, sequential blood counts and peripheral smears as well as flow cytometric analyses were performed on Lck/Pten$^{fl/fl}$ mice pre- and post-administration of the inhibitor (FIG. 17B; FIGS. 22A-22C). All animals showed a dramatic reduction in WBC by day 4 reflected in the loss of the highly proliferative blast population (Thy1.2/Ki-67 double positive, high FSC-H), which remained at low levels for the duration of treatment. Moreover, both CD4 single positive and CD4/CD8 double positive T-ALL responded to CAL-130, which corresponded with an increase in apoptosis detected as sub-G0 population after propidium iodide (PI) staining on days 4 through 7. Treatment of diseased Lck/Pten$^{fl/fl}$; Pik3cg$^{-/-}$ mice but not their Lck/Pten$^{fl/fl}$ counterparts with the PI3Kδ selective inhibitor IC87114 (10 mg kg$^{-1}$ every 8 hours) produced similar results, confirming the critical reliance of PTEN null tumors on the combined activities of PI3Kγ and PI3Kδ (FIG. 17C; FIG. 22D).

Figure 17D:
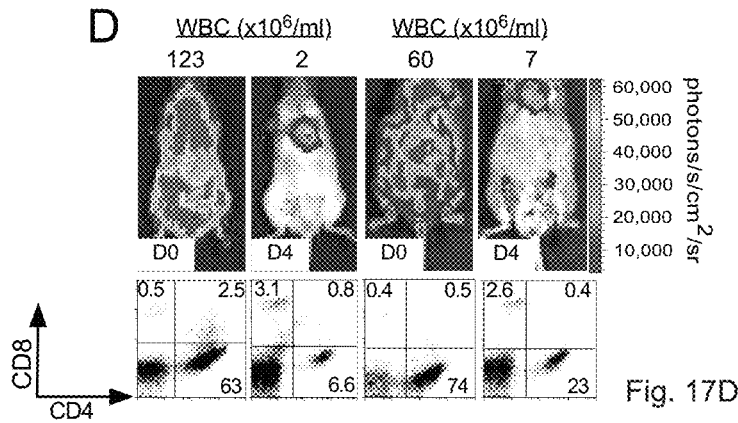
Figure 17E:
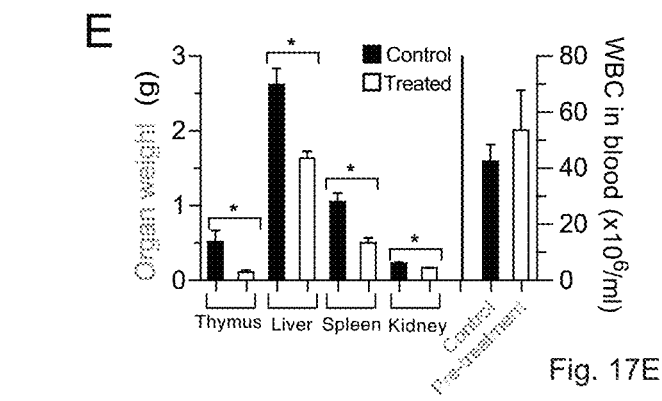

Further evidence to support the ability of CAL-130 to reduce tumor burden was obtained by bioluminescent imaging. Pten$^{fl/fl}$ mice were crossed with a strain in which a luciferase cDNA, preceded by a LoxP-stop-LoxP cassette, was introduced into the ubiquitously expressed ROSA26 locus (Safran et al., 2003). Progeny were then crossed with Lck-cre transgenics to delete Pten in T cell progenitors and induce expression of luciferase (Lck/Pten$^{fl/fl}$; Gt(ROSA) 26Sor$^{tm1(Luc)Kael}$/J). Imaging on T-ALL tumor bearing animals was performed just prior to and after 4 days of treatment with CAL-130. Signals at day 4 were dramatically lower in treated animals, consistent with the reduction in the WBC count and the CD4 single positive population of tumor cells (FIG. 17D). Moreover, weights of thymi, liver, spleen, and kidneys from treated Pten$^{fl/fl}$ mice were significantly less than that for animals that received vehicle control for 7 days (FIG. 17E).

Example 12

Reliance of PTEN Null Human T-ALL on PI3Kγ and PI3Kδ

To test whether CAL-130 may have similar effects on human tumors, the response of T-ALL cell lines to the compound were first analyzed. A human T-ALL cell line, CCRF-CEM, was used. T-ALL cell lines typically have multiple mutations including but not limited to Notch1 and PTEN (Palomero et al., 2007). Moreover, this particular cell line also has reduced sensitivity to conventional chemotherapies used in the treatment of T-ALL such as dexamethasone. Incubation of cultured cells with CAL-130, but not inhibitors of either PI3Kγ or PI3Kδ, prevented proliferation and promoted apoptosis within 24 hours, which persisted over 4 days of treatment (FIGS. 18A, 18B, and 23A-23J). To further demonstrate that the combined activities of PI3Kγ and PI3Kδ are essential for these processes, an shRNA vector that targeted the p110γ catalytic domain in CCRF-CEM cells was utilized. Western blot analysis revealed a >95% reduction in expression of p110γ with no effect on the other isoforms (FIG. 18C, insert). Subsequent incubation of these cells with the PI3Kδ specific inhibitor IC87114 prevented proliferation and promoted apoptosis as observed for non-transfected CCRF-CEM exposed to CAL-130 (FIGS. 18C and 18D). In contrast, IC87114 had no major effect on cells containing empty vector alone; neither did siRNA knockdown of either PIK3CA or PIK3CB (FIG. 23K-23N). These observations are consistent with the in vivo studies demonstrating that PI3Kγ and PI3Kδ are strictly required for the proliferation and survival of T-ALL lymphoblasts. Moreover, blockade of these two isoforms significantly enhanced the apoptotic properties of dexamethasone, a drug of considerable importance in the treatment of various lymphoid malignancies including T-ALL (FIG. 18E-18H) (Beesley et al., 2009).

Figure 19A:
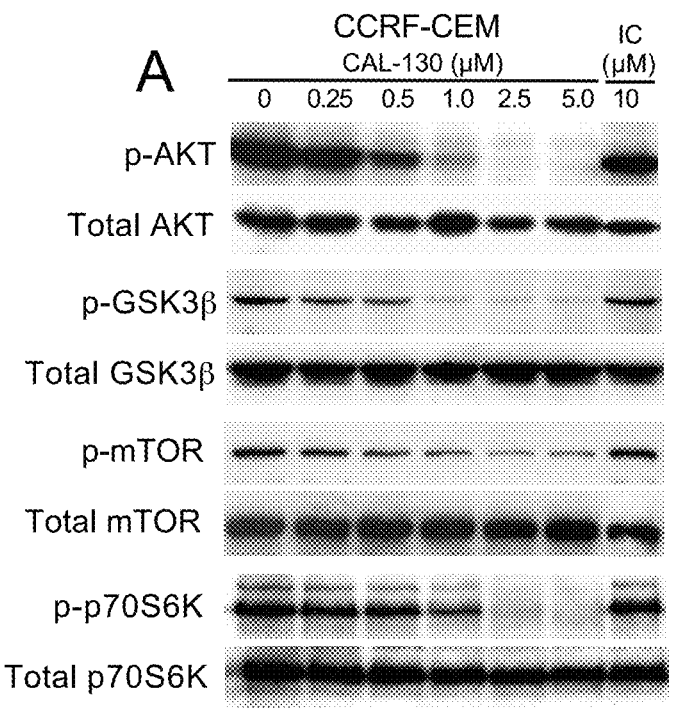
Figure 19B:
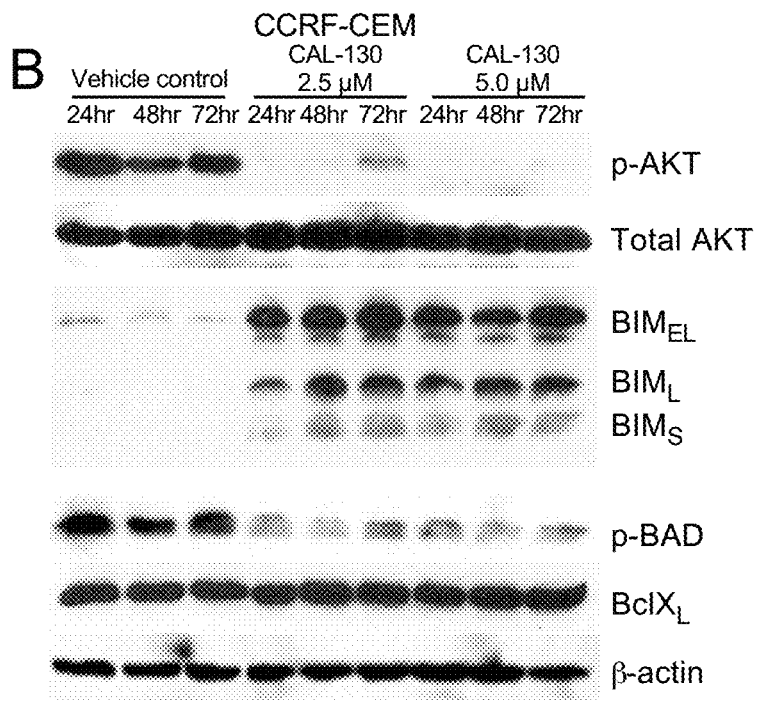

The PI3K/Akt signaling pathway can play a major role in cell cycle progression and growth of tumors by regulating the activation state of the downstream targets such as glycogen synthase kinase-3β (GSK3β) and mTOR (Schmelzle and Hall, 2000; Cohen and Frame, 2001). PI3K/Akt mediated phosphorylation suppresses the function of the former and promotes the activity of the latter. Tumor cell survival, on the other hand, is largely mediated by the ability of this pathway to inactivate proapoptotic effectors such as the BH3-only pro-apoptotic protein BAD and to repress the expression of BIM, both of which participate in the mitochondria-dependent cell death pathway (Strasser et al., 2000; Duronio, 2008). Therefore, the ability of CAL-130 treatment to interfere with such events was examined. Indeed, CCRF-CEM cells exposed to increasing concentration of drug exhibited a corresponding reduction and complete abrogation of Akt (Ser473) phosphorylation at 2.5 µM (FIG. 19A). Downstream targets of this protein kinase were also affected as evidenced by the reduction in phosphorylation of GSK3β and mTOR. Consistent with the importance of PI3K in tumor cell survival, CAL-130 treatment resulted in a reduction in phosphorylation of BAD, as well as an enhanced expression of its counterpart BIM (including the L and S isoforms) (FIG. 19B). The latter would also explain in part the synergy between CAL-130 and dexamethasone, as BIM expression is required for glucocorticoid-induced apoptosis (Erlacher et al., 2005; Wang et al., 2003).

Figure 19C:
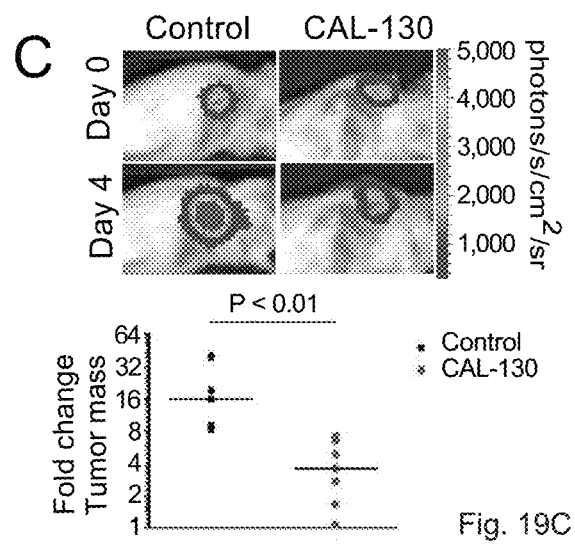
FIGS. 19C and 19D show the effect of the PI3Kδ specific inhibitor IC87114 (10 μM) on proliferation and survival, respectively, of CCRF-CEM cells in which p110γ expression was knocked down by shRNA transfection. * P<0.01, P<0.001 for p110γ shRNA treated with IC87114 versus non-silencing vector treated with IC87114. Insert depicts Western blot analysis for p110 catalytic domains.
Figure 19D:
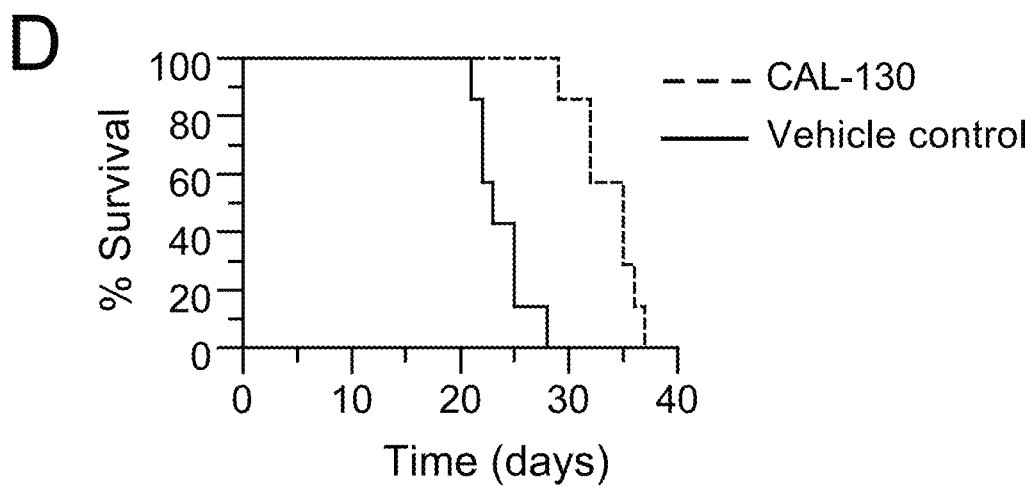

To assess the in vivo relevance of these observations, the ability of CAL-130 to prevent the proliferation of CCRF-CEM cells implanted subcutaneously or to prolong the survival of NOD.Cg-Prkdc$^{scid}$ Il2rg$^{tm1Wjl}$/Sz that received these cells intravenously was evaluated. In the former, luciferase expressing CCRF-CEM cells were injected into the flanks of immunodeficient mice and allowed to grow for 1 week before administering vehicle control or inhibitor (10 mg kg$^{-1}$ every 8 hours) for a total of 4 days. In the latter, treatment commenced 3 days post-injection of tumor cells for a total of 7 days. Bioimaging of subcutaneous tumors revealed a 5-fold difference in luminescence in CAL-130 treated versus vehicle control treated animals (FIG. 19C). This translated into an increase in median survival time for treated animals with systemic disease of 35 days versus 23 days for mice that received vehicle control alone (FIG. 19D).

Figure 20A:
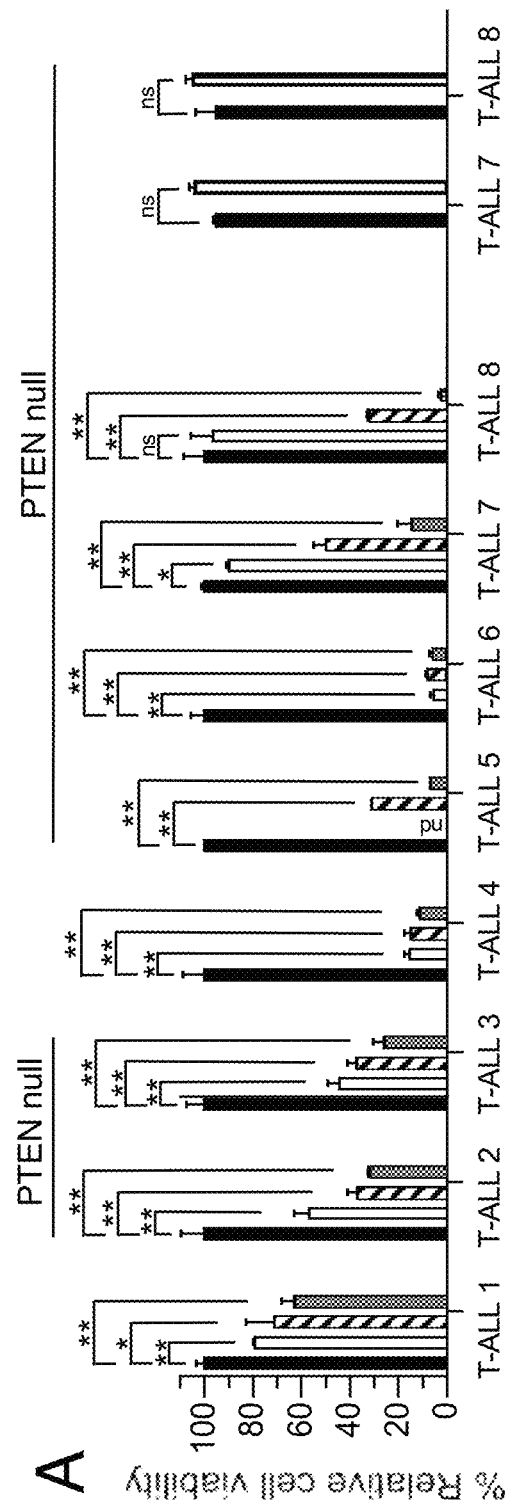

As the continued passage of rapidly growing tumor lines can result in genetic alterations distinct from the cell from which it was originally derived, the effect of CAL-130 on primary T-ALL samples isolated from patients with active disease was also evaluated. Consistent with the animal studies, human tumor cells devoid of PTEN were exquisitely sensitive to dual inhibition of PI3Kγ/δ, but not single inhibition of PI3Kδ, which resulted in a reduction in tumor cell viability as well as in Akt phosphorylation in response to treatment (FIGS. 20A-20C and data not shown). Interestingly, one primary sample that not only expressed PTEN (T-ALL 4) but also high levels of phospho-Akt, was as responsive to CAL-130 as its PTEN null counterparts. This would suggest that T-ALL sensitivity to a PI3Kγ/δ dual inhibitor might correlate better with the degree of Akt phosphorylation rather than with PTEN expression. As observed with primary mouse T-ALL, human tumors did not appear to over-express any of the four class I PIK3C isoforms (FIG. 20D).

Oncogenesis is a complex and multigenic process that often involves constitutive activation of the PI3K signaling pathway. Most notably are the gain-of-function mutations frequently found in PIK3CA, the gene that encodes for the p110α catalytic subunit, and genetic alterations that lead to the inactivation of the tumor suppressor gene Pten (Samuels et al., 2004; Zunder et al., 2008; Sufis and Parsons, 2003; Salmena et al., 2008). In the latter scenario, the possibility exists that the unregulated activity of any of the four class I PI3K isoforms could drive tumor development. For instance, previous reports demonstrate that PI3Kβ is essential for the induction, growth, and survival of PTEN-deficient tumors of epithelial cell origin (Jia et al., 2008; Wee et al., 2008). Moreover, it has been suggested that all class I PI3K isoforms are capable of coupling to upstream signaling pathways in which they are not normally engaged, thus compensating for inhibition/genetic deletion of a particular isoform (Foukas et al., 2010). To date, no conclusive evidence exists to implicate PI3Kβ or any other class I PI3K in the genesis of hematological malignancies such as T-ALL.

These results demonstrate that in the absence of physiological regulation, the activity of either PI3Kγ or PI3Kδ is sufficient for the malignant transformation of T cell progenitors in a living animal. This is exemplified by the similar onset of disease and percent survival of mice lacking either p110γ or p110δ, and the rare incidence of tumor development in their combined absence. Moreover, pharmacological blockade of both p110γ/δ dramatically impacted on tumor cell proliferation and survival as demonstrated in CAL-130 treatment of diseased Lck/Pten$^{fl/fl}$ mice, IC87114 treatment of diseased Lck/Pten$^{fl/fl}$ Pik3cg$^{-/-}$ mice as well as CAL-130 treatment of PTEN null human T-ALL primary tumors or tumor cell lines; no such effects were observed with siRNA knockdown of either p110α or p110β, and selective blockade of PI3Kδ with IC87114 was ineffective in reducing the viability of primary human T-ALL samples. These results would suggest that propagation of upstream signaling pathways critical for the development and/or survival of PTEN null T-ALL tumors rely on PI3Kγ and PI3Kδ and that the remaining isoforms (i.e. alpha and beta) cannot adequately compensate for their inactivity. Clearly, the same PI3K isoforms can participate in both tumorigenesis and tumor maintenance.

It has previously been established that PTEN loss is necessary but not sufficient to cause the malignant transformation of T cell progenitors (Liu et al., 2010; Guo et al., 2011). This typically requires additional genetic events such as chromosomal translocations involving the T cell receptor α/δ locus and c-myc oncogene (Bernard et al., 1988; Finger et al., 1986), which are acquired during the transition from CD4$^-$CD8$^-$ DN to CD4$^+$CD8$^+$ DP development stage. Despite the presence of these strong oncogenic signals, the combined absence of PI3Kγ and PI3Kδ significantly impaired leukemogenesis suggesting that loss of these isoforms can act as a tumorigenic bottleneck. Although it is possible that the overall reduction in CD4$^+$CD8$^+$ DP thymocyte numbers can partially account for the lower tumor incidence, it is unlikely because the transition from DN to DP thymocyte population in the double knockout mice is relatively normal (Swat et al., 2005). That is to say, there is no major deficiency in the number of early T cell progenitors that could undergo malignant transformation in the absence of PTEN activity. Yet, not only is tumorigenesis disrupted in TKO mice but the abnormality observed in T cell development persisted as well. This is in contrast to the severe defect in thymocyte development associated with a genetic deletion of phosphoinositide-dependent kinase 1 (PDK1) (Hinton et al., 2004), a direct downstream target of class I PI3K, which can be overcome by the loss of PTEN resulting in near normal numbers of thymocytes and peripheral T cells (Finlay et al., 2009). Similarly, PTEN deficiency can bypass a defect in either IL-7R or pre-TCR signaling, which are critical for the normal development and survival of T cells (Hagenbeek et al., 2004). In stark contrast to these studies is the inability of a PTEN deficient state to promote thymocyte proliferation and development in triple mutant Lck/Pten$^{fl/fl}$; Pik3cg$^{-/-}$; pik3cd$^{-/-}$ mice.

Thus, developmental and genomic events responsible for the generation as well as the malignant transformation of T cells in the context of a PTEN deficient state are critically reliant on proliferation and survival signals provided by PI3Kγ and PI3Kδ. It is interesting to note that although PTEN appears to play a key role in regulating the activities of class 1 PI3K, it is not the only phosphatase in T cells. SHIP1 (SH2-containing inositol-5'-phosphatase) is also capable of hydrolyzing PIP3 and has been shown to play an important role in the immunoregulatory capacity and development of specific subsets of T cells (Tarasenko et al., 2007; Collazo et al., 2009). Although deletion of SHIP1 alone in T cell progenitors is not sufficient to induce leukemogenesis, low levels of this phosphatase in conjunction with PTEN inactivation have been reported in human T-ALL tumors suggesting that inactivation of both phosphatases contribute to the hyperactivation of the PI3K/Akt signaling pathway (Lo et al., 2009). The discovery that both PI3Kγ and PI3Kδ are the engines that help drive the oncogenic process in T cell progenitors in the absence of appropriate regulation and can provide sufficient growth and survival signals necessary for tumor cell maintenance makes them attractive targets for therapy in such clinical cases. Moreover, dual inhibition of PI3Kγ and PI3Kδ in combination with conventional chemotherapies such as glucocorticoids may be of particular clinical utility in such individuals as they are more likely to fail induction chemotherapy and relapse (Gutierrez et al., 2009; Jotta et al., 2010).

It has been suggested that a complex signaling network involving PI3K exists between leukemic and supporting cells in the tissue microenvironment that may contribute to disease progression and drug resistance (Ayala et al., 2009; Konopleva et al., 2009; Burger et al., 2009). This is exemplified by the recent observations that the PI3Kδ specific inhibitor CAL-101 reduces levels of circulating chemokines known to contribute to tissue localization of chronic lymphocytic leukemic cells (Hoellenriegel et al., 2011). Consequently, this results in a generalized lymphocytosis during treatment of patients with this hematological malignancy. In contrast, a dramatic and sustained reduction in peripheral blood T-ALL cells within hours of CAL-130 treatment of diseased Lck/Pten$^{fl/fl}$ mice (data not shown) was observed. That said, it is possible that paracrine and/or autocrine signaling responsible for T-ALL survival in tissues may be disrupted by simultaneously blocking the activities of PI3Kγ and PI3Kδ. Further work will be required to establish the role of these PI3K isoforms in supporting microenvironmental interactions in T-ALL.

In the broader perspective, the results indicate that in the absence of PTEN mediated regulation, distinct class I PI3Ks can predominate in the development and survival of tumors in a manner that is most likely to involve isoforms that normally play a critical role in the function of that particular cell type. Furthermore, it is possible to target cancer cells by exploiting their "addiction" to the activity of distinct PI3K isoforms that are not themselves classical oncogenes. More generally, by identifying PI3Kγ and PI3Kδ as key therapeutic targets, it may be possible to limit toxicities that would be associated with the administration of pan-PI3K or Akt inhibitors including perturbations in insulin signaling and glucose metabolism (Crouthamel et al., 2009).

DOCUMENTS

Anderson G, Jenkinson E J. Lymphostromal interactions in thymic development and function. Nat Rev Immunol. 2001; 1: 31-40. [PubMed: 11905812] Armstrong, F., Brunet de la Grange, P., Gerby, B., Rouyez, M C, Calvo, J., Fontenay, M., Boissel, N., Dombret, H., Baruchel, A., Landman-Parker, J., Romeo, P. H. et al. (2009). NOTCH is a key regulator of human T-cell acute leukemia initiating cell activity. Blood 113, 1730-1740.

Ashwell J D, Lu F W, Vacchio M S. Glucocorticoids in T cell development and function. Annu Rev Immunol. 2000; 18: 309-345. [PubMed: 10837061]

Ayala, F., Dewar, R., Kieran, M., and Kalluri, R. (2009). Contribution of bone microenvironment to leukemogenesis and leukemia progression. Leukemia 23, 2233-2341.

Beesley, A H, Firth, M J, Ford, J., Weller, R E, Freitas, J R, Perera, K U, and Kees, U R (2009). Glucocorticoid resistance in T-lineage acute lymphoblastic leukaemia is associated with a proliferative metabolism. Br. J. Cancer 100, 1926-1936.

Bernard, O., Larsen, C J, Hampe, A., Mauchauffe, M., Berger, R. and Mathieu-Mahul, D. (1988). Molecular mechanisms of a t(8; 14)(q24; q11) translocation juxtaposing c-myc and TcR-alpha genes in a T-cell leukaemia: involvement of a V alpha internal heptamer. Oncogene 2, 195-200.

Borowski C, Martin C, Gounari F, et al. On the brink of becoming a T cell. Curr Opin Immunol. 2002; 14: 200-206. [PubMed: 11869893]

Burger, J A, Ghia, P., Rosenwald, A., and Caligaris-Cappio, F. (2009). The microenvironment in mature B-cell malignancies: a target for new treatment strategies. Blood 114, 3367-3375.

Cantley L C. The phosphoinositide 3-kinase pathway. Science. 2002; 296: 1655-1657. [PubMed: 12040186]

Carnero, A., Blanco-Aparicio, C., Renner, O., Link, W., and Leal, J F (2008). The PTEN/PI3K/AKT signalling pathway in cancer, therapeutic implications. Curr. Cancer Drug Targets 8, 187-198.

Cella M, Fujikawa K, Tassi I, et al. Differential requirements for Vav proteins in DAP10- and ITAM-mediated N K cell cytotoxicity. J Exp Med. 2004; 200: 817-823. [PMCID: PMC2211968] [PubMed: 15365099]

Clayton E, Bardi G, Bell S E, et al. A crucial role for the p110delta subunit of phosphatidylinositol 3-kinase in B cell development and activation. J Exp Med. 2002; 196: 753-763. [PMCID: PMC2194055] [PubMed: 12235209] Cohen, P. and Frame, S. (2001). The renaissance of GSK3. Nat. Rev. Mol. Cell. Biol. 2, 769-776.

Collazo, M M, Wood, D., Paraiso, K H, Lund, E., Engelman, R W, Le, C T, Stauch, D., Kotsch, K. and Kerr, W G (2009). SHIP limits immunoregulatory capacity in the T-cell compartment. Blood 113, 2934-2944.

Collins T L, Deckert M, Altman A. Views on Vay. Immunol Today. 1997; 18: 221-225. [PubMed: 9153953]

Crouthamel, M C, Kahana, J A, Korenchuk, S., Zhang, S Y, Sundaresan, G., Eberwein, D J, Brown, K. K. and Kumar, R. (2009). Mechanism and management of AKT inhibitor-induced hyperglycemia. Clin. Cancer Res. 15, 217-225.

Downward J. P I 3-kinase, Akt and cell survival. Semin Cell Dev Biol. 2004; 15: 177-182. [PubMed: 15209377]

Dudley E C, Petrie H T, Shah L M, Owen M J, Hayday A C. T cell receptor beta chain gene rearrangement and selection during thymocyte development in adult mice. Immunity. 1994; 1: 83-93. [PubMed: 7534200] Duronio, V. (2008). The life of a cell: apoptosis regulation by the PI3K/PKB pathway. Biochem. J. 415, 333-344.

Erlacher, M., Michalak, E M, Kelly, P N, Labi, V., Niederegger, H., Coultas, L., Adams, J M, Strasser, A., and Villunger, A. (2005). BH3-only proteins Puma and Bim are rate-limiting for gamma-radiation- and glucocorticoid-induced apoptosis of lymphoid cells in vivo. Blood 106, 4131-4138.

Fabian, M A, Biggs, W H 3rd, Treiber, D K, Atteridge, C E, Azimioara, M D, Benedetti, M G, Carter, T A, Ciceri, P., Edeen, P. T., and Floyd, M. (2005). A small molecule-kinase interaction map for clinical kinase inhibitors. Nat. Biotechnol. 23, 329-336.

Falk I, Nerz G, Haidl I, Krotkova A, Eichmann K. Immature thymocytes that fail to express TCR-beta and/or TCR-gamma delta proteins die by apoptotic cell death in the CD44(−)CD25(−) (DN4) subset. Eur J Immunol. 2001; 31: 3308-3317. [PubMed: 11745348]

Finger, L R, Harvey, R C, Moore, R C, Showe, L. C. and Croce, C M (1986). A common mechanism of chromosomal translocation in T- and B-cell neoplasia. Science 234, 982-985.

Finlay, D K, Sinclair, L V, Feijoo, C., Waugh, C M, Hagenbeek, T J, Spits, H. and Cantrell, D A (2009). Phosphoinositide-dependent kinase 1 controls migration and malignant transformation but not cell growth and proliferation in PTEN-null lymphocytes. J. Exp. Med. 206, 2441-2454.

Foukas, L C, Berenjeno, I M, Gray, A., Khwaja, A. and Vanhaesebroeck, B. (2010). Activity of any class IA PI3K isoform can sustain cell proliferation and survival. Proc. Natl. Acad. Sci. USA. 107, 11381-11386.

Franke T F, Hornik C P, Segev L, Shostak G A, Sugimoto C. PI3K/Akt and apoptosis: size matters. Oncogene. 2003; 22: 8983-8998. [PubMed: 14663477]

Fruman D A, Snapper S B, Yballe C M, et al. Impaired B cell development and proliferation in absence of phosphoinositide 3-kinase p85alpha. Science. 1999; 283: 393-397. [PubMed: 9888855]

Germain R N. T-cell development and the CD4-CD8 lineage decision. Nat Rev Immunol. 2002; 2: 309-322. [PubMed: 12033737]

Gratiot-Deans J, Ding L, Turka L A, Nunez G. bcl-2 proto-oncogene expression during human T cell development: evidence for biphasic regulation. J Immunol. 1993; 151: 83-91. [PubMed: 8326141]

Guo, W., Lasky, J L, Chang, C J, Mosessian, S., Lewis, X., Xiao, Y., Yeh, J E, Chen, J Y, Iruela-Arispe, M L, Varella-Garcia, M. et al. (2008). Multi-genetic events collaboratively contribute to Pten-null leukaemia stem-cell formation. Nature 453, 529-533.

Guo, W., Schubbert, S., Chen, J Y, Valamehr, B., Mosessian, S., Shi, H., Dang, N H, Garcia, C., Theodoro, M F, Varella-Garcia, M. et al. (2011). Suppression of leukemia development caused by PTEN loss. Proc. Natl. Acad. Sci. USA. 108, 1409-1414.

Gutierrez, A., Sanda, T., Grebliunaite, R., Carracedo, A., Salmena, L., Ahn, Y., Dahlberg, S., Neuberg, D., Moreau, L A, Winter, S. S. et al. (2009). High frequency of PTEN, PI3K, and AKT abnormalities in T-cell acute lymphoblastic leukemia. Blood 114, 647-650.

Hagenbeek, T. J. and Spits, H. (2008). T-cell lymphomas in T-cell-specific Pten-deficient mice originate in the thymus. Leukemia 22, 608-619.

Hagenbeek, T J, Naspetti, M., Malergue, F., Gargon, F., Nunes, J A, Cleutjens, K B, Trapman, J., Krimpenfort, P. and Spits, H. (2004). The loss of PTEN allows TCR alphabeta lineage thymocytes to bypass I L-7 and Pre-TCR-mediated signaling. J. Exp. Med. 200, 883-889.

Hennet, T., Hagen, F. K., Tabak, L. A. and Marth, J. D. (1995). T-cell-specific deletion of a polypeptide N-acetyl-galactosaminyl-transferase gene by site-directed recombination. Proc. Natl. Acad. Sci. USA 92, 12070-12074.

Hickey, F. B. and Cotter, T G (2005). BCR-ABL regulates phosphatidylinositol 3-kinase-p110gamma transcription and activation and is required for proliferation and drug resistance. J. Biol. Chem. 281, 2441-2450.

Hinton, H J, Alessi, D. R. and Cantrell, D A (2004). The serine kinase phosphoinositide-dependent kinase 1 (PDK1) regulates T cell development. Nat. Immunol. 5, 539-545.

Hoellenriegel, J., Meadows, S A, Sivina, M., Wierda, W G, Kantarjian, H., Keating, M J, Giese, N., O'Brien, S., Yu, A., Miller, L L, Lannutti, B J, Burger, J A (2011). The phosphoinositide 3'-kinase delta inhibitor, CAL-101, inhibits B-cell receptor signaling and chemokine networks in chronic lymphocytic leukemia. Blood 118, 3603-3612.

Huang, W. C. and Hung, M C (2009). Induction of Akt activity by chemotherapy confers acquired resistance. J. Formos. Med. Assoc. 108, 180-189.

Jackson S P, Schoenwaelder S M, Goncalves I, Nesbitt W S, Yap C L, Wright C E, Kenche V, Anderson K E, Dopheide S M, Yuan Y. et al. (2005). P I 3-kinase p110beta: a new target for antithrombotic therapy. Nat. Med. 11, 507-514.

Ji, H., Rintelen, F., Waltzinger, C., Bertschy Meier, D., Bilancio, A., Pearce, W., Hirsch, E., Wymann, M P, Ruckle, T., Camps, M. et al. (2007). Inactivation of PI3Kgamma and PI3Kdelta distorts T-cell development and causes multiple organ inflammation. Blood 110, 2940-2947.

Jia, S., Liu, Z., Zhang, S., Liu, P., Zhang, L., Lee, S H, Zhang, J., Signoretti, S., Loda, M., Roberts, T. M. et al. (2008). Essential roles of PI(3)K-p110beta in cell growth, metabolism and tumorigenesis. Nature 454, 776-779.

Jordan M S, Singer A L, Koretzky G A. Adaptors as central mediators of signal transduction in immune cells. Nat Immunol. 2003; 4: 110-116. [PubMed: 12555096]

Jotta, P Y, Ganazza, M A, Silva, A., Viana, M B, da Silva, M J, Zambaldi, L J, Barata, J T, Brandalise, S. R. and Yunes, J A (2010). Negative prognostic impact of PTEN mutation in pediatric T-cell acute lymphoblastic leukemia. Leukemia 24, 239-242.

Kang, S., Denley, A., Vanhaesebroeck, B., and Vogt, P K (2006). Oncogenic transformation induced by the p110beta, -gamma, and -delta isoforms of class I phosphoinositide 3-kinase. Proc. Natl. Acad. Sci. USA. 103, 1289-1294.

Katso, R. (2001). Cellular function of phosphoinositide 3-kinases: implications for development, homeostasis, and cancer. Ann. Rev. Cell Dev. Biol. 17, 615-675.

Kong Y Y, Fischer K D, Bachmann M F, et al. Vav regulates peptide-specific apoptosis in thymocytes. J Exp Med. 1998; 188: 2099-2111. [PMCID: PMC2212394] [PubMed: 9841924]

Konopleva, M., Tabe, Y., Zeng, Z., and Andreeff, M. (2009). Therapeutic targeting of microenvironmental interactions in leukemia: mechanisms and approaches. Drug Resist. Updat. 12, 103-113.

Kroemer G. The proto-oncogene Bcl-2 and its role in regulating apoptosis. Nat Med. 1997; 3: 614-620. [PubMed: 9176486]

Larson Gedman, A., Chen, Q., Kugel Desmoulin, S., Ge, Y., LaFiura, K., Haska, C L, Cherian, C., Devidas, M., Linda, S B, Taub, J. W. et al. (2009). The impact of NOTCH1, FBW7 and PTEN mutations on prognosis and downstream signaling in pediatric T-cell acute lymphoblastic leukemia: a report from the Children's Oncology Group. Leukemia 23, 1417-1425.

Lewis C M, Broussard C, Czar M J, Schwartzberg P L. Tec kinases: modulators of lymphocyte signaling and development. Curr Opin Immunol. 2001; 13: 317-325. [PubMed: 11406363]

Linette G P, Korsmeyer S J. Differentiation and cell death: lessons from the immune system. Curr Opin Cell Biol. 1994; 6: 809-815. [PubMed: 7880527] Liu, X., Karnell, J L, Yin, B., Zhang, R., Zhang, J., Li, P., Choi, Y., Maltzman, J S, Pear, W S, Bassing, C. H. et al. (2010). Distinct roles for PTEN in prevention of T cell lymphoma and autoimmunity in mice. J. Clin. Invest. 20, 2497-2507.

Lo, T C, Barnhill, L M, Kim, Y., Nakae, E A, Yu, A L, and Diccianni, M B (2009). Inactivation of SHIP1 in T-cell acute lymphoblastic leukemia due to mutation and extensive alternative splicing. Leuk. Res. 33, 1562-1566.

Magallon, J., Chen, J C, Rabbani, L., Dangas, G., Yang, J., Bussel, J., and Diacovo, T. (2011). Humanized mouse model of thrombosis is predictive of the clinical efficacy of antiplatelet agents. Circulation 123, 319-326.

Maser, R S, Choudhury, B., Campbell, P J, Feng, B., Wong, K K, Protopopov, A., O'Neil, J., Gutierrez, A., Ivanova, E., Perna, I. et al. (2007). Chromosomally unstable mouse tumours have genomic alterations similar to diverse human cancers. Nature 447, 966-971.

McKean D J, Huntoon C J, Bell M P, et al. Maturation versus death of developing double-positive thymocytes reflects competing effects on Bcl-2 expression and can be regulated by the intensity of CD28 costimulation. J Immunol. 2001; 166: 3468-3475. [PubMed: 11207305]

Melendez A J, Gillooly D J, Harnett M M, Allen J M. Aggregation of the human high affinity immunoglobulin G receptor (FcgammaRI) activates both tyrosine kinase and G protein-coupled phosphoinositide 3-kinase isoforms. Proc Natl Acad Sci USA. 1998; 95: 2169-2174. [PMCID: PMC19285] [PubMed: 9482857]

Michie A M, Zuniga-Pflucker J C. Regulation of thymocyte differentiation: pre-TCR signals and beta-selection. Semin Immunol. 2002; 14: 311-323. [PubMed: 12220932]

Okkenhaug K, Bilancio A, Emery J L, Vanhaesebroeck B. Phosphoinositide 3-kinase in T cell activation and survival. Biochem Soc Trans. 2004; 32: 332-335. [PubMed: 15046602]

Okkenhaug K, Bilancio A, Farjot G, et al. Impaired B and T cell antigen receptor signaling in p110delta P I 3-kinase mutant mice. Science. 2002; 297: 1031-1034. [PubMed: 12130661]

Okkenhaug K, Vanhaesebroeck B. PI3K in lymphocyte development, differentiation and activation. Nat Rev Immunol. 2003; 3: 317-330. [PubMed: 12669022]

Palomero, T., Dominguez, M., and Ferrando, A A (2008). The role of the PTEN/AKT Pathway in NOTCH1-induced leukemia. Cell Cycle 7, 965-970.

Penit C, Lucas B, Vasseur F. Cell expansion and growth arrest phases during the transition from precursor (CD4−8−) to immature (CD4+8+) thymocytes in normal and genetically modified mice. J Immunol. 1995; 154: 5103-5113. [PubMed: 7730616]

Punt J A, Suzuki H, Granger L G, Sharrow S O, Singer A. Lineage commitment in the thymus: only the most differentiated (TCRhibcl-2hi) subset of CD4+CD8+ thymocytes has selectively terminated CD4 or CD8 synthesis. J Exp Med. 1996; 184: 2091-2099. [PMCID: PMC2196385] [PubMed: 8976166]

Puri K D, Doggett T A, Huang C Y, et al. The role of endothelial PI3Kγ activity in neutrophil trafficking. Blood. 2005; 106: 150-157. [PMCID: PMC1895128] [PubMed: 15769890]

Puri, K D, Doggett, T A, Douangpanya, J., Hou, Y., Tino, W T, Wilson, T., Graf, T., Clayton, E., Turner, M., Hayflick, J. S. et al. (2004). Mechanisms and implications of phosphoinositide 3-kinase 6 in promoting neutrophil trafficking into inflamed tissue. Blood 103, 3448-3456.

Reynolds L F, Smyth L A, Norton T, et al. Vav1 transduces T cell receptor signals to the activation of phospholipase C-gammal via phosphoinositide 3-kinase-dependent and -independent pathways. J Exp Med. 2002; 195: 1103-1114. [PMCID: PMC2193701] [PubMed: 11994416]

Rodriguez-Borlado L, Barber D F, Hernandez C, et al. Phosphatidylinositol 3-kinase regulates the CD4/CD8 T cell differentiation ratio. J Immunol. 2003; 170: 4475-4482. [PubMed: 12707323]

Sadhu, C., Masinosky, B., Dick, K., Sowell, C. G., and Staunton, D E (2003). Essential role of Phosphoinositide 3-kinase 6 in neutrophil directional movement. J. Immunol. 170, 2647-2654.

Safran, M., Kim, W Y, Kung, A L, Horner, J W, DePinho, R A and Kaelin, W G Jr. (2003). Mouse reporter strain for noninvasive bioluminescent imaging of cells that have undergone Cre-mediated recombination. Mol. Imaging 2, 297-302.

Sakai et al. (1998) PTEN Gene Alterations in Lymphoid Neoplasms. Blood 92, p. 3410-3415.

Salmena, L., Carracedo, A., and Pandolfi, P P (2008). Tenets of PTEN tumor suppression. Cell 133, 403-414.

Samuels, Y., Wang, Z., Bardelli, A., Silliman, N., Ptak, J., Szabo, S., Yan, H., Gazdar, A., Powell, S M, Riggins, G. J. et al. (2004). High frequency of mutations of the PIK3CA gene in human cancers. Science 304, 554.

Sasaki T, Me-Sasaki J, Jones R G, et al. Function of PI3Kgamma in thymocyte development, T cell activation, and neutrophil migration. Science. 2000; 287: 1040-1046. [PubMed: 10669416]

Schmelzle, T. and Hall, M. N. (2000). mTor, a central controller of cell growth. Cell, 103, 253-262.

Sentman C L, Shutter J R, Hockenbery D, Kanagawa O, Korsmeyer S J. bcl-2 inhibits multiple forms of apoptosis but not negative selection in thymocytes. Cell. 1991; 67: 879-888. [PubMed: 1835668]

Shelton J G, Steelman L S, White E R, McCubrey J A. Synergy between PI3K/Akt and Raf/MEK/ERK pathways in IGF-1R mediated cell cycle progression and prevention of apoptosis in hematopoietic cells. Cell Cycle. 2004; 3: 372-379. [PubMed: 14726697]

Shortman K, Wu L. Early T lymphocyte progenitors. Annu Rev Immunol. 1996; 14: 29-47. [PubMed: 8717506]

Silva, A., Yunes, J A, Cardoso, B A, Martins, L R, Jotta, P Y, Abecasis, M., Nowill, A E, Leslie, N R, Cardoso, A. A. and Barata, J T (2008). PTEN posttranslational inactivation and hyperactivation of the PI3K/Akt pathway sustain primary T cell leukemia viability. J. Clin. Invest. 118, 3762-3774. Sopasakis, V R, Liu, P., Suzuki, R., Kondo, T., Winnay, J., Tran, T T, Asano, T., Smyth, G., Sajan, M P, Farese, R. V. et al. (2010). Specific roles of the p110alpha isoform of phosphatidylinsositol 3-kinase in hepatic insulin signaling and metabolic regulation. Cell Metab. 11, 220-230.

Strasser A, Harris A W, Cory S. bcl-2 transgene inhibits T cell death and perturbs thymic self-censorship. Cell. 1991; 67: 889-899. [PubMed: 1959134]

Strasser, A., Puthalakath, H., Bouillet, P., Huang, D C, O'Connor, L., O'Reilly, L A, Cullen, L., Cory, S. and Adams, J M (2000). The role of bim, a proapoptotic BH3-only member of the Bcl-2 family in cell-death control. Ann. N. Y. Acad. Sci. 917, 541-548.

Sujobert, P., Bardet, V., Cornillet-Lefebvre, P., Hayflick, J S, Prie, N., Verdier, F., Vanhaesebroeck, B., Muller, O., Pesce, F., Ifrah, N. et al. (2005). Essential role for the p110delta isoform in phosphoinositide 3-kinase activation and cell proliferation in acute myeloid leukemia.

Sulis, M. L. and Parsons, R. (2003). PTEN: from pathology to biology. Trends Cell Biol. 13, 478-483. Blood 106, 1063-1066.

Suzuki H, Terauchi Y, Fujiwara M, et al. Xid-like immunodeficiency in mice with disruption of the p85alpha subunit of phosphoinositide 3-kinase. Science. 1999; 283: 390-392. [PubMed: 9888854]

Suzuki, A., Yamaguchi M T, Ohteki T, Sasaki T, Kaisho T, Kimura Y, Yoshida R,

Wakeham A, Higuchi T, Fukumoto M. et al. (2001). T cell-specific loss of Pten leads to defects in central and peripheral tolerance. Immunity 14, 523-534. Swat, W., Montgrain, V., Doggett, T A, Douangpanya, J., Puri, K., Vermi, W., and Diacovo, T G (2006). Essential role of PI3Kdelta and PI3Kgamma in thymocyte survival. Blood 107, 2415-2422.

Tarasenko, T., Kole, H K, Chi, A W, Mentink-Kane, M M, Wynn, T. A. and Bolland, S. (2007). T cell-specific deletion of the inositol phosphatase SHIP reveals its role in regulating Th1/Th2 and cytotoxic responses. Proc. Natl. Acad. Sci. USA 104, 11382-11387.

Trotman, L C, Niki, M., Dotan, Z A, Koutcher, J A, Di Cristofano, A., Xiao, A., Khoo, A S, Roy-Burman, P., Greenberg, N M, Van Dyke, T. et al. (2003). Pten dose dictates cancer progression in the prostate. PLoS Biol. 1, 385-396.

Vanhaesebroeck B, Leevers S J, Panayotou G, Waterfield M D. Phosphoinositide 3-kinases: a conserved family of signal transducers. Trends Biochem Sci. 1997; 22: 267-272. [PubMed: 9255069]

Wang, Z., Malone, M H, He, H., McColl, K. S., and Distelhorst, C W (2003). Microarray analysis uncovers the induction of the proapoptotic BH3-only protein Bim in multiple models of glucocorticoid-induced apoptosis. J. Biol. Chem. 278, 23861-23867.

Webb, L M, Vigorito, E., Wymann, M P, Hirsch, E., and Turner, M J (2005). Cutting edge: T cell development requires the combined activities of the p110gamma and p110delta catalytic isoforms of phosphatidylinositol 3-kinase. Immunol. 175, 2783-2787.

Wee, S., Wiederschain, D., Maira, S M, Loo, A., Miller, C., deBeaumont, R., Stegmeier, F., Yao, Y. M. and Lengauer, C. (2008). PTEN-deficient cancers depend on PIK3C B. Proc. Natl. Acad. Sci. USA. 105, 13057-13062.

Williams O, Norton T, Halligey M, Kioussis D, Brady H J. The action of Bax and bcl-2 on T cell selection. J Exp Med. 1998; 188: 1125-1133. [PMCID: PMC2212546] [PubMed: 9743531]

Wymann M P, Pirola L. Structure and function of phosphoinositide 3-kinases. Biochim Biophys Acta. 1998; 1436: 127-150. [PubMed: 9838078]

Xu H, Littman D R. The kinase-dependent function of Lck in T-cell activation requires an intact site for tyrosine autophosphorylation. Ann N Y Acad Sci. 1995; 766: 99-116. [PubMed: 7486706]

Yao R, Cooper G M. Requirement for phosphatidylinositol-3 kinase in the prevention of apoptosis by nerve growth factor. Science. 1995; 267: 2003-2006. [PubMed: 7701324]

Yuan, T. L. and Cantley, L C (2008). PI3K pathway alterations in cancer: variations on a theme. Oncogene 27, 5497-5510.

Zhao, L. and Vogt, P K (2008). Class 1 PI3K in oncogenic cellular transformation. Oncogene 27, 5486-5496.

Zunder, E R, Knight, Z A, Houseman, B T, Apsel, B., and Shokat, K M (2008). Discovery of drug-resistant and drug-sensitizing mutations in the oncogenic PI3K isoform p110 alpha. Cancer Cell 14, 180-192.

Zuniga-Pflucker J C. T-cell development made simple. Nat Rev Immunol. 2004; 4: 67-72. [PubMed: 14704769]

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

The invention claimed is:

1. A method for treating or ameliorating the effects of a lymphoid malignancy comprising administering to a subject in need thereof an effective amount of a small molecule to selectively inhibit phosphoinositide 3-kinase-delta (PI3Kd) and phosphoinositide 3-kinase-gamma (PI3Kg) isoforms, wherein the small molecule to selectively inhibit PI3Kd and PI3Kg isoforms is CAL-130, wherein the lymphoid malignancy is T-cell acute lymphoblastic leukemia (T-ALL) or T-cell acute lymphoblastic lymphoma, and wherein the CAL-130 has the chemical structure of:

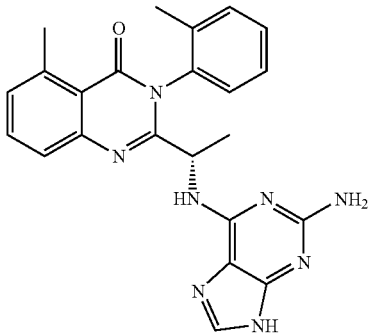 [SMILES: Cc1ccccc1-n1c([C@H](C)Nc2nc(N)nc3[nH]cnc23)nc2cccc(C)c2c1=O]

2. The method according to claim 1, wherein the lymphoid malignancy is T-ALL.

3. The method according to claim 1, further comprising co-administering to the subject at least one chemotherapeutic agent.

4. The method according to claim 3, wherein the chemotherapeutic agent is selected from the group consisting of actinomycin, amsacrine, anthracycline, busulfan, cisplatin, Cytoxan, epirubicin, hexamethylmelamineoxaliplatin, iphosphamide, mitoxantrone, taxotere, teniposide, triethylenethiophosphoramide, hydrocortisone, cortisone, methylprednisolone, prednisolone, dexamethasone,prednisone, betamethasone, triamcinolone, beclometasone, fludrocortisones, deoxycorticosterone, aldosterone, oxaliplatin, zoledronic acid, ibandronate, verapamil, podophyllotoxin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin, methotrexate, L-asparaginase, rapamycin, dibenzazepine (DBZ), uramustine, carmustine, lomustine, streptozocin, temozolomide, idarubicin, topotecan, premetrexed, 6- mercaptopurine, darcarbazine, fludarabine, arabinosycytosine, 5-fluorouracil, arabinosylcytosine, capecitabine, gemcitabine, decitabine, vinca alkaloids, paclitaxel, docetaxel, ixabepilone (Ixempra®), and combinations thereof.

5. The method according to claim 3, wherein the chemotherapeutic agent is a glucocorticoid selected from the group consisting of hydrocortisone, cortisone, methylprednisolone, prednisolone, dexamethasone, prednisone, betamethasone, triamcinolone, beclometasone, fludrocortisones, deoxycorticosterone, aldosterone, and combinations thereof.

6. The method according to claim 3, wherein the chemotherapeutic agent is dexamethasone.

7. A method for treating or ameliorating the effects of a lymphoid malignancy associated with a mutated phosphatase and tensin homolog (PTEN) gene in a subject comprising administering to the subject an effective amount of a small molecule to selectively inhibit phosphoinositide 3-kinase-delta (PI3Kd) and phosphoinositide 3-kinase-gamma (PI3Kg) isoforms, wherein the small molecule to selectively inhibit PI3Kd and PI3Kg isoforms is CAL-130, wherein the lymphoid malignancy is T-cell acute lymphoblastic leukemia (T-ALL) or T-cell acute lymphoblastic lymphoma, and wherein the CAL-130 has the chemical structure of:

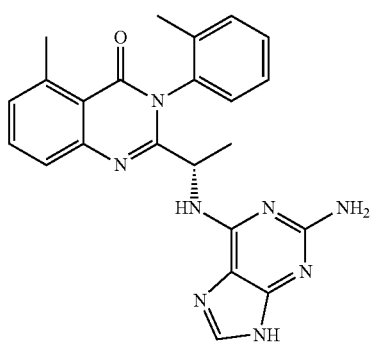 [SMILES: Cc1ccccc1-n1c([C@H](C)Nc2nc(N)nc3[nH]cnc23)nc2cccc(C)c2c1=O]

8. A pharmaceutical composition for treating the effects of a lymphoid malignancy comprising a therapeutically effective amount of CAL-130 and pharmaceutically acceptable carrier thereof, wherein the lymphoid malignancy is T-cell acute lymphoblastic leukemia (T-ALL) or T-cell acute lymphoblastic lymphoma, and wherein the CAL-130 has the chemical structure of:

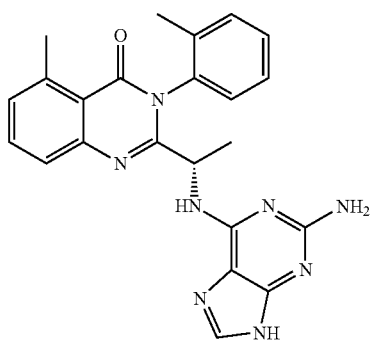 [SMILES: Cc1ccccc1-n1c([C@H](C)Nc2nc(N)nc3[nH]cnc23)nc2cccc(C)c2c1=O]

9. The pharmaceutical composition according to claim 8, which is in a unit dosage form.

10. The pharmaceutical composition according to claim 8, further comprising an effective amount of dexamethasone.

11. The method of claim 1, with the proviso that the small molecule does not comprise CAL-101.

12. The method of claim 7, with the proviso that the small molecule does not comprise CAL-101.

13. The pharmaceutical composition of claim 8, with the proviso that the small molecule does not comprise CAL-101.

14. A method for treating or ameliorating the effects of a malady comprising T-cell acute lymphoblastic leukemia (T-ALL) or T-cell acute lymphoblastic lymphoma, said method comprising administering to a subject in need thereof a therapeutically effective amount of CAL-130, wherein the CAL-130 has the chemical structure of:

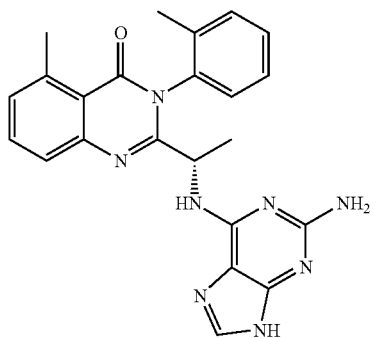 [SMILES: Cc1ccccc1-n1c([C@H](C)Nc2nc(N)nc3[nH]cnc23)nc2cccc(C)c2c1=O]

15. The method according to claim 14 wherein the malady is T-cell acute lymphoblastic leukemia (T-ALL).

* * * * *